(12) United States Patent
Eickhoff et al.

US011450809B2

(10) Patent No.: US 11,450,809 B2
(45) Date of Patent: Sep. 20, 2022

(54) COMPOSITION FOR ORGANIC ELECTRONIC DEVICES

(71) Applicant: Merck Patent GmbH, Darmstadt (DE)

(72) Inventors: Christian Eickhoff, Mannheim (DE); Amir Parham, Frankfurt am Main (DE); Jonas Kroeber, Frankfurt am Main (DE); Tobias Grossmann, Darmstadt (DE); Anja Jatsch, Frankfurt am Main (DE); Christian Ehrenreich, Darmstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 289 days.

(21) Appl. No.: 16/764,265

(22) PCT Filed: Nov. 12, 2018

(86) PCT No.: PCT/EP2018/080867
§ 371 (c)(1),
(2) Date: May 14, 2020

(87) PCT Pub. No.: WO2019/096717
PCT Pub. Date: May 23, 2019

(65) Prior Publication Data
US 2020/0395548 A1     Dec. 17, 2020

(30) Foreign Application Priority Data
Nov. 14, 2017 (EP) .................................. 17201480

(51) Int. Cl.
*H01L 51/00* (2006.01)
*C07D 251/24* (2006.01)
*C07D 333/76* (2006.01)
*C07D 405/14* (2006.01)
*C07D 409/14* (2006.01)
*C09K 11/06* (2006.01)
*H01L 51/50* (2006.01)

(52) U.S. Cl.
CPC ........ *H01L 51/0067* (2013.01); *C07D 251/24* (2013.01); *C07D 333/76* (2013.01); *C07D 405/14* (2013.01); *C07D 409/14* (2013.01); *C09K 11/06* (2013.01); *H01L 51/0054* (2013.01); *H01L 51/0058* (2013.01); *H01L 51/0072* (2013.01); *H01L 51/0073* (2013.01); *H01L 51/0074* (2013.01); *C09K 2211/1018* (2013.01); *H01L 51/0003* (2013.01); *H01L 51/0008* (2013.01); *H01L 51/5016* (2013.01); *H01L 51/5072* (2013.01); *H01L 51/5092* (2013.01); *H01L 51/5096* (2013.01)

(58) Field of Classification Search
CPC ............ H01L 51/0067; H01L 51/0058; H01L 51/0072; H01L 51/0073; H01L 51/5072; H01L 51/5092; H01L 51/0074; C09K 11/06; C07D 251/24; C07D 405/14; C07D 409/14
See application file for complete search history.

(56) References Cited

U.S. PATENT DOCUMENTS

| | | |
|---|---|---|
| 4,539,507 A | 9/1985 | VanSlyke et al. |
| 5,151,629 A | 9/1992 | VanSlyke |
| 5,840,217 A | 11/1998 | Lupo et al. |
| 6,458,909 B1 | 10/2002 | Spreitzer et al. |
| 7,294,849 B2 | 11/2007 | Thompson et al. |
| 9,266,851 B2 | 2/2016 | Yoshida et al. |
| 9,334,260 B2 | 5/2016 | Parham et al. |
| 10,622,565 B2 | 4/2020 | Parham et al. |
| 2006/0280965 A1 | 12/2006 | Kwong et al. |
| 2015/0318487 A1* | 11/2015 | Ito .................. H01L 51/5096 257/40 |
| 2015/0340618 A1 | 11/2015 | Lee et al. |
| 2016/0181548 A1 | 6/2016 | Parham et al. |
| 2016/0248023 A1 | 8/2016 | Parham et al. |
| 2017/0141328 A1 | 5/2017 | Hayer et al. |
| 2019/0006590 A1 | 1/2019 | Park et al. |

FOREIGN PATENT DOCUMENTS

| | | |
|---|---|---|
| EP | 0676461 A2 | 10/1995 |
| EP | 3336159 A1 | 6/2018 |
| KR | 101744248 B1 | 6/2017 |
| WO | WO-9827136 A1 | 6/1998 |
| WO | WO-2009021126 A2 | 2/2009 |
| WO | WO-2009069442 A1 | 6/2009 |
| WO | WO-2011046182 A1 | 4/2011 |
| WO | WO-2011057706 A2 | 5/2011 |
| WO | WO-2015014434 A1 | 2/2015 |
| WO | WO-2015169412 A1 | 11/2015 |
| WO | WO-2015192941 A1 | 12/2015 |

OTHER PUBLICATIONS

Baldo, M. et al., "Very high-efficiency green organic light-emitting devices based on electrophosphorescence", Applied Physics Letters, vol. 75, No. 1, (1999), pp. 4-6.
International Search Report for PCT/EP2018/080867 dated Jun. 12, 2019.
Written Opinion of the International Searching Authority for PCT/EP2018/080867 dated Jun. 12, 2019.

* cited by examiner

*Primary Examiner* — Khanh T Nguyen

(74) *Attorney, Agent, or Firm* — Faegre Drinker Biddle & Reath LLP

(57) ABSTRACT

The present invention relates to a composition comprising a specific bipolar host and a triphenylene derivative, to the use thereof in electronic devices and electronic devices comprising said composition.

16 Claims, No Drawings

COMPOSITION FOR ORGANIC ELECTRONIC DEVICES

CROSS-REFERENCE TO RELATED APPLICATIONS

This application is a national stage application (under 35 U.S.C. § 371) of PCT/EP2018/080867, filed Nov. 12, 2018, which claims benefit of European Application No. 17201480.5, filed Nov. 14, 2017, both of which are incorporated herein by reference in their entirety.

The present invention relates to a composition comprising a specific bipolar host and a triphenylene derivative, to the use thereof in electronic devices and electronic devices comprising said composition.

The structure of organic electroluminescent devices (e.g. OLEDs—organic light-emitting diodes or OLECs—organic light-emitting electrochemical cells) in which organic semiconductors are used as functional materials is described, for example, in U.S. Pat. Nos. 4,539,507, 5,151,629, EP 0676461 and WO 98/27136. Emitting materials used here, as well as fluorescent emitters, are increasingly organometallic complexes which exhibit phosphorescence rather than fluorescence (M. A. Baldo et al., *App. Phys. Lett.* 1999, 75, 4-6). For quantum-mechanical reasons, up to a fourfold increase in energy efficiency and power efficiency is possible using organometallic compounds as phosphorescent emitters. In general terms, however, there is still a need for improvement in OLEDs, especially also in OLEDs which exhibit triplet emission (phosphorescence), for example with regard to efficiency, operating voltage and lifetime.

The properties of organic electroluminescent devices are not only determined by the emitters used. Also of particular significance here are especially the other materials used, such as host and matrix materials, hole blocker materials, electron transport materials, hole transport materials and electron or exciton blocker materials, and among these especially the host or matrix materials. Improvements to these materials can lead to distinct improvements to electroluminescent devices.

Host materials for use in organic electronic devices are well-known to the person skilled in the art. The term "matrix material" is also frequently used in the prior art when what is meant is a host material for phosphorescent emitters. This use of the term is also applicable to the present invention. In the meantime, a multitude of host materials has been developed both for fluorescent and for phosphorescent electronic devices.

According to the prior art, ketones (for example according to WO 2004/093207 or WO 2010/006680) or phosphine oxides (for example according to WO 2005/003253) are among the matrix materials used for phosphorescent emitters. Further matrix materials according to the prior art are represented by triazines (for example WO 2008/056746, EP 0906947, EP 0908787, EP 0906948) and lactams (for example WO 2011/116865 or WO 2011/137951). In addition, according to the prior art, carbazole derivatives (for example according to WO 2005/039246, US 2005/0069729 or WO 2014/015931), indolocarbazole derivatives (for example according to WO 2007/063754 or WO 2008/056746) or indenocarbazole derivatives (for example according to WO 2010/136109 or WO 2011/000455), especially those substituted by electron-deficient heteroaromatics such as triazine, are among the matrix materials used for phosphorescent emitters. WO 2011/057706 discloses carbazole derivatives substituted by two triphenyltriazine groups. WO 2011/046182 discloses carbazole-arylene-triazine derivatives substituted by a fluorenyl group on the triazine. WO 2009/069442 discloses tricyclic systems such as carbazole, dibenzofuran or dibenzothiophene having a high level of substitution by electron-deficient heteroaromatics (e.g. pyridine, pyrimidine or triazine) as host materials. WO 2011/057706, WO 2015/014434 and WO 2015/169412 disclose further host materials comprising triazine-dibenzofuran-carbazole derivatives and triazine-dibenzothiophene-carbazole derivatives inter alia, wherein the triazine is bonded to the dibenzofuran or dibenzothiophene optionally by a linker. WO 2009/021126 and US 2015/0340618 describe terphenylene derivatives as host materials.

A further means of improving the performance data of electronic devices, especially of organic electroluminescent devices, is to use combinations of two or more materials, especially host materials or matrix materials.

U.S. Pat. No. 6,392,250 B1 discloses the use of a mixture consisting of an electron transport material, a hole transport material and a fluorescent emitter in the emission layer of an OLED. With the aid of this mixture, it was possible to improve the lifetime of the OLED compared to the prior art.

U.S. Pat. No. 6,803,720 B1 discloses the use of a mixture comprising a phosphorescent emitter and a hole transport material and an electron transport material in the emission layer of an OLED. Both the hole transport material and the electron transport material are small organic molecules.

According to WO 2015/192941, it is possible to use, for example, a bipolar host and an uncharged co-host in a mixture, preferably together with an emitter or dopant. Bipolar host and uncharged co-host are selected such that the following conditions are applicable:

$$|HOMO(C)| - \min\{|HOMO(D)|; |HOMO(B)|\} > 0.3$$

$$|HOMO(B)| - |HOMO(D)| < 0.15 \text{ eV}$$

$$|LUMO(B)| - |LUMO(C)| > 0.3 \text{ eV}$$

$$|LUMO(B)| - |LUMO(D)| > 0,$$

where HOMO(C) is the HOMO energy of the uncharged co-host, HOMO(B) and HOMO(D) are correspondingly the HOMO energy of the bipolar host and of the dopant, LUMO(C), LUMO(B) and LUMO(D) are correspondingly the LUMO energy of the uncharged co-host, of the bipolar host and of the dopant, and the function $\min\{|HOMO(D)|; |HOMO(B)|\}$ gives the smaller of the two values $|HOMO(D)|$ and $|HOMO(B)|$.

Also described is the production of the OLED designated E21 which comprises, in the emitting layer, the host materials compound 9a, compound 13e and the yellow-phosphorescing emitter 13j. The structures of the compounds used are shown below:

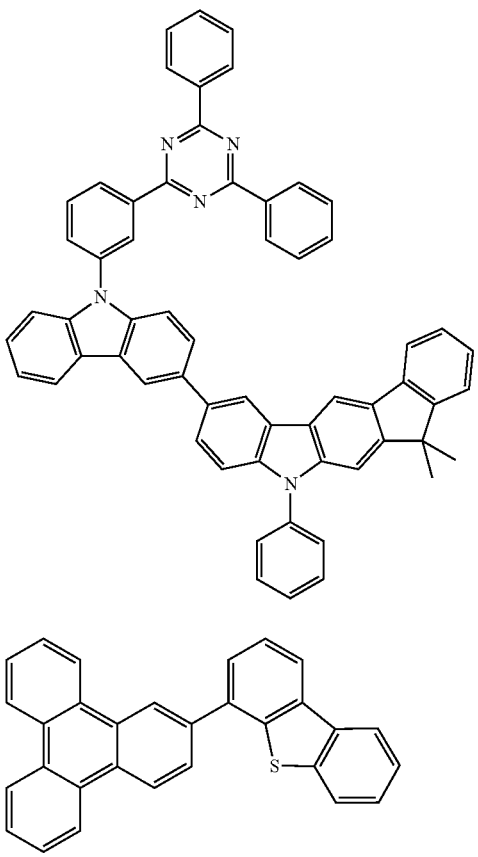

9a

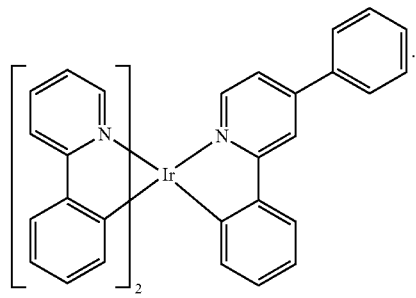

13j

However, in the case of the combination of bipolar compounds with uncharged co-host materials, there is still need for improvement, especially in relation to the lifetime of the organic electronic device, especially in the case of use in combination with green-phosphorescing emitters.

The problem addressed by the present invention was therefore that of providing materials which are suitable for use in an organic electronic device, especially in an organic electroluminescent device, and especially in a green-phosphorescing OLED, and lead to good device properties, especially with regard to an improved lifetime, and that of providing the corresponding electronic device.

13e

It has now been found that this problem is solved and the disadvantages from the prior art are eliminated by compositions comprising bipolar compounds of the formula (1) and triphenylene compounds of the formula (2). Compositions of this kind lead to very good properties of organic electronic devices, especially organic electroluminescent devices, especially with regard to lifetime and especially also in the presence of a light-emitting component in the emission layer at concentrations between 2% and 15% by weight, especially in the case of a green light-emitting component in the emission layer.

The present invention therefore firstly provides a composition comprising at least one compound of the formula (1) and at least one compound of the formula (2)

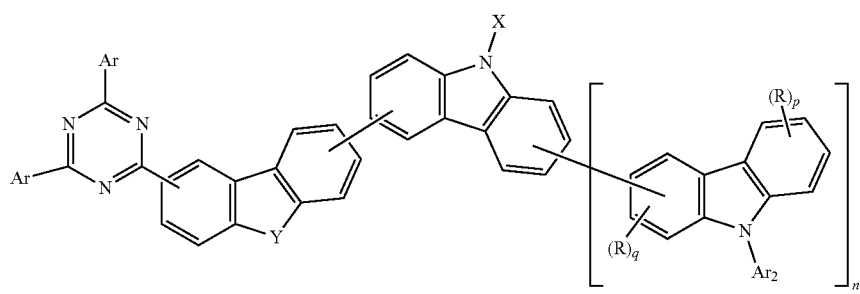

formula (1)

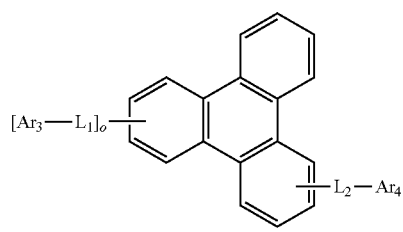

formula (2)

where the symbols and indices used are as follows:

X is the same or different at each instance and is $Ar_1$ or a substituent of the formula (1-1)

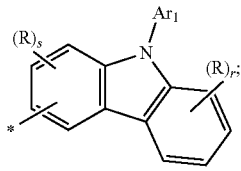

formula (1-1)

Y is O or S;

Ar, $Ar_1$, $Ar_2$ are each independently at each instance an aryl or heteroaryl group which has 5 to 40 ring atoms and may be substituted by one or more $R^3$ radicals or an aromatic or heteroaromatic ring system which has 6 to 40 ring atoms and may be substituted by one or more $R^3$ radicals;

n is 0 or 1;

p, q are each independently 0, 1, 2, 3 or 4;

s, r are each independently 0, 1, 2, 3 or 4;

* is the attachment site to the nitrogen atom;

R is the same or different at each instance and is selected from the group consisting of D, F, Cl, Br, I, CN, $NO_2$, $N(Ar)_2$, $N(R^2)_2$, $C(=O)Ar$, $C(=O)R^2$, $P(=O)(Ar)_2$, $P(Ar)_2$, $B(Ar)_2$, $Si(Ar)_3$, $Si(R^2)$, a straight-chain alkyl, alkoxy or thioalkyl group having 1 to 20 carbon atoms or a branched or cyclic alkyl, alkoxy or thioalkyl group having 3 to 20 carbon atoms or an alkenyl group having 2 to 20 carbon atoms, each of which may be substituted by one or more $R^2$ radicals, where one or more nonadjacent $CH_2$ groups may be replaced by $R^2C=CR^2$, $Si(R^2)_2$, $C=O$, $C=S$, $C=NR^2$, $P(=O)(R^2)$, $SO$, $SO_2$, $NR^2$, O, S or $CONR^2$ and where one or more hydrogen atoms may be replaced by D, F, Cl, Br, I, CN or $NO_2$, an aromatic or heteroaromatic ring system which has 5 to 40 ring atoms and may be substituted in each case by one or more $R^2$ radicals, an aryloxy or heteroaryloxy group which has 5 to 40 ring atoms and may be substituted by one or more $R^2$ radicals, or an aralkyl or heteroaralkyl group which has 5 to 40 ring atoms and may be substituted by one or more $R^2$ radicals; at the same time, it is possible here for not more than one R substituent together with $Ar_1$ to form a monocyclic or polycyclic aliphatic, aromatic or heteroaromatic ring system which may be substituted by one or more $R^2$ radicals;

o is 0 or 1;

$L_1$, $L_2$ are the same or different at each instance and are a single bond or an aromatic or heteroaromatic ring system which has 5 to 30 ring atoms and may be substituted by one or more $R^3$ radicals;

$Ar_3$ and $Ar_4$ are each independently an aromatic or heteroaromatic ring system which has 6 to 40 ring atoms and may be substituted by one or more $R^1$ radicals;

$R^1$ is the same or different at each instance and is selected from the group consisting of H, D, F, Cl, Br, I, CN, $NO_2$, $N(Ar)_2$, $N(R^2)_2$, $C(=O)Ar$, $C(=O)R^2$, $P(=O)(Ar)_2$, $P(Ar)_2$, $B(Ar)_2$, $Si(Ar)_3$, $Si(R^2)_3$, a straight-chain alkyl, alkoxy or thioalkyl group having 1 to 20 carbon atoms or a branched or cyclic alkyl, alkoxy or thioalkyl group having 3 to 20 carbon atoms or an alkenyl group having 2 to 20 carbon atoms, each of which may be substituted by one or more $R^2$ radicals, where one or more nonadjacent $CH_2$ groups may be replaced by $R^2C=CR^2$, $Si(R^2)_2$, $C=O$, $C=S$, $C=NR^2$, $P(=O)(R^2)$, $SO$, $SO_2$, $NR^2$, O, S or $CONR^2$ and where one or more hydrogen atoms may be replaced by D, F, Cl, Br, I, CN or $NO_2$, an aromatic or heteroaromatic ring system which has 5 to 40 ring atoms and may be substituted in each case by one or more $R^2$ radicals, an aryloxy or heteroaryloxy group which has 5 to 40 ring atoms and may be substituted by one or more $R^2$ radicals, or an aralkyl or heteroaralkyl group which has 5 to 40 ring atoms and may be substituted by one or more $R^2$ radicals; at the same time, it is optionally possible for two substituents $R^1$ bonded to the same carbon atom or to adjacent carbon atoms to form a monocyclic or polycyclic, aliphatic, aromatic or heteroaromatic ring system which may be substituted by one or more $R^2$ radicals;

$R^2$ is the same or different at each instance and is selected from the group consisting of H, D, F, Cl, Br, I, CN, $NO_2$, $N(Ar)_2$, $NH_2$, $N(R^3)_2$, $C(=O)Ar$, $C(=O)H$, $C(=O)R^3$, $P(=O)(Ar)_2$, a straight-chain alkyl, alkoxy or thioalkyl group having 1 to 40 carbon atoms or a branched or cyclic alkyl, alkoxy or thioalkyl group having 3 to 40 carbon atoms or an alkenyl or alkynyl group having 2 to 40 carbon atoms, each of which may be substituted by one or more $R^3$ radicals, where one or more nonadjacent $CH_2$ groups may be replaced by $HC=CH$, $R^3C=CR^3$, $C≡C$, $Si(R^3)_2$, $Ge(R^3)_2$, $Sn(R^3)_2$, $C=O$, $C=S$, $C=Se$, $C=NR^3$, $P(=O)(R^3)$, $SO$, $SO_2$, $NH$, $NR^3$, O, S, $CONH$ or $CONR^3$ and where one or more hydrogen atoms may be replaced by D, F, Cl, Br, I, CN or $NO_2$, an aromatic or heteroaromatic ring system which has 5 to 60 ring atoms and may be substituted in each case by one or more $R^3$ radicals, an aryloxy or heteroaryloxy group which has 5 to 60 ring atoms and may be substituted by one or more $R^3$ radicals, or a combination of these systems; where it is optionally possible for two or more adjacent substituents $R^2$ to form a monocyclic or polycyclic, aliphatic, aromatic or heteroaromatic ring system which may be substituted by one or more $R^3$ radicals;

$R^3$ is the same or different at each instance and is selected from the group consisting of H, D, F, CN, an aliphatic hydrocarbyl radical having 1 to 20 carbon atoms, or an aromatic or heteroaromatic ring system having 5 to 30 ring atoms in which one or more hydrogen atoms may be replaced by D, F, Cl, Br, I or CN and which may be substituted by one or more alkyl groups each having 1 to 4 carbon atoms; at the same time, it is possible for two or more adjacent substituents $R^3$ together to form a mono- or polycyclic, aliphatic ring system.

The invention further provides formulations comprising compositions of this kind, for the use of these compositions in an organic electronic device, organic electronic devices, preferably electroluminescent devices, comprising compositions of this kind and preferably comprising the composition in one layer, and processes for producing devices of this kind. The corresponding preferred embodiments as described hereinafter likewise form part of the subject-matter of the present invention. The surprising and advantageous effects are achieved through specific selection of known materials, especially with regard to the selection of the bipolar materials of the formula (1).

The layer comprising the composition comprising at least one compound of the formula (1) and at least one compound of the formula (2) as described above or described as preferred hereinafter is especially an emitting layer (EML), an electron transport layer (ETL), an electron injection layer (EIL) and/or a hole blocker layer (HBL).

When the layer is an emitting layer, it is preferably a phosphorescent layer which is characterized in that it comprises, in addition to the composition comprising the matrix materials of the formula (1) and formula (2) as described above, a phosphorescent emitter, especially preferably a green-phosphorescent emitter.

Adjacent carbon atoms in the context of the present invention are carbon atoms bonded directly to one another.

The wording that two or more radicals together may form a ring, in the context of the present description, shall be understood to mean, inter alia, that the two radicals are joined to one another by a chemical bond with formal elimination of two hydrogen atoms. This is illustrated by the following scheme:

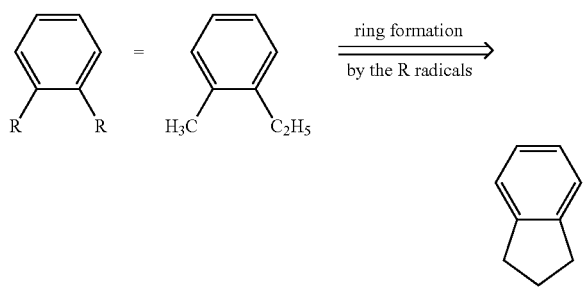

In addition, however, the abovementioned wording shall also be understood to mean that, if one of the two radicals is hydrogen, the second radical binds to the position to which the hydrogen atom was bonded, forming a ring. This shall be illustrated by the following scheme:

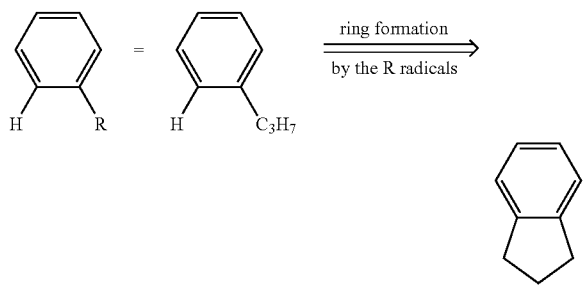

An aryl group in the context of this invention contains 6 to 40 aromatic ring atoms, preferably carbon atoms. A heteroaryl group in the context of this invention contains 5 to 40 aromatic ring atoms, where the ring atoms include carbon atoms and at least one heteroatom, with the proviso that the sum total of carbon atoms and heteroatoms adds up to at least 5. The heteroatoms are preferably selected from N, O and/or S. An aryl group or heteroaryl group is understood here to mean either a simple aromatic cycle, i.e. phenyl, derived from benzene, or a simple heteroaromatic cycle, for example derived from pyridine, pyrimidine or thiophene, or a fused aryl or heteroaryl group, for example naphthalene, anthracene, phenanthrene, quinoline or isoquinoline.

An aromatic ring system in the context of this invention contains 6 to 40 carbon atoms in the ring system and may be substituted by one or more $R^3$ radicals, where $R^3$ has a definition described below. An aromatic ring system also includes aryl groups as described above.

A heteroaromatic ring system in the context of this invention contains 5 to 40 ring atoms and at least one heteroatom and may be substituted by one or more $R^3$ radicals, where $R^3$ has a definition described below. A preferred heteroaromatic ring system has 10 to 40 ring atoms and at least one heteroatom and may be substituted by one or more $R^3$ radicals, where $R^3$ has a definition described below. A heteroaromatic ring system also includes heteroaryl groups as described above. The heteroatoms in the heteroaromatic ring system are preferably selected from N, O and/or S.

An aromatic or heteroaromatic ring system in the context of this invention is understood to mean a system which does not necessarily contain only aryl or heteroaryl groups, but in which it is also possible for a plurality of aryl or heteroaryl groups to be interrupted by a nonaromatic unit (preferably less than 10% of the atoms other than H), for example a carbon, nitrogen or oxygen atom or a carbonyl group. For example, systems such as 9,9'-spirobifluorene, 9,9-diarylfluorene, triarylamine, diaryl ethers, stilbene, etc. shall thus also be regarded as aromatic or heteroaromatic ring systems in the context of this invention, and likewise systems in which two or more aryl groups are interrupted, for example, by a linear or cyclic alkyl group or by a silyl group. In addition, systems in which two or more aryl or heteroaryl groups are bonded directly to one another, for example biphenyl, terphenyl, quaterphenyl or bipyridine, are likewise encompassed by the definition of the aromatic or heteroaromatic ring system.

An aromatic or heteroaromatic ring system which has 5-40 ring atoms and may also be substituted in each case by the abovementioned $R^3$ radicals and which may be joined to the aromatic or heteroaromatic system via any desired positions is understood to mean, for example, groups derived from benzene, naphthalene, anthracene, benzanthracene, phenanthrene, benzophenanthrene, pyrene, chrysene, perylene, fluoranthene, benzofluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, cis- or trans-monobenzoindenofluorene, cis- or trans-dibenzoindenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

A cyclic alkyl, alkoxy or thioalkyl group in the context of this invention is understood to mean a monocyclic, bicyclic or polycyclic group.

In the context of the present invention, a $C_1$- to $C_{20}$-alkyl group in which individual hydrogen atoms or $CH_2$ groups may also be substituted by the abovementioned groups is understood to mean, for example, the methyl, ethyl, n-propyl, i-propyl, cyclopropyl, n-butyl, i-butyl, s-butyl, t-butyl, cyclobutyl, 2-methylbutyl, n-pentyl, s-pentyl, t-pentyl, 2-pentyl, neopentyl, cyclopentyl, n-hexyl, s-hexyl, t-hexyl, 2-hexyl, 3-hexyl, neohexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]octyl, 2-(2,6-dimethyl)octyl, 3-(3,7-dimethyl)octyl, adamantyl, trifluoromethyl, pentafluoroethyl, 2,2,2-trifluoroethyl, 1,1-dimethyl-n-hex-1-yl, 1,1-dimethyl-n-hept-1-yl, 1,1-dimethyl-n-oct-1-yl, 1,1-dimethyl-n-dec-1-yl, 1,1-dimethyl-n-dodec-1-yl, 1,1-dimethyl-n-tetradec-1-yl, 1,1-dimethyl-n-hexadec-1-yl, 1,1-dimethyl-n-octadec-1-yl, 1,1-diethyl-n-hex-1-yl, 1,1-diethyl-n-hept-1-yl, 1,1-diethyl-n-oct-1-yl, 1,1-diethyl-n-dec-1-yl, 1,1-diethyl-n-dodec-1-yl, 1,1-diethyl-n-tetradec-1-yl, 1,1-diethyl-n-hexadec-1-yl, 1,1-diethyl-n-octadec-1-yl, 1-(n-propyl)cyclohex-1-yl, 1-(n-butyl)cyclohex-1-yl, 1-(n-hexyl)cyclohex-1-yl, 1-(n-octyl)cyclohex-1-yl and 1-(n-decyl)cyclohex-1-yl radicals.

An alkenyl group is understood to mean, for example, ethenyl, propenyl, butenyl, pentenyl, cyclopentenyl, hexenyl, cyclohexenyl, heptenyl, cycloheptenyl, octenyl, cyclooctenyl or cyclooctadienyl.

An alkynyl group is understood to mean, for example, ethynyl, propynyl, butynyl, pentynyl, hexynyl, heptynyl or octynyl.

A $C_1$- to $C_{20}$-alkoxy group is understood to mean, for example, methoxy, trifluoromethoxy, ethoxy, n-propoxy, i-propoxy, n-butoxy, i-butoxy, s-butoxy, t-butoxy or 2-methylbutoxy.

A $C_1$- to $C_{20}$-thioalkyl group is understood to mean, for example S-alkyl groups, for example thiomethyl, 1-thioethyl, 1-thio-i-propyl, 1-thio-n-propyl, 1-thio-i-butyl, 1-thio-n-butyl or 1-thio-t-butyl.

An aryl or heteroaryloxy group having 5 to 40 ring atoms means O-aryl or O-heteroaryl and means that the aryl or heteroaryl group is bonded via an oxygen atom.

An aralkyl or heteroaralkyl group having 5 to 40 ring atoms means that an alkyl group as described above is substituted by an aryl group or heteroaryl group.

A phosphorescent emitter in the context of the present invention is a compound that exhibits luminescence from an excited state with higher spin multiplicity, i.e. a spin state >1, especially from an excited triplet state. In the context of this application, all luminescent complexes with transition metals or lanthanides are to be regarded as phosphorescent emitters. A more exact definition is given further down.

When the composition comprising at least one compound of the formula (1) as described above or described as preferred hereinafter and at least one compound of the formula (2) as described above or described as preferred hereinafter is used as matrix material for a phosphorescent emitter, it is preferable when the triplet energy thereof is not significantly less than the triplet energy of the phosphorescent emitter. In respect of the triplet level, it is preferably the case that $T_1$(emitter)–$T_1$(matrix)≤0.2 eV, more preferably ≤0.15 eV, most preferably ≤0.1 eV. $T_1$(matrix) here is the triplet level of the matrix material in the emission layer, this condition being applicable to each of the two matrix materials, and $T_1$(emitter) is the triplet level of the phosphorescent emitter. If the emission layer contains more than two matrix materials, the abovementioned relationship is preferably also applicable to every further matrix material. The expression "dopant" is used synonymously with emitter hereinafter.

It is particularly advantageous with regard to the performance data and lifetime of electronic devices when the components of the composition fulfil the following conditions:

|HOMO(C)|−min{|HOMO(D)|;|HOMO(B)|}>0.3

||HOMO(B)|−|HOMO(D)||<0.15 eV

||LUMO(B)|−|LUMO(C)||>0.3 eV

||LUMO(B)|−|LUMO(D)||>0, where HOMO(C) is the HOMO energy of the uncharged co-host, HOMO(B) and HOMO(D) are correspondingly the HOMO energy of the bipolar host and of the dopant, LUMO(C), LUMO(B) and LUMO(D) are correspondingly the LUMO energy of the uncharged co-host, of the bipolar host and of the dopant, and the function min{|HOMO(D)|; |HOMO(B)|} gives the smaller of the two values |HOMO (D)| and |HOMO(B)|, and where |HOMO| and |LUMO| are the absolute magnitude of the respective value.

The energy values reported relate to isolated compounds and are ascertained as set out hereinafter.

The HOMO (highest occupied molecular orbital) and LUMO (lowest unoccupied molecular orbital) energies and the triplet level of the materials are determined via quantum-chemical calculations. For this purpose, in the present case, the "Gaussian09, Revision D.01" software package (Gaussian Inc.) is used. It is alternatively possible to use other software packages provided that the same methods have been implemented therein. For calculation of organic substances without metals (referred to as the "org." method), a geometry optimization is first conducted by the semi-empirical method AM1 (Gaussian input line "#AM1 opt") with charge 0 and multiplicity 1. Subsequently, on the basis of the optimized geometry, a (single-point) energy calculation is effected for the electronic ground state and the triplet level. This is done using the TDDFT (Time Dependent Density Functional Theory) method B3PW91 with the 6-31G(d) basis set (Gaussian input line "#B3PW91/6-31G(d) td=(50-50,nstates=4)") (charge 0, multiplicity 1). For organometallic compounds (referred to as the "M-org." method), the geometry is optimized by the Hartree-Fock method and the LanL2 MB basis set (Gaussian input line "#HF/LanL2 MB opt") (charge 0, multiplicity 1). The energy calculation is effected, as described above, analogously to the organic substances, as described above, except that the "LanL2DZ" basis set is used for the metal atom and the "6-31G(d)" basis set for the ligands (Gaussian input line "#B3PW91/gen pseudo=lanl2 td=(50-50,nstates=4)"). From the energy calculation, the HOMO is obtained as the last orbital occupied by two electrons (alpha occ. eigenvalues) and LUMO as the first unoccupied orbital (alpha virt. eigenvalues) in Hartree units (HEh and LEh). This is used to determine the HOMO and LUMO value in electron volts, calibrated by cyclic voltammetry measurements, as follows:

LUMO(eV)=(1.0658*LEh*27.212)−0.5049

HOMO(eV)=(0.8308*HEh*27.212)−1.1180

These values are to be regarded as HOMO and as LUMO of the materials in the context of this application.

The triplet level $T_1$ of a material is defined as the relative excitation energy (in eV) of the triplet state having the lowest energy which is found by the quantum-chemical energy calculation.

The abovementioned conditions and the method of determining the individual energy values permit the person skilled in the art in this field to identify the suitable compounds from the prior art in a simple manner. The calculation of orbital energies is a routine activity for the person skilled in the art, who is able to do so with the aid of the abovementioned method within a short period of time.

The person skilled in the art will be aware that a bipolar host is one which, in the mixture used, makes a significant contribution both to electron transport and to hole transport in the component used. The person skilled in the art will further be aware that this can be achieved by selecting a material (a) into which both electrons and holes are injected to a significant degree owing to its energy levels by comparison with the energy levels of further materials used in the same mixture, and (b) in which transport is not suppressed owing to extremely low electron or hole mobility (less than $10^{-8}$ cm$^2$/(Vs)). The measurement of electron and hole mobilities is conducted in a routine manner by the person skilled in the art by means of standard methods.

Bipolar Hosts of the Formula (1):

In one embodiment of the invention, compounds of the formula (1) in which Y is selected from O and S and the substituent

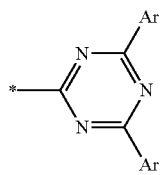

is bonded in position 1, 2, 3 or 4 of the dibenzofuran or dibenzothiophene are selected, where X, Ar, Ar$_1$, Ar$_2$, R, n, p, q, r and s have a definition given above or have a definition given hereinafter and * indicates the bonding site to the dibenzofuran or dibenzothiophene.

Preferably, Y is O.

The symbol X in compounds of the formula (1) as described above or described as preferred is either Ar$_1$ or a substituent of the formula (1-1) where Ar$_1$, Ar$_2$, R, n, p, q, r and s have an aforementioned definition or one specified hereinafter as preferred.

Compounds of the formula (1) in which X is Ar$_1$ and n is 1 are represented by the formula (1a)

where Y, Ar, Ar$_1$, Ar$_2$, R, p and q have a definition given above or a definition given hereinafter.

Compounds of the formula (1) in which X is a substituent of the formula (1-1) and n is 0 are represented by the formula (1b)

formula (1b)

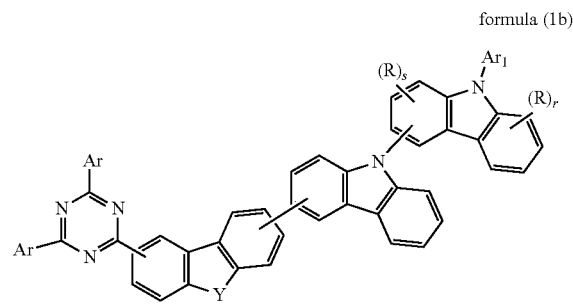

where Y, Ar, Ar$_1$, Ar$_2$, R, p and q have a definition given above or a definition given hereinafter.

Preferably, at least one compound of the formula (1a) having substituents described above or described hereinafter as preferred is selected for the composition.

Preferably, at least one compound of the formula (1b) having substituents described above or described hereinafter as preferred is selected for the composition.

The invention accordingly further provides a composition as described above, where the compound of the formula (1) corresponds to the compound of the formula (1a) or (1b).

In one embodiment of the invention, compounds of the formula (1), (1a) or (1b) in which Y is selected from O and S and the substituent

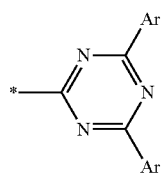

is bonded in position 1, 2, 3 or 4 of the dibenzofuran or dibenzothiophene and the carbazole unit is bonded in position 6, 7, 8 or 9 of the dibenzofuran or dibenzothiophene are selected, where Y, X, Ar, Ar$_1$, Ar$_2$, R, n, p, q, r and have a definition given above or have a definition given hereinafter and * indicates the bonding site to the dibenzofuran or dibenzothiophene.

formula (1a)

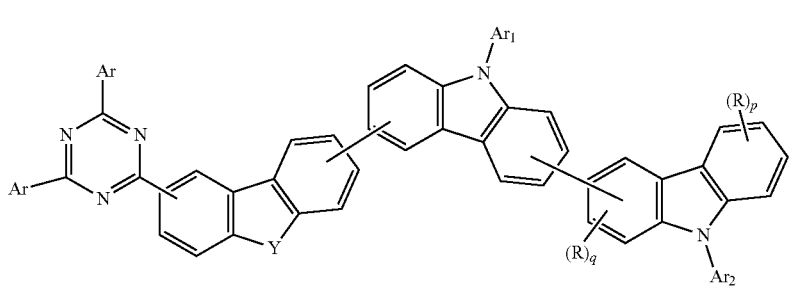

It is further preferable when the carbazole unit is bonded in position 7 or 8 of the dibenzofuran or dibenzothiophene.

More preferably, accordingly, a compound of the formula (1), (1a) or (1b) in which the carbazole unit is bonded in position 7 or 8 of the dibenzofuran or dibenzothiophene is selected for the composition.

In this embodiment, compounds of the formula (1c), (1d), (1e) or (1f) are preferably selected for the composition where Y, Ar, $Ar_1$, $Ar_2$, R, p, q, r and s have a definition given above or a definition given hereinafter.

It is further preferable when the dibenzofuran or dibenzothiophene unit is bonded in position 3 of the carbazole.

More preferably, accordingly, a compound of the formula (1), (1a), (1b), (1c), (1d), (1e) or (1f) in which the dibenzofuran or dibenzothiophene unit is bonded in position 3 of the carbazole is selected for the composition.

formula (1c)

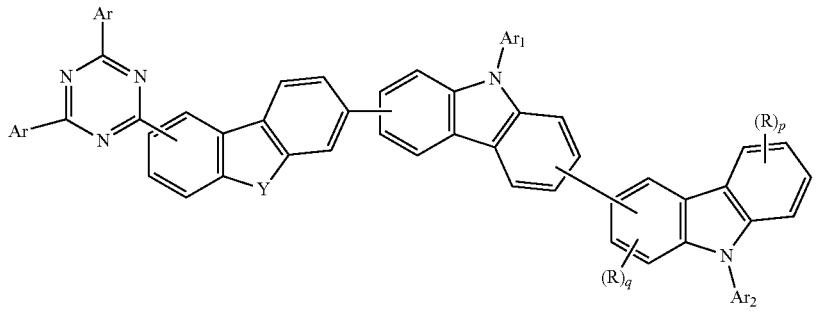

formula (1d)

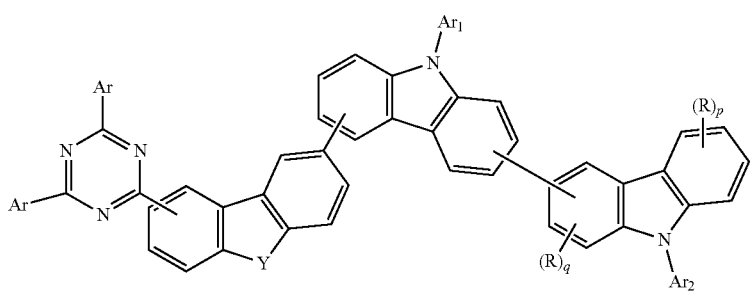

formula (1e)

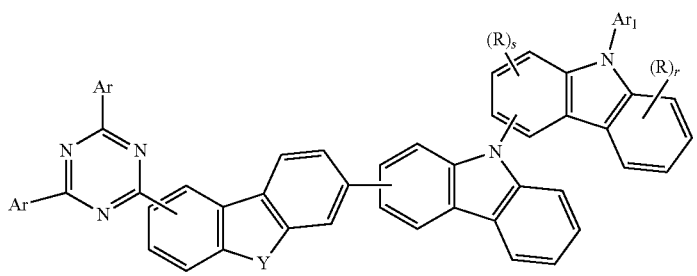

formula (1f)

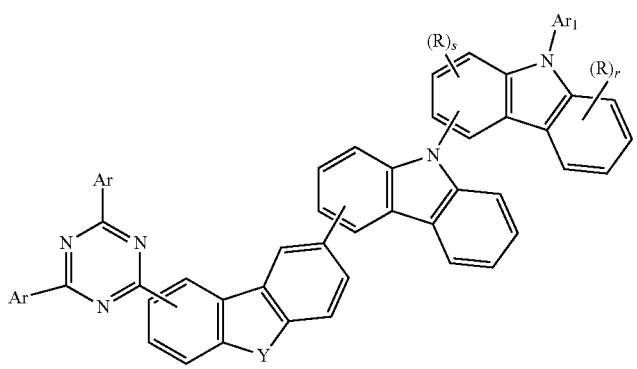

In this embodiment, compounds of the formula (1g), (1h), (1i) or (1j) are preferably selected for the composition or (1j) described as preferred, Ar₁ or Ar₂ as described above or described as preferred is an aryl group substituted by one

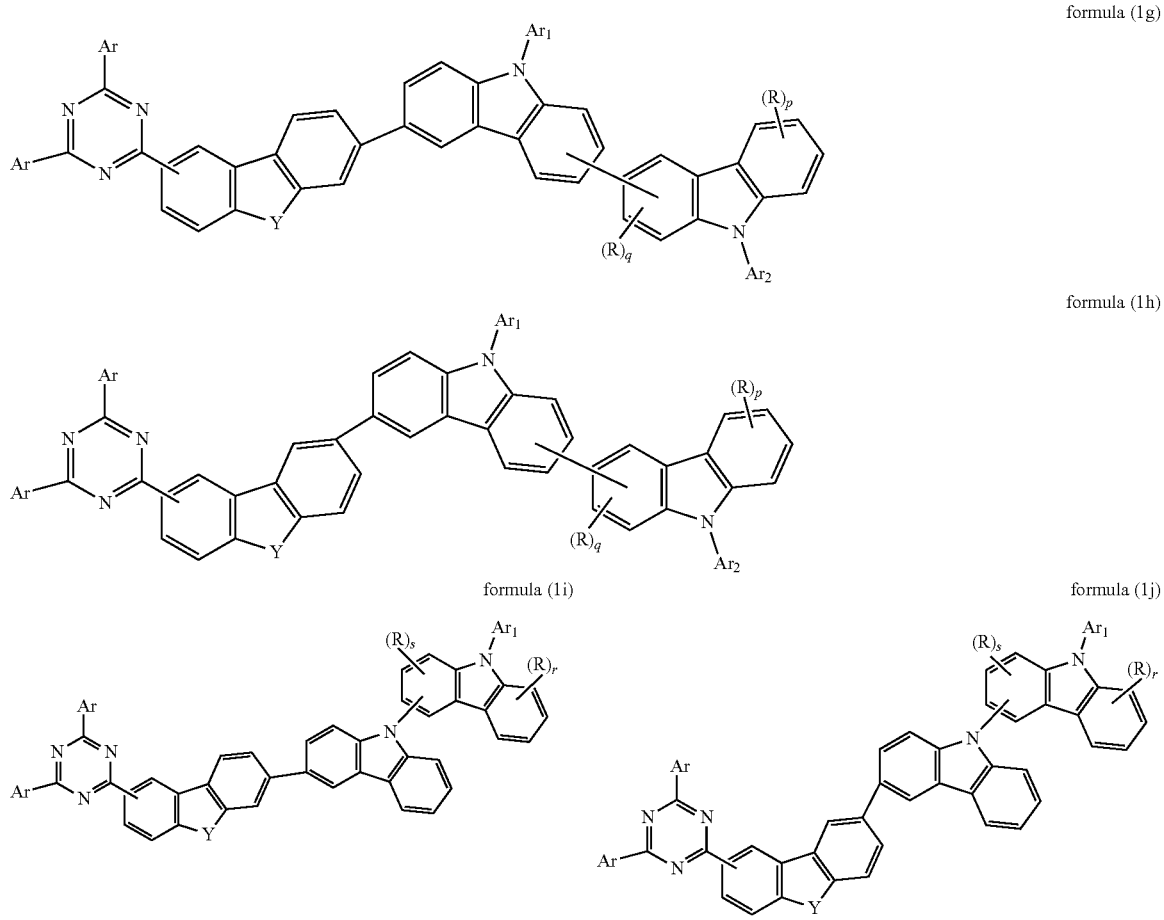

formula (1g)

formula (1h)

formula (1i)

formula (1j)

where Y, Ar, Ar₁, Ar₂, R, p, q, r and s have a definition given above or a definition given hereinafter.

In compounds of the formula (1), (1a), (1b), (1c), (1d), (1e), (1f), (1g), (1h), (1i) or (1j), or compounds of the formula (1), (1a), (1b), (1c), (1d), (1e), (1f), (1g), (1h), (1i) or (1j) described as preferred, Ar is in each case independently preferably an aryl group having 6 to 40 carbon atoms as described above or described as preferred, which may be substituted by one or more R³ radicals. More preferably, at least one Ar is phenyl and the other aromatic Ar substituent is an aryl group which has 6 to 40 carbon atoms and may be substituted by one or more R³ radicals. More preferably, both Ar groups are phenyl.

In compounds of the formula (1), (1a), (1b), (1c), (1d), (1e), (1f), (1g), (1h), (1i) or (1j), or compounds of the formula (1), (1a), (1b), (1c), (1d), (1e), (1f), (1g), (1h), (1i) or (1j) described as preferred, Ar₁ and Ar₂ are each independently preferably an aryl group having 6 to 40 carbon atoms as described above or described as preferred, which may be substituted by one or more R³ radicals. More preferably, Ar₁ and Ar₂ are each independently phenyl or naphthyl, each of which may be substituted by one or more R³ radicals.

When, in compounds of the formula (1), (1a), (1b), (1c), (1d), (1e), (1f), (1g), (1h), (1i) or (1j), or compounds of the formula (1), (1a), (1b), (1c), (1d), (1e), (1f), (1g), (1h), (1i) or (1j) described as preferred, Ar₁ or Ar₂ as described above or described as preferred is an aryl group substituted by one or more R³ radicals, the substituent R³ is the same or different at each instance and is preferably selected from the group consisting of D, F, a straight-chain or branched alkyl group having 1 to 20 carbon atoms or an aromatic or heteroaromatic ring system having 5 to 40 ring atoms. The heteroaromatic ring system having 5 to 40 ring atoms for this/these substituent(s) R³ is preferably derived from dibenzofuran or dibenzothiophene. The aromatic ring system having 6 to 40 ring atoms for this/these substituent(s) R³ is preferably phenyl, biphenyl or terphenyl, more preferably phenyl. The straight-chain or branched alkyl group for this/these substituent(s) R³ is preferably methyl, ethyl, n-propyl or n-butyl, more preferably methyl.

In compounds of the formula (1), (1a), (1b), (1c), (1d), (1e), (1f), (1g), (1h), (1i) or (1j), or compounds of the formula (1), (1a), (1b), (1c), (1d), (1e), (1f), (1g), (1h), (1i) or (1j) described as preferred, p, q, r and s are each independently 0 or 1; more preferably, p and q are 0.

In compounds of the formula (1), (1a), (1c), (1d), (1g) or (1h) or compounds of the formula (1), (1a), (1c), (1d), (1g) or (1h) described as preferred, p and q are each independently preferably 0 or 1, where, in the case that p=1 and q=0 or q=1 and p=0, R together with the Ar₂ substituent preferably forms a monocyclic or polycyclic, aliphatic, aromatic or heteroaromatic ring system which may be substituted by one or more R² radicals. Preferably, the ring system that forms is unsubstituted.

Preferred examples for the formation of such a ring system are the substituents of the formulae (1-2), (1-3), (1-4), (1-5) and (1-6), preferably the substituents of the formulae (1-4), (1-5) and (1-6);

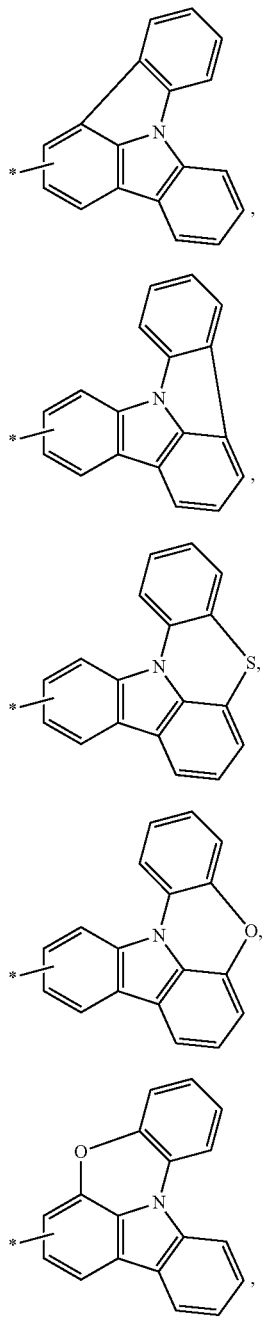

formula (1-2)

formula (1-3)

formula (1-4)

formula (1-5)

formula (1-6)

where the attachment site of this substituent is marked by * and is possible in position 5, 6, 7 or 8 of the carbazole unit.

In compounds of the formula (1), (1b), (1e), (1f), (1i) or (1j) or compounds of the formula (1), (1b), (1e), (1f), (1i) or (1j) described as preferred, r and s are each independently preferably 0 or 1, where, in the case that r=1 and s=0 or s=1 and r=0, R together with the $Ar_1$ substituent preferably forms a monocyclic or polycyclic, aliphatic, aromatic or heteroaromatic ring system which may be substituted by one or more $R^2$ radicals. Preferably, the ring system that forms is unsubstituted.

Preferred examples for the formation of such a ring system in the substituent of the formula (1-1) are the substituents of the formulae (1-2), (1-3), (1-4), (1-5) and (1-6), preferably of the formulae (1-2) and (1-3);

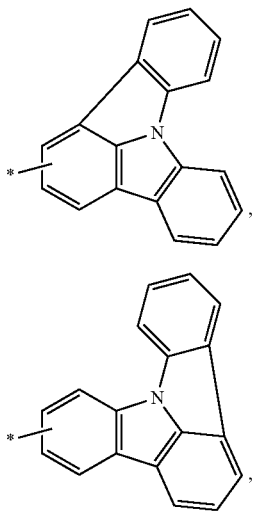

formula (1-2)

formula (1-3)

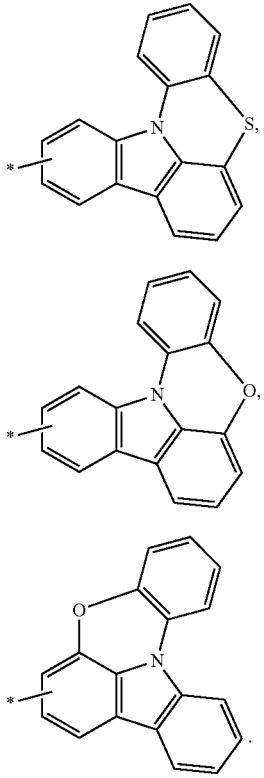

formula (1-4)

formula (1-5)

formula (1-6)

When, in compounds of the formula (1), (1a), (1b), (1c), (1d), (1e), (1f), (1g), (1h), (1i) or (1j), or compounds of the formula (1), (1a), (1b), (1c), (1d), (1e), (1f), (1g), (1h), (1i) or (1j) described as preferred, p, q, r and s are 1, the substituent R is the same or different at each instance and is preferably selected from the group consisting of D, F, an alkyl group having 1 to 20 carbon atoms or an aromatic or heteroaromatic ring system having 5 to 40 ring atoms. The heteroaromatic ring system having 5 to 40 ring atoms for this substituent R is preferably derived from dibenzofuran or dibenzothiophene. The aromatic ring system having 6 to 40 ring atoms for this substituent R is preferably derived from phenyl, biphenyl or terphenyl, more preferably phenyl. The alkyl group having 1 to 20 carbon atoms for this substituent R is preferably a linear or branched alkyl group having 1 to 4 carbon atoms, more preferably methyl, ethyl, n-propyl or n-butyl, most preferably methyl.

Examples of suitable compounds of the formula (1), (a), (1b), (1c), (1d), (1e), (1f), (1g), (1h), (1i) or (1j) that are selected in accordance with the invention are the structures shown below in Table 1.

TABLE 1

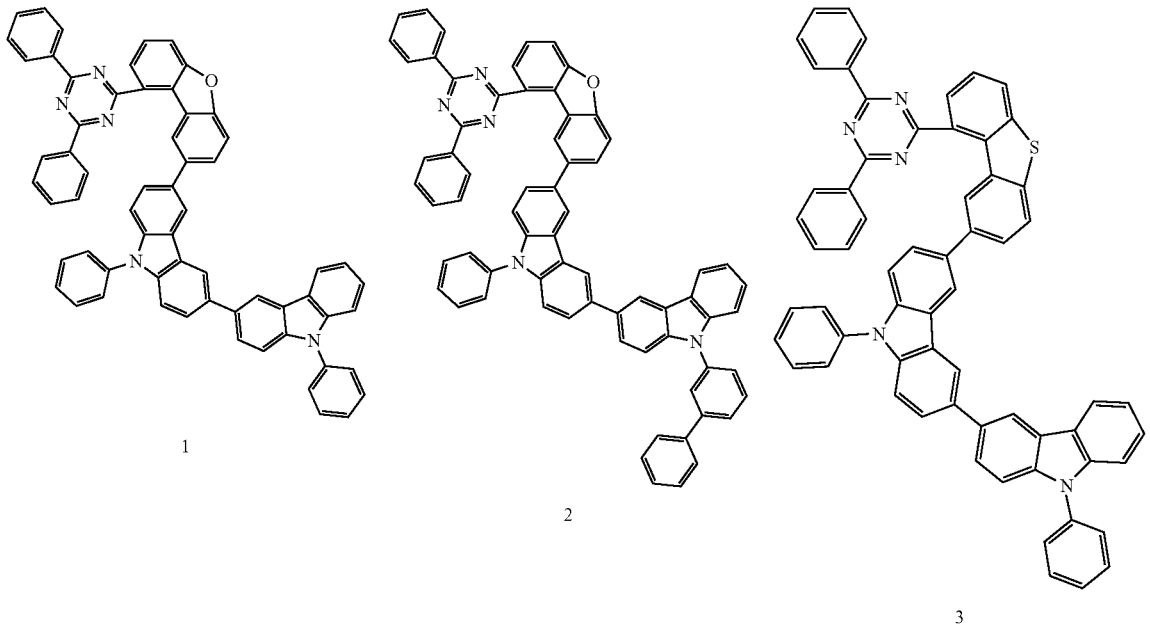

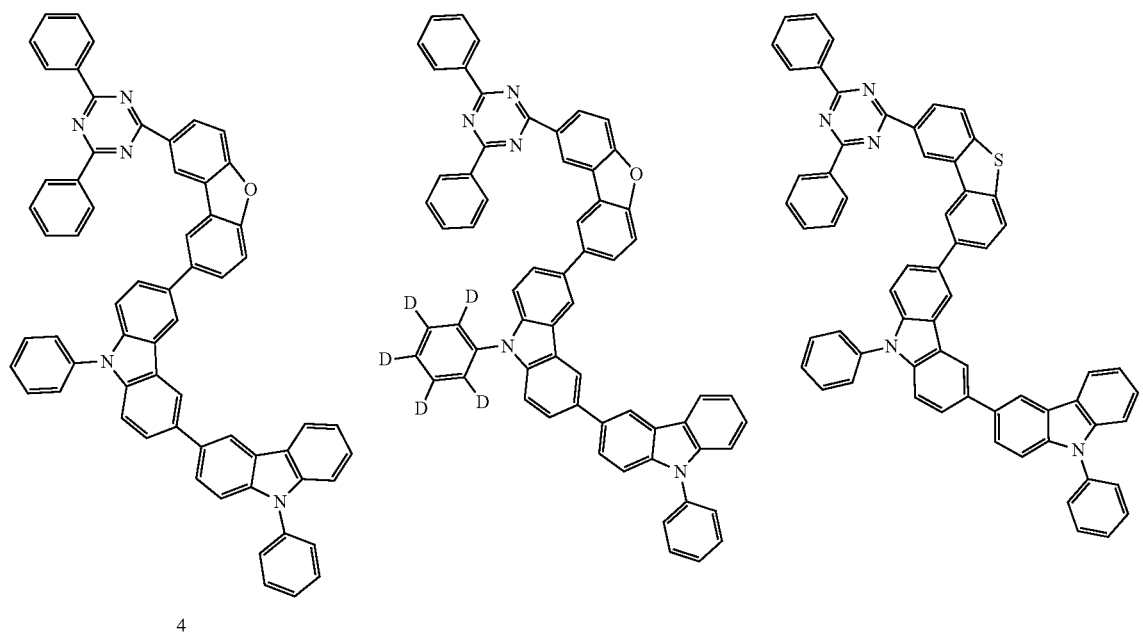

TABLE 1-continued
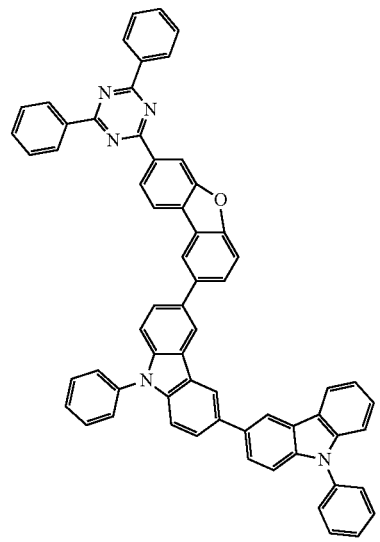 [SMILES: c1ccc(-c2nc(-c3ccccc3)nc(-c3ccc4c(c3)oc3ccc(-c5ccc6c(c5)c5cc(-c7ccc8c(c7)c7ccccc7n8-c7ccccc7)ccc5n6-c5ccccc5)cc34)n2)cc1]
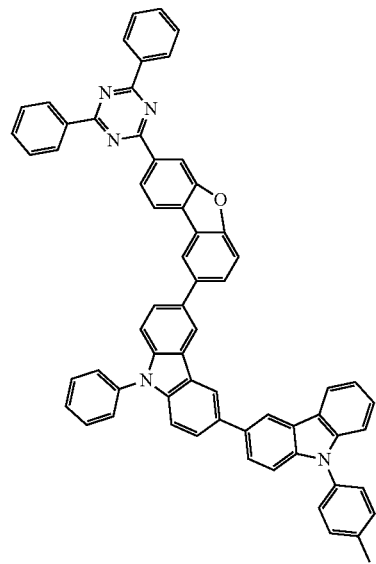 [SMILES: Cc1ccc(-n2c3ccccc3c3cc(-c4ccc5c(c4)c4cc(-c6ccc7oc8cc(-c9nc(-c%10ccccc%10)nc(-c%10ccccc%10)n9)ccc8c7c6)ccc4n5-c4ccccc4)ccc32)cc1]
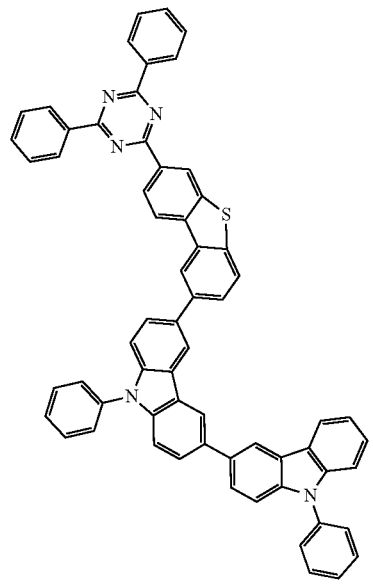 [SMILES: c1ccc(-c2nc(-c3ccccc3)nc(-c3ccc4c(c3)sc3ccc(-c5ccc6c(c5)c5cc(-c7ccc8c(c7)c7ccccc7n8-c7ccccc7)ccc5n6-c5ccccc5)cc34)n2)cc1]
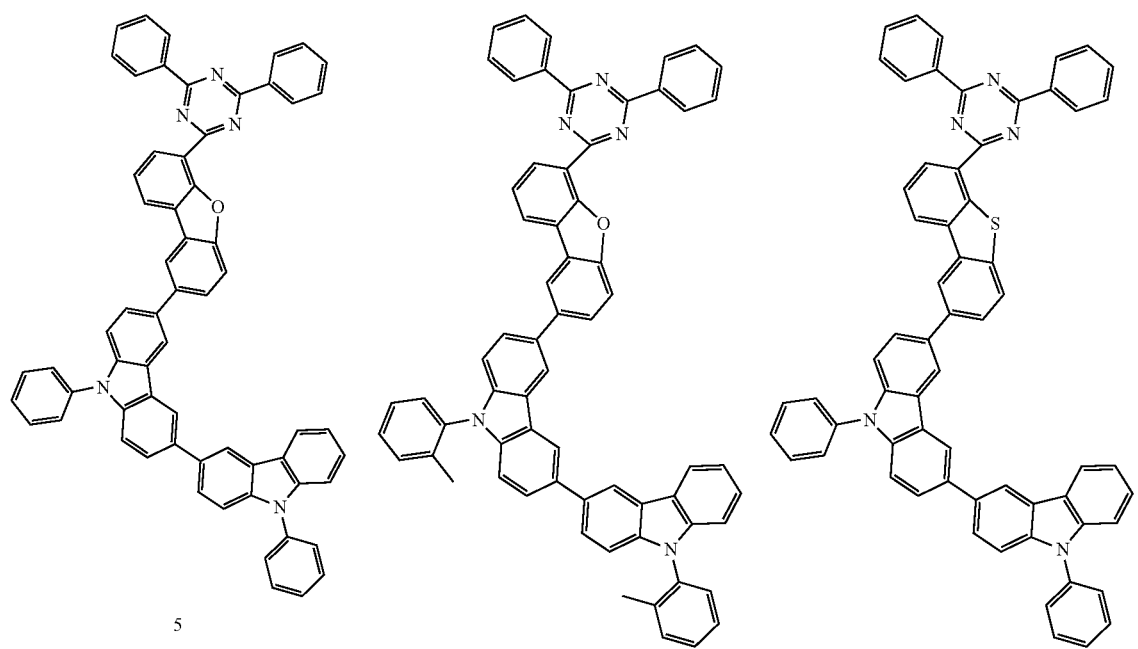

TABLE 1-continued
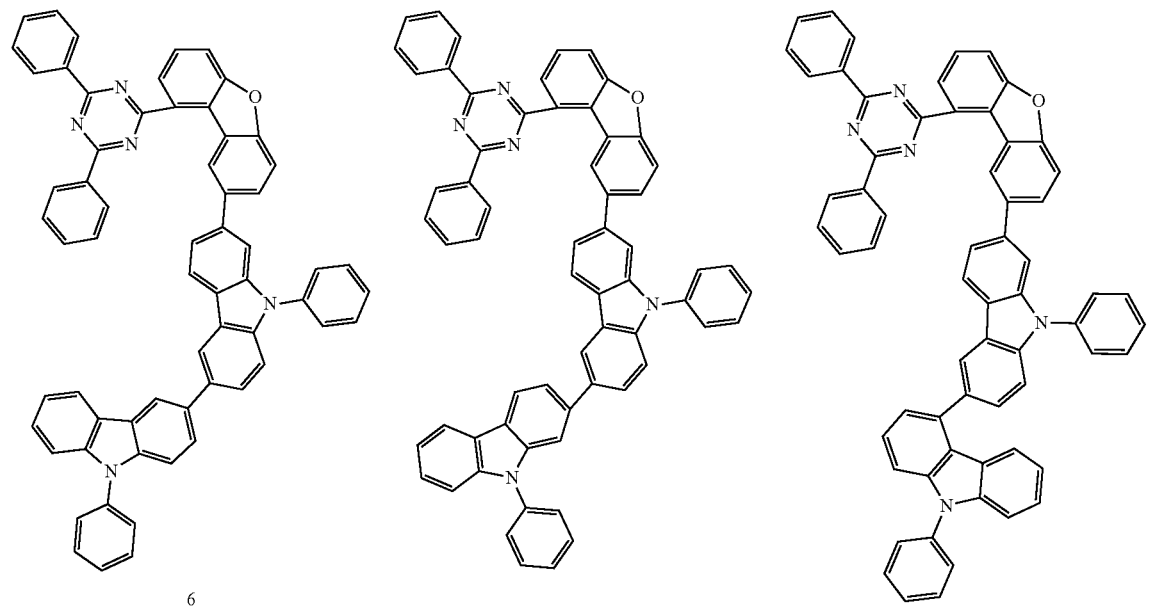
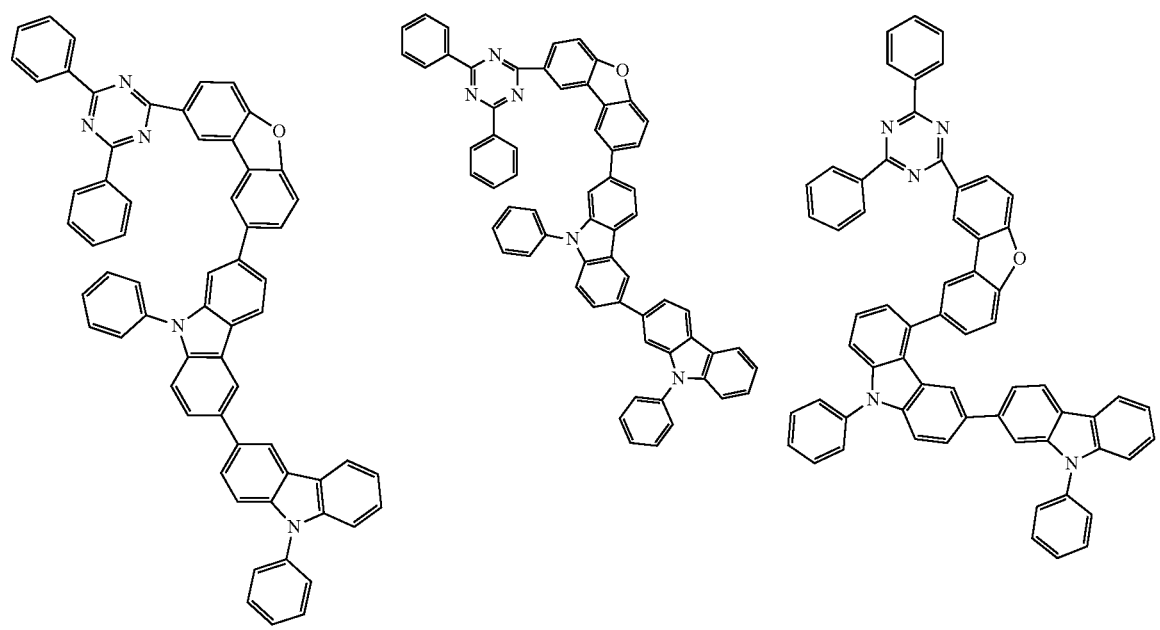

TABLE 1-continued
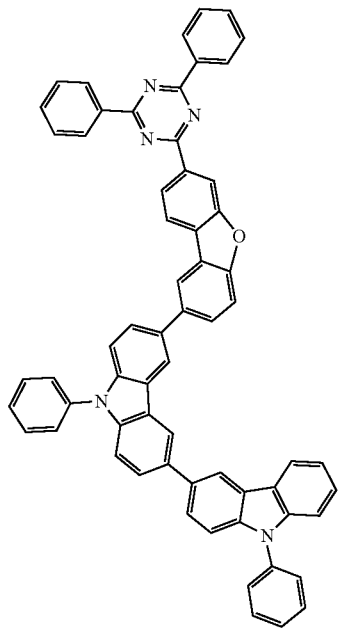 [SMILES: c1ccc(-c2nc(-c3ccccc3)nc(-c3ccc4c(c3)oc3ccc(-c5ccc6c(c5)c5cc(-c7ccc8c(c7)c7ccccc7n8-c7ccccc7)ccc5n6-c5ccccc5)cc34)n2)cc1] 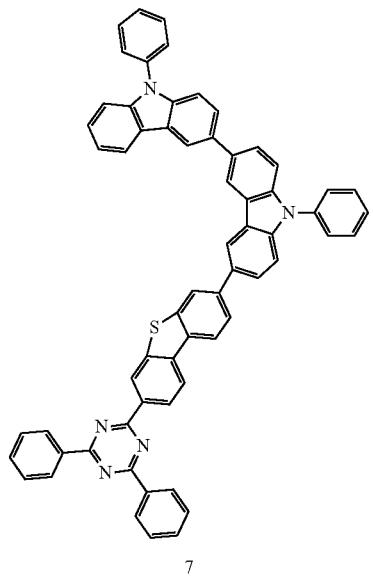 [SMILES: c1ccc(-c2nc(-c3ccccc3)nc(-c3ccc4c(c3)sc3cc(-c5ccc6c(c5)c5cc(-c7ccc8c(c7)c7ccccc7n8-c7ccccc7)ccc5n6-c5ccccc5)ccc34)n2)cc1] 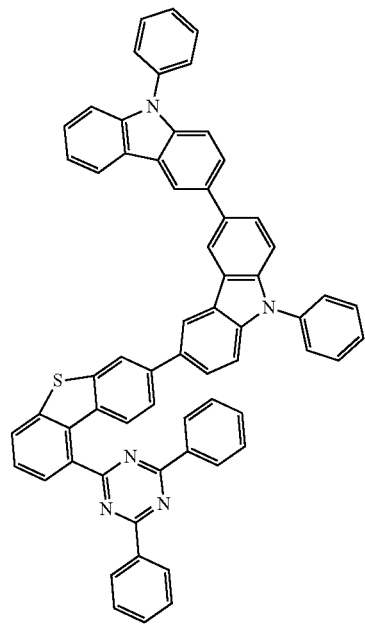 [SMILES: c1ccc(-c2nc(-c3ccccc3)nc(-c3cccc4sc5cc(-c6ccc7c(c6)c6cc(-c8ccc9c(c8)c8ccccc8n9-c8ccccc8)ccc6n7-c6ccccc6)ccc5c34)n2)cc1]
7
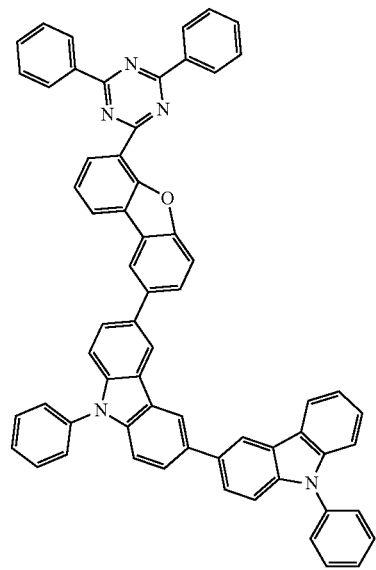 [SMILES: c1ccc(-c2nc(-c3ccccc3)nc(-c3cccc4c3oc3ccc(-c5ccc6c(c5)c5cc(-c7ccc8c(c7)c7ccccc7n8-c7ccccc7)ccc5n6-c5ccccc5)cc34)n2)cc1] 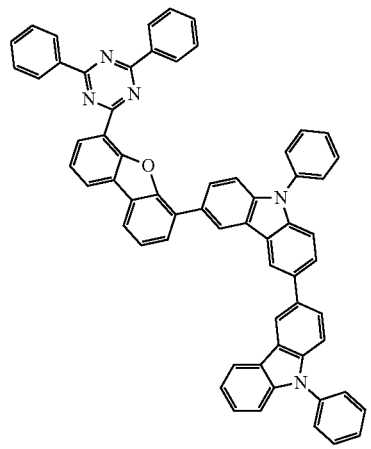 [SMILES: c1ccc(-c2nc(-c3ccccc3)nc(-c3cccc4c3oc3c(-c5ccc6c(c5)c5cc(-c7ccc8c(c7)c7ccccc7n8-c7ccccc7)ccc5n6-c5ccccc5)cccc34)n2)cc1] 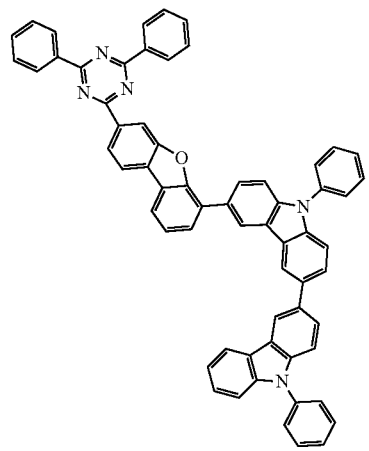 [SMILES: c1ccc(-c2nc(-c3ccccc3)nc(-c3ccc4c(c3)oc3c(-c5ccc6c(c5)c5cc(-c7ccc8c(c7)c7ccccc7n8-c7ccccc7)ccc5n6-c5ccccc5)cccc34)n2)cc1]

TABLE 1-continued
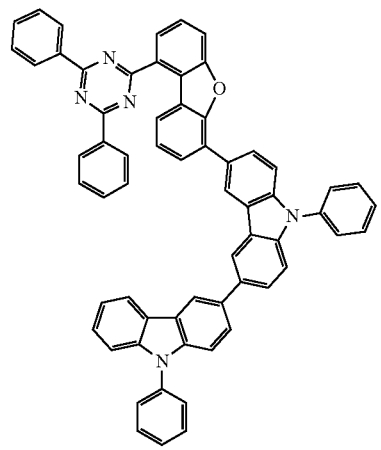 [SMILES: c1ccc(-c2nc(-c3ccccc3)nc(-c3cccc4oc5c(-c6ccc7c(c6)c6cc(-c8ccc9c(c8)c8ccccc8n9-c8ccccc8)ccc6n7-c6ccccc6)cccc5c34)n2)cc1] 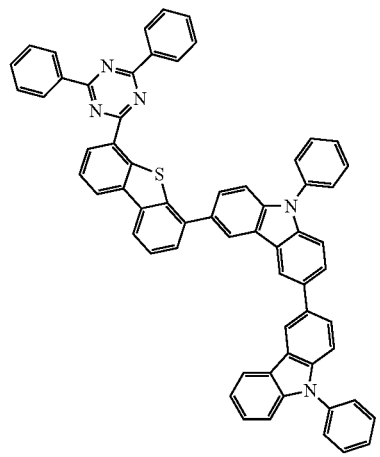 [SMILES: c1ccc(-c2nc(-c3ccccc3)nc(-c3cccc4c3sc3c(-c5ccc6c(c5)c5cc(-c7ccc8c(c7)c7ccccc7n8-c7ccccc7)ccc5n6-c5ccccc5)cccc34)n2)cc1] 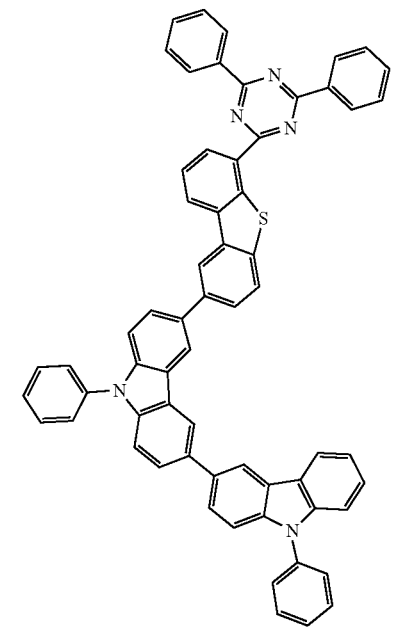 [SMILES: c1ccc(-c2nc(-c3ccccc3)nc(-c3cccc4c3sc3ccc(-c5ccc6c(c5)c5cc(-c7ccc8c(c7)c7ccccc7n8-c7ccccc7)ccc5n6-c5ccccc5)cc34)n2)cc1]
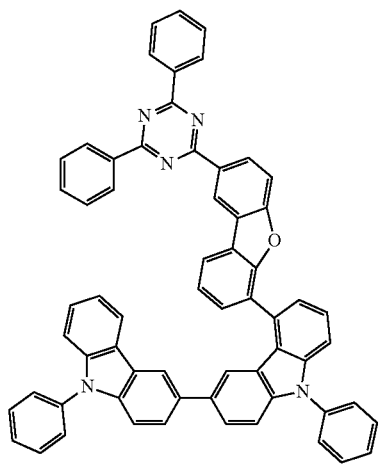 [SMILES: c1ccc(-c2nc(-c3ccccc3)nc(-c3ccc4oc5c(-c6cccc7c6c6cc(-c8ccc9c(c8)c8ccccc8n9-c8ccccc8)ccc6n7-c6ccccc6)cccc5c4c3)n2)cc1] 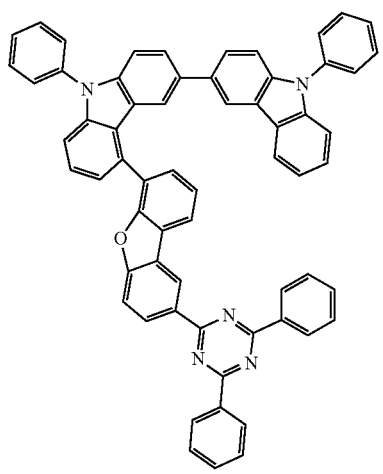 [SMILES: c1ccc(-c2nc(-c3ccccc3)nc(-c3ccc4oc5c(-c6cccc7c6c6cc(-c8ccc9c(c8)c8ccccc8n9-c8ccccc8)ccc6n7-c6ccccc6)cccc5c4c3)n2)cc1] 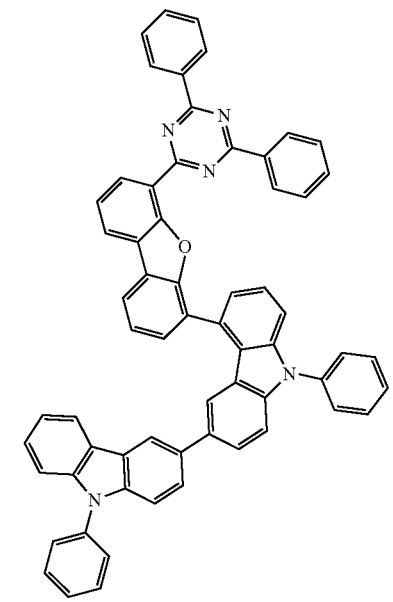 [SMILES: c1ccc(-c2nc(-c3ccccc3)nc(-c3cccc4c3oc3c(-c5cccc6c5c5cc(-c7ccc8c(c7)c7ccccc7n8-c7ccccc7)ccc5n6-c5ccccc5)cccc34)n2)cc1]

TABLE 1-continued
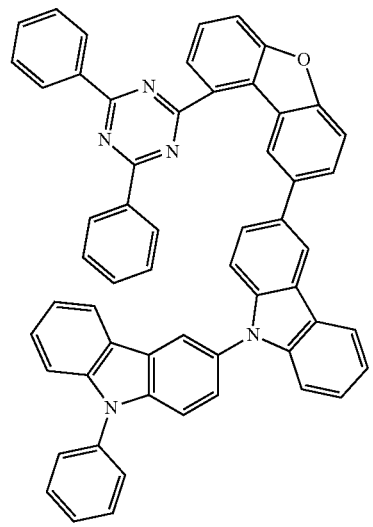
8
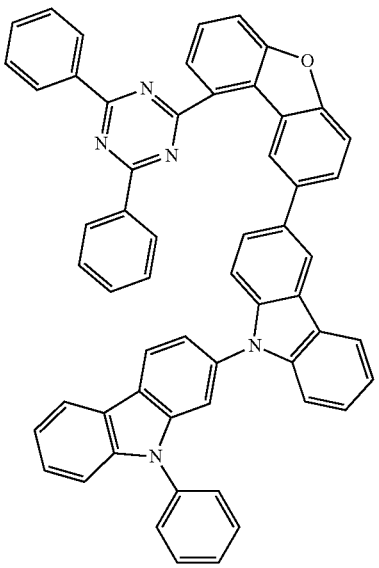 [SMILES: c1ccc(-c2nc(-c3ccccc3)nc(-c3cccc4oc5ccc(-c6ccc7c(c6)c6ccccc6n7-c6ccc7c8ccccc8n(-c8ccccc8)c7c6)cc5c34)n2)cc1]
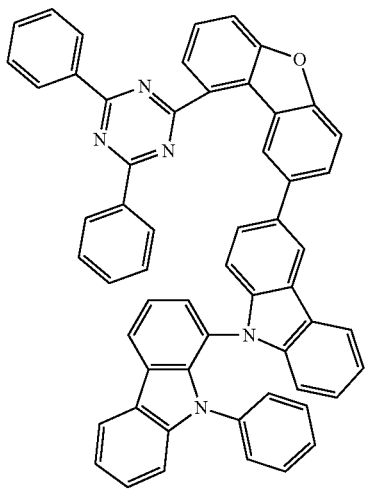 [SMILES: c1ccc(-c2nc(-c3ccccc3)nc(-c3cccc4oc5ccc(-c6ccc7c(c6)c6ccccc6n7-c6cccc7c8ccccc8n(-c8ccccc8)c67)cc5c34)n2)cc1]
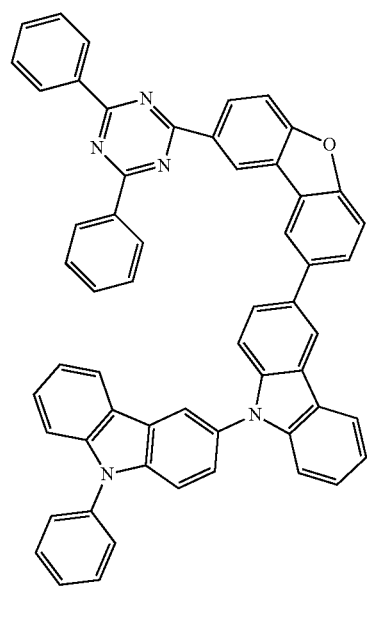 [SMILES: c1ccc(-c2nc(-c3ccccc3)nc(-c3ccc4oc5ccc(-c6ccc7c(c6)c6ccccc6n7-c6ccc7c(c6)c6ccccc6n7-c6ccccc6)cc5c4c3)n2)cc1]
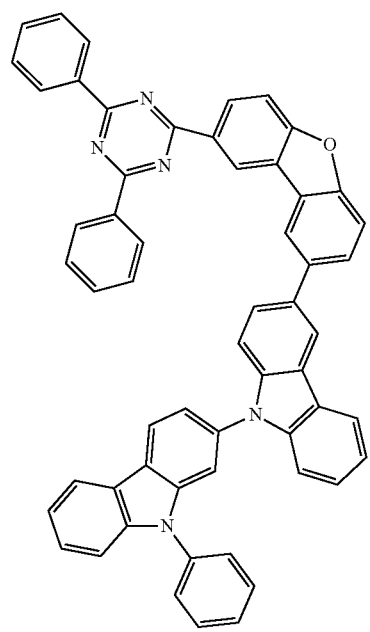 [SMILES: c1ccc(-c2nc(-c3ccccc3)nc(-c3ccc4oc5ccc(-c6ccc7c(c6)c6ccccc6n7-c6ccc7c8ccccc8n(-c8ccccc8)c7c6)cc5c4c3)n2)cc1]
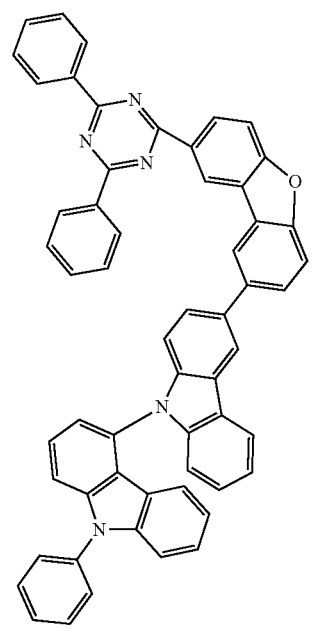 [SMILES: c1ccc(-c2nc(-c3ccccc3)nc(-c3ccc4oc5ccc(-c6ccc7c(c6)c6ccccc6n7-c6cccc7c6c6ccccc6n7-c6ccccc6)cc5c4c3)n2)cc1]

TABLE 1-continued
| 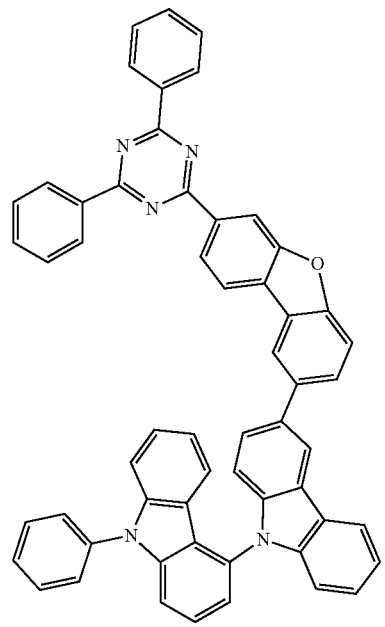 | 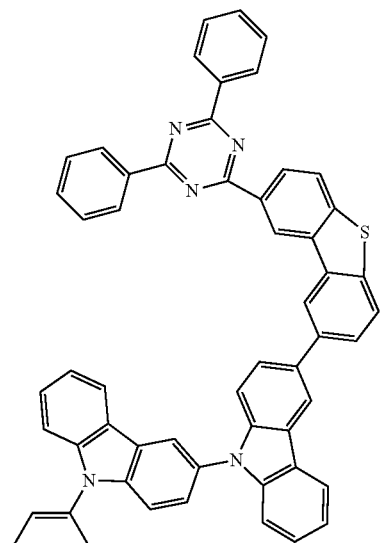 | 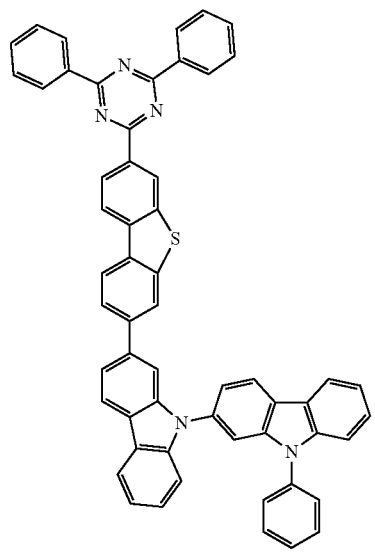 [SMILES: c1ccc(-c2nc(-c3ccccc3)nc(-c3ccc4c(c3)sc3cc(-c5ccc6c7ccccc7n(-c7ccc8c9ccccc9n(-c9ccccc9)c8c7)c6c5)ccc34)n2)cc1] |
|---|---|---|
| 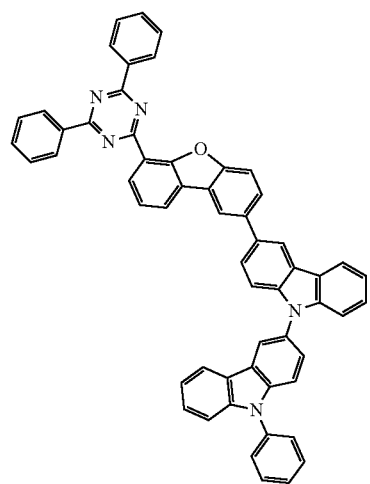 | 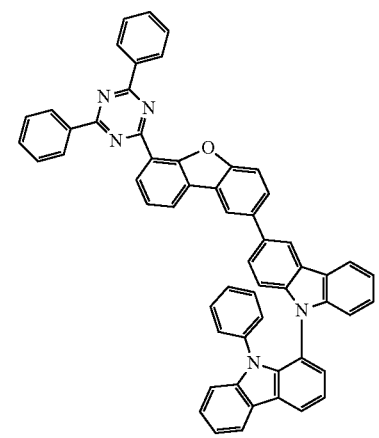 [SMILES: c1ccc(-c2nc(-c3ccccc3)nc(-c3cccc4c3oc3ccc(-c5ccc6c(c5)c5ccccc5n6-c5cccc6c7ccccc7n(-c7ccccc7)c56)cc34)n2)cc1] | 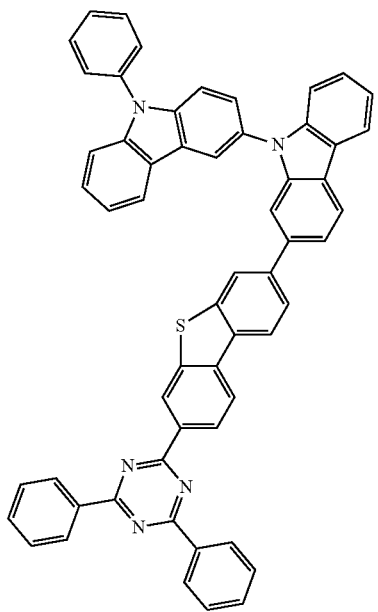 [SMILES: c1ccc(-c2nc(-c3ccccc3)nc(-c3ccc4c(c3)sc3cc(-c5ccc6c7ccccc7n(-c7ccc8c(c7)c7ccccc7n8-c7ccccc7)c6c5)ccc34)n2)cc1] |

TABLE 1-continued

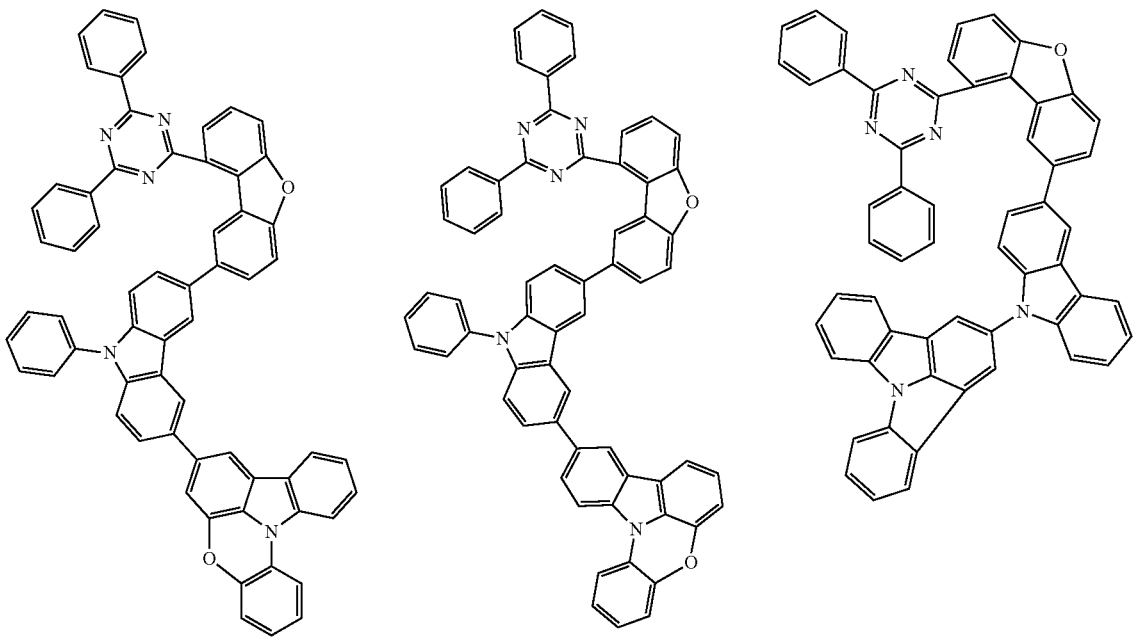

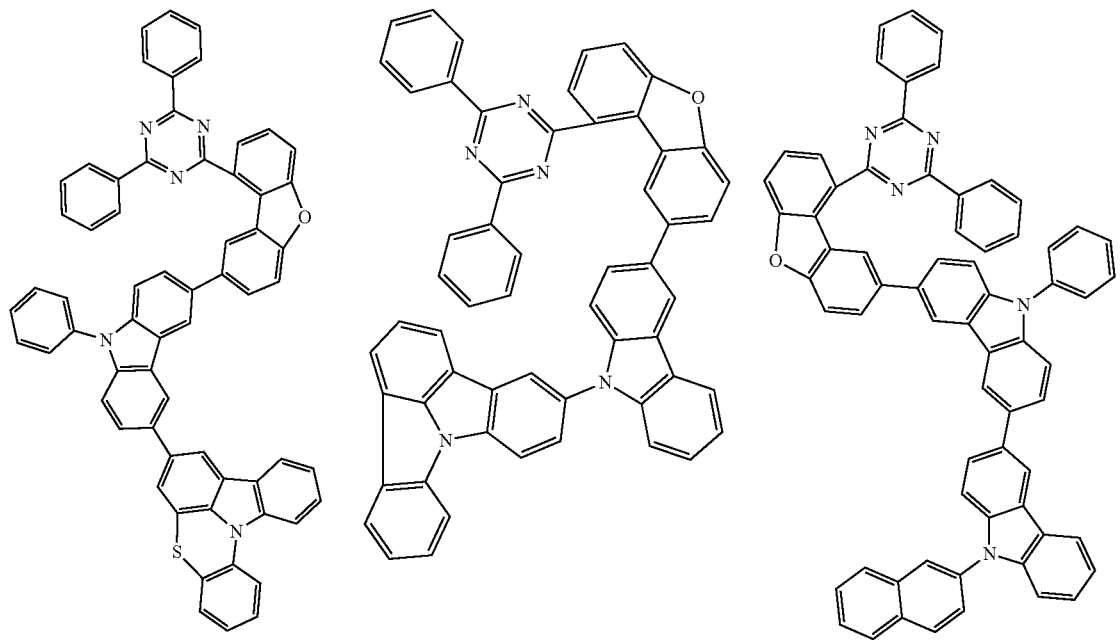

Particularly preferred examples of compounds of the formula (1), (1a), (1b), (1c), (1d), (1e), (1f), (1g), (1h), (1i) or (1j) that are selected in accordance with the invention are the aforementioned compounds 1 to 8 in Table 1.

The preparation of the compounds of the formula (1) or of the preferred compounds of the formula (1a), (1b), (1c), (1d), (1e), (1f), (1g), (1h), (1i) or (1j) and of the compounds 1 to 8 is known to those skilled in the art. The compounds of the invention can be prepared by synthesis steps known to those skilled in the art, for example bromination, Suzuki coupling, Ullmann coupling, Hartwig-Buchwald coupling, etc. A suitable synthesis method is shown in general terms in scheme 1 below.

The compounds of the formula (1) or (1a), (1c), (1d), (1g) or (1h) can be prepared according to Scheme 1 below, where Y, R, p, q, Ar, Ar$_1$ and Ar$_2$ have one of the definitions given above.

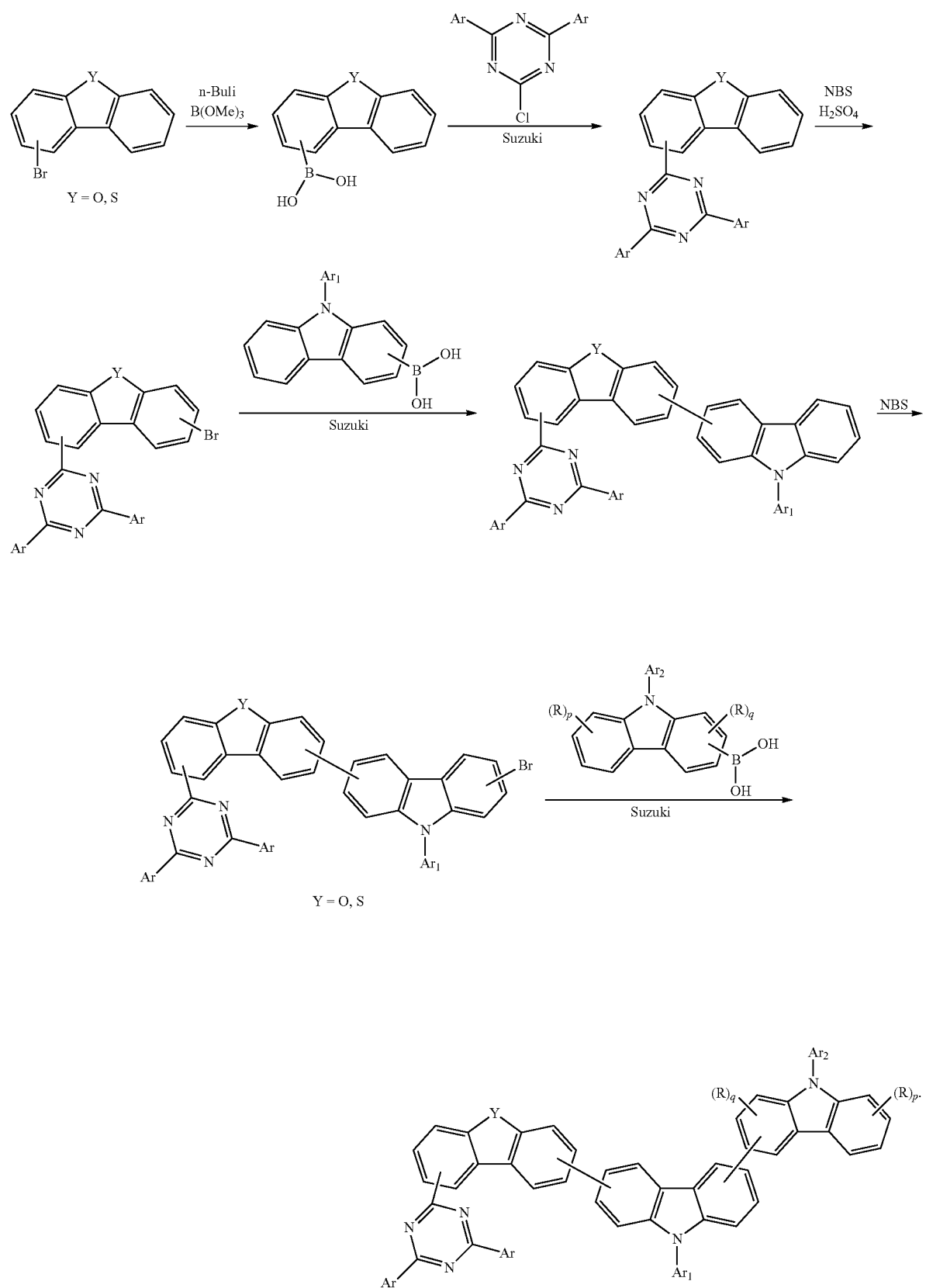

The compounds of the formula (1) or (1b), (1e), (1f), (1i) or (1j) can be prepared according to Scheme 2 below, where Y, R, r, s, Ar and $Ar_1$ have one of the definitions given above.
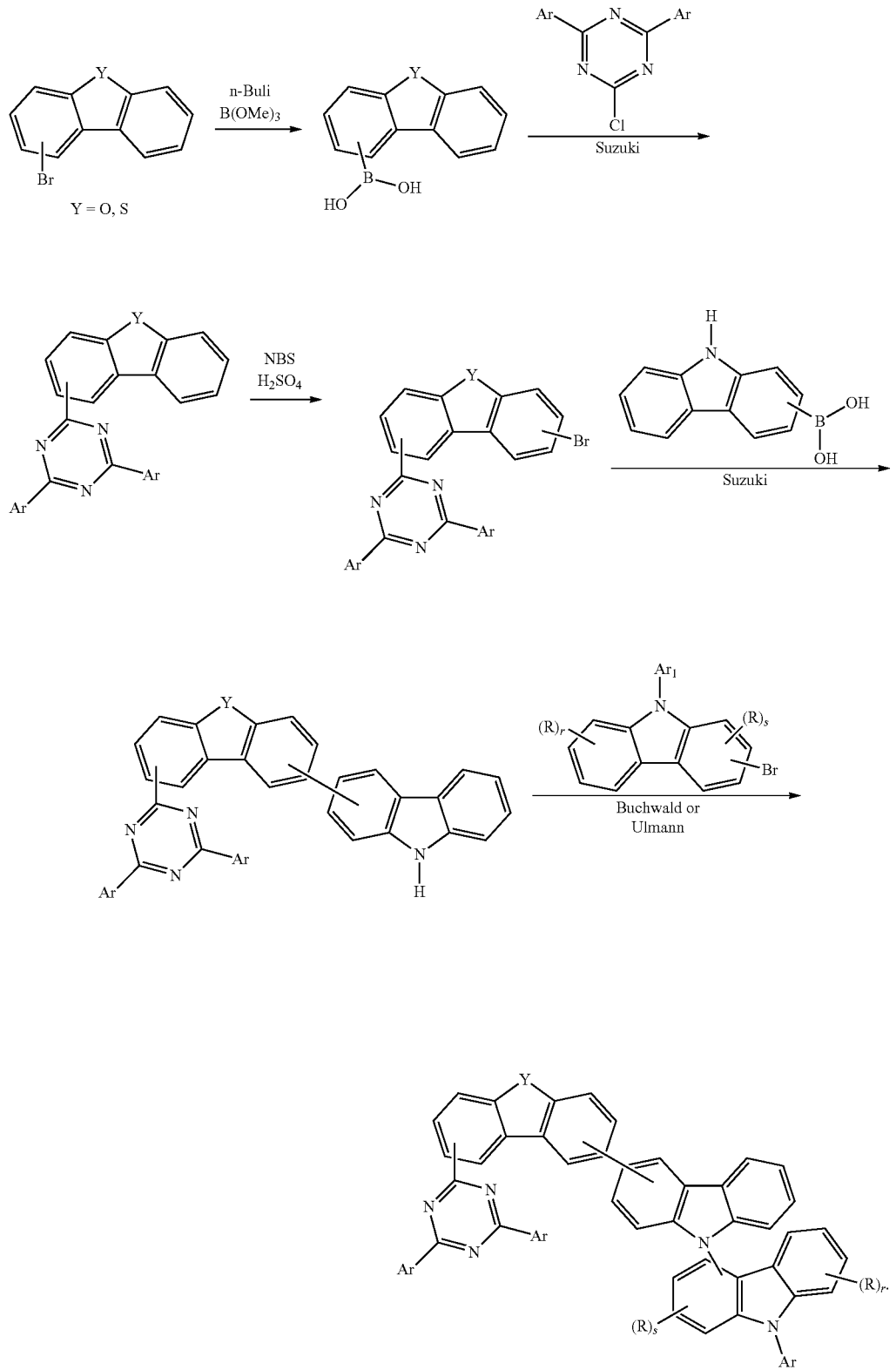
Scheme 2

Triphenylene Derivatives of the Formula (2):

In one embodiment of the invention, compounds of the formula (2) as described above are selected, which are used in the composition together with compounds of the formulae (1), (1a), (1b), (1c), (1d), (1e), (1f), (1g), (1h), (1i) and (1j) as described above or described as preferred, or with the compounds in Table 1, especially compounds 1 to 8.

$Ar_4$ in compounds of the formula (2) is preferably a heteroaromatic ring system which has 5 to 40 ring atoms and may be substituted by one or more $R^1$ radicals, where $R^1$ in each case independently has a definition given above or specified as preferred hereinafter.

Compounds of the formula (2) in which $Ar_4$ is in each case a particularly preferred heteroaromatic ring system are represented by the formulae (2a), (2b) and (2c)

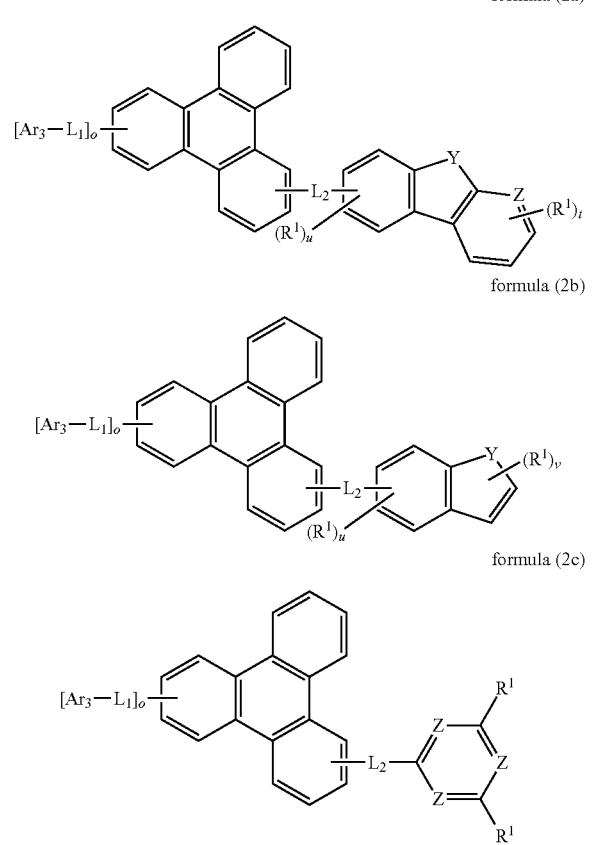

formula (2a)

formula (2b)

formula (2c)

where the symbols and indices $Ar_3$, $L_1$ and $L_2$ used have an aforementioned definition or preferred definition specified hereinafter and independently at each instance is N or $CR^1$ where $R^1$ has an aforementioned definition or preferred definition specified hereinafter, Y is O or S, t and u are each independently 0, 1, 2 or 3 and v is in each case independently 0, 1 or 2.

The invention accordingly further provides a composition as described above, where the compound of the formula (2) corresponds to the compound of the formula (2a), (2b) or (2c).

In the compounds of the formulae (2a) and (2b), Y is preferably S.

In compounds of the formula (2a), Z is preferably $CR^1$ where $R^1$ has an aforementioned definition or preferred definition specified hereinafter.

In compounds of the formula (2c), Z is at least once preferably N or at least twice preferably N or three times N. More preferably, Z is in each case N.

In compounds of the formula (2a), t is preferably 0, 1 or 2.

In compounds of the formula (2a), u is preferably 0 or 1.

In compounds of the formula (2b), v is preferably 2.

In compounds of the formula (2b), u is preferably 0.

The linkers $L_1$, $L_2$ in the formulae (2), (2a), (2b) or (2c) are the same or different at each instance and are a single bond or an aromatic or heteroaromatic ring system which has 5 to 30 ring atoms and may be substituted by one or more $R^3$ radicals.

In a preferred embodiment of the compounds of the formula (2), (2a), (2b) or (2c), $L_1$ and $L_2$ are each independently a single bond or an aromatic or heteroaromatic ring system selected from L-1 to L-16

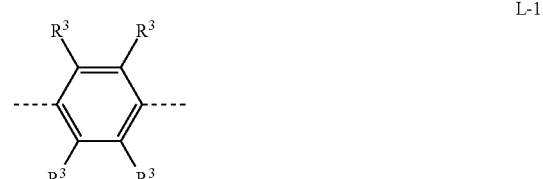

L-1

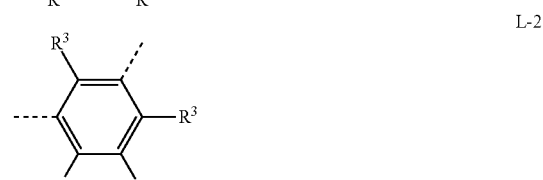

L-2

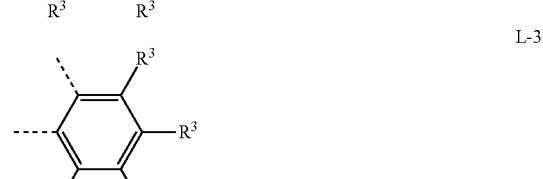

L-3

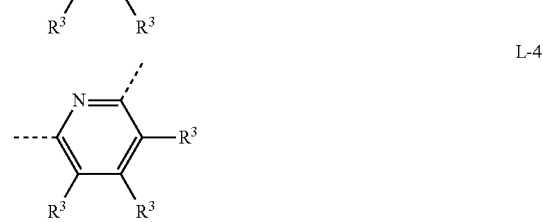

L-4

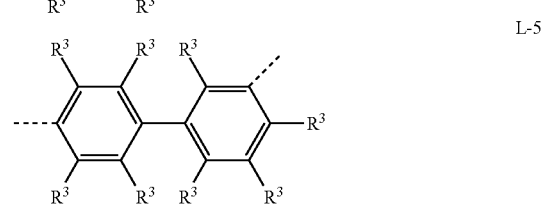

L-5

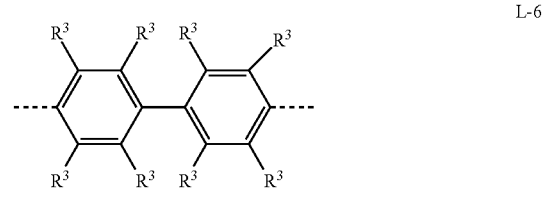

L-6

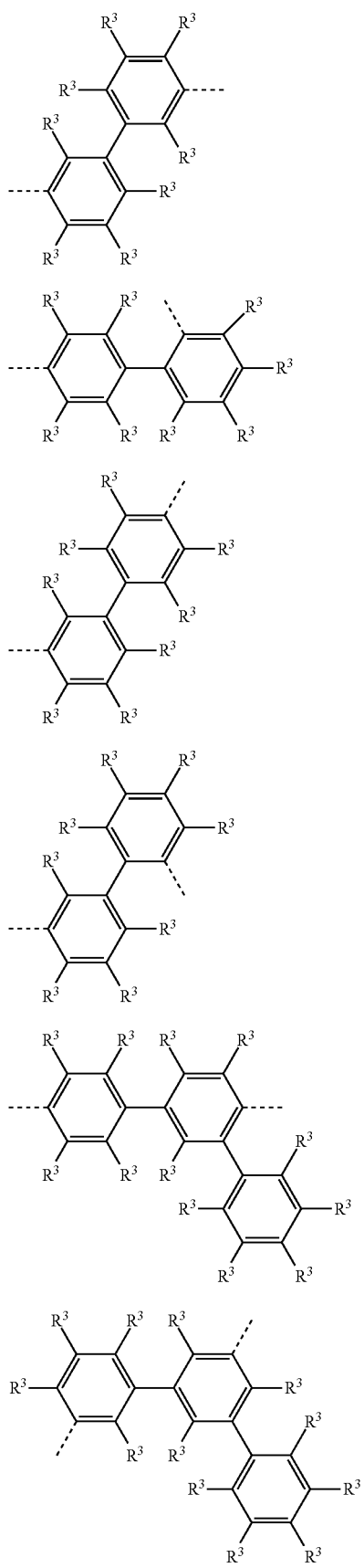
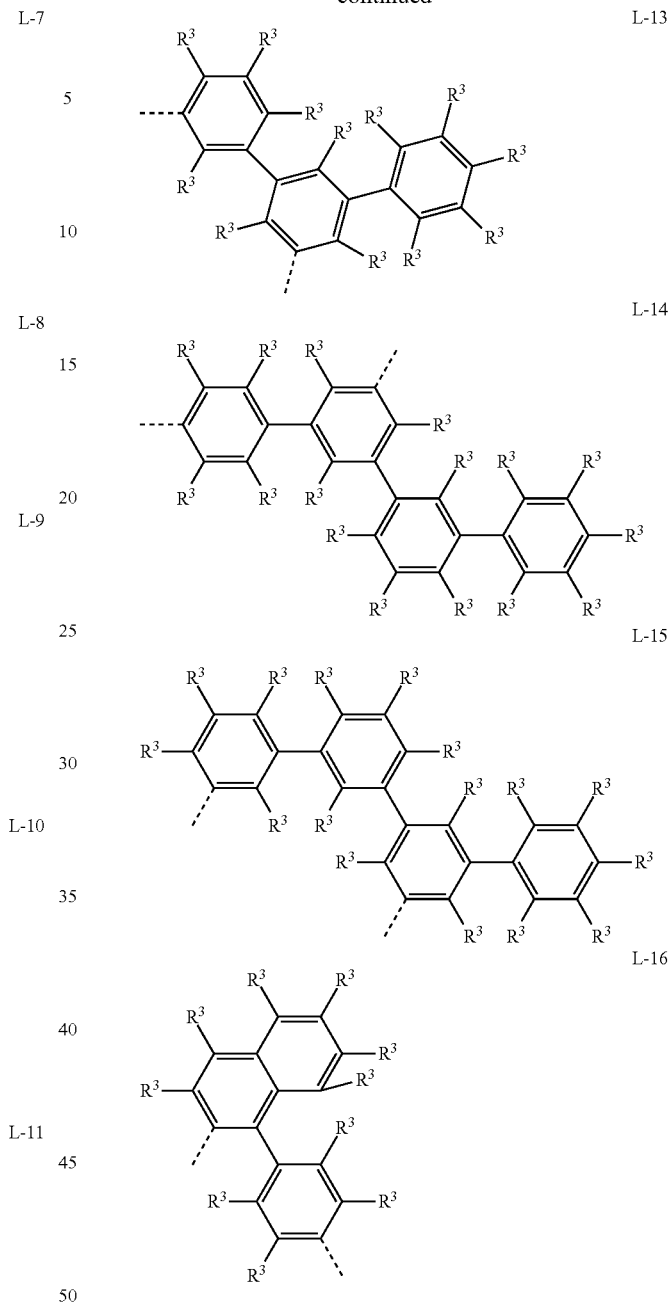

where $R^3$ is the same or different at each instance and has a definition as described above or described as preferred hereinafter, and the dotted bond represents the bond to the corresponding carbon atom.

In a preferred embodiment of the compounds of the formula (2), (2a), (2b) or (2c), $L_1$ at each instance is preferably a single bond.

In a preferred embodiment of the compounds of the formula (2), (2a), (2b) or (2c), $L_2$ at each instance is preferably a single bond or a linker selected from L-2, L-3, L-4, L-5, L-7 or L-13.

$R^3$ in the linkers L-1 to L-16 at each instance is independently preferably H or phenyl, more preferably H.

The invention accordingly further provides a composition as described above, where the compound of the formula (2) corresponds to the compound of the formula (2a), (2b) or (2c) and $L_1$ at each instance is a single bond.

In compounds of the formula (2), (2a), (2b) or (2c), o is 0 or 1, preferably 0. $Ar_3$ at each instance is an aromatic or heteroaromatic ring system which has 6 to 40 ring atoms and may be substituted by one or more $R^1$ radicals, where $R^1$ at each instance is the same or different and has a definition as described above or described as preferred hereinafter.

In compounds of the formula (2), (2a), (2b) or (2c), or compounds of the formula (2), (2a), (2b) or (2c) described as preferred, $Ar_3$ at each instance is preferably selected from the aromatic or heteroaromatic ring systems Ar-1 to Ar-8

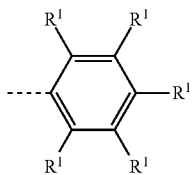
Ar-1

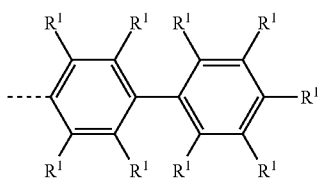
Ar-2

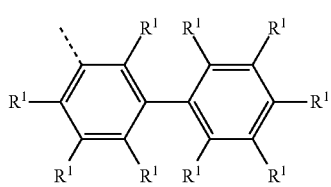
Ar-3

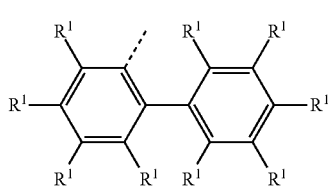
Ar-4

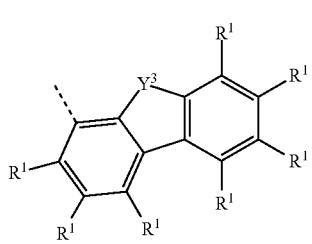
Ar-5

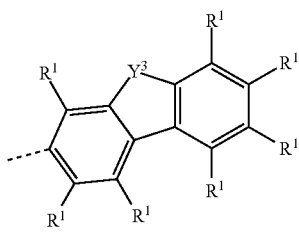
Ar-6

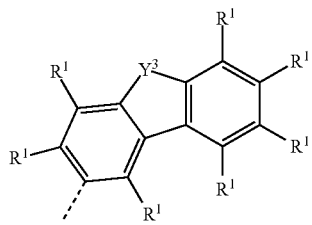
Ar-7

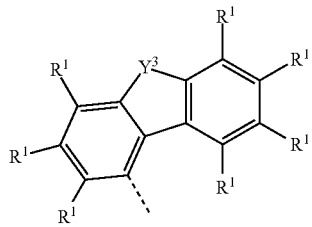
Ar-8 where $Y^3$ at each instance is the same or different and is O, $NR^\#$, S or $C(R^\#)_2$ where the $R^\#$ radical bonded to N is not H, and $R^1$ has the aforementioned definition or a preferred definition below and the dotted bond represents the bond to $L_1$ or the triphenylene.

The $R^\#$ radical is the same or different at each instance and is H, D, F, Cl, Br, I, CN, $NO_2$, $N(Ar)_2$, $N(R^2)_2$, C(=O)Ar, $C(=O)R^2$, P(=O)$(Ar)_2$, $P(Ar)_2$, $B(Ar)_2$, $Si(Ar)_3$, $Si(R^2)_3$, a straight-chain alkyl, alkoxy or thioalkyl group having 1 to 20 carbon atoms or a branched or cyclic alkyl, alkoxy or thioalkyl group having 3 to 20 carbon atoms or an alkenyl group having 2 to 20 carbon atoms, each of which may be substituted by one or more $R^2$ radicals, where one or more nonadjacent $CH_2$ groups may be replaced by $R^2C=CR^2$, $Si(R^2)_2$, C=O, C=S, $C=NR^2$, $P(=O)(R^2)$, SO, $SO_2$, $NR^2$, O, S or $CONR^2$ and where one or more hydrogen atoms may be replaced by D, F, Cl, Br, I, CN or $NO_2$, an aromatic or heteroaromatic ring system which has 5 to 40 ring atoms and may be substituted in each case by one or more $R^2$ radicals, an aryloxy or heteroaryloxy group which has 5 to 40 ring atoms and may be substituted by one or more $R^2$ radicals, or an aralkyl or heteroaralkyl group which has 5 to 40 ring atoms and may be substituted by one or more $R^2$ radicals; at the same time, it is optionally possible for two substituents $R^\#$ bonded to the same carbon atom or to adjacent carbon atoms to form a monocyclic or polycyclic, aliphatic, aromatic or heteroaromatic ring system which may be substituted by one or more $R^2$ radicals.

$Y^3$ is preferably O, S or $C(CH_3)_2$. $Y^3$ is most preferably S.

In the structures Ar-1 to Ar-8, the substituent $R^1$ is the same or different at each instance and is selected from the group consisting of H, D, F, CN, an aliphatic hydrocarbyl radical having 1 to 20 carbon atoms, or an aromatic or heteroaromatic ring system having 5 to 30 ring atoms in which one or more hydrogen atoms may be replaced by D, F, Cl, Br, I or CN and which may be substituted by one or more alkyl groups each having 1 to 4 carbon atoms; at the same time, it is possible for two or more adjacent substituents $R^1$ together to form a mono- or polycyclic, aliphatic ring system. In the structures Ar-1 to Ar-8, the substituent $R^1$ is the same or different at each instance and is preferably selected from the group consisting of H, F, CN, an aliphatic hydrocarbyl radical having 1 to 10 carbon atoms or an aromatic or heteroaromatic ring system having 5 to 30 ring atoms. In the structures Ar-1 to Ar-8, the substituent $R^1$ at each instance is preferably H.

In compounds of the formula (2), (2a), (2b) or (2c), or compounds of the formula (2), (2a), (2b) or (2c) described as preferred, $Ar_3$ at each instance is more preferably selected from the aromatic or heteroaromatic ring systems Ar-1, Ar-5, Ar-6, Ar-7 or Ar-8, where the substituents $R^1$ and $Y^3$ have an aforementioned definition or one described as preferred.

When, in compounds of the formula (2), (2a) or (2b), t, u or v are greater than 0, the substituent $R^1$ is the same or different at each instance and is preferably selected from the group consisting of D, F, an alkyl group having 1 to 40 carbon atoms or an aromatic or heteroaromatic ring system which has 5 to 40 ring atoms and may be substituted by one or more $R^2$ radicals.

The aromatic or heteroaromatic ring system having 5 to 40 ring atoms in this $R^1$ is preferably derived from benzene, dibenzofuran, dibenzothiophene, 9-phenylcarbazole, biphenyl, triphenylene and triazine which may be substituted by one or more $R^2$ radicals. Particularly preferred substituents $R^1$ in $[R^1]t$, when t is greater than 0, are each independently phenyl, triphenylene and triazine which may be substituted by one or more substituents $R^2$. In this case, $R^2$ at each instance is in each case independently preferably phenyl or triphenylene.

Particularly preferred substituents $R^1$ in $[R^1]_u$, when u is greater than 0, are each independently phenyl which may be substituted by one or more substituents $R^2$.

Particularly preferred substituents $R^1$ in $[R^1]_v$, when v is greater than 0, are each independently phenyl which may be substituted by one or more substituents $R^2$.

In compounds of the formula (2c), the substituents $R^1$ are preferably selected from phenyl, biphenyl, dibenzothiophene, pyrimidine or pyridine which may be substituted by one or more substituents $R^2$, where two substituents $R^1$ together may also form an aromatic ring which may be substituted by one or more substituents $R^2$. In this case, $R^2$ at each instance is in each case independently preferably phenyl.

In compounds of the formula (2a), it is likewise preferable when two substituents $R^1$ preferably bonded to adjacent carbon atoms form a monocyclic or polycyclic, aliphatic, aromatic or heteroaromatic ring system, preferably an aromatic or heteroaromatic ring system.

The substituent $R^2$ is the same or different at each instance and is preferably selected from the group consisting of D, F, Cl, Br, I, CN, $NO_2$, $N(Ar)_2$, $NH_2$, $N(R^3)_2$, $C(=O)Ar$, $C(=O)H$, $C(=O)R^3$, $P(=O)(Ar)_2$, a straight-chain alkyl, alkoxy or thioalkyl group having 1 to 40 carbon atoms or a branched or cyclic alkyl, alkoxy or thioalkyl group having 3 to 40 carbon atoms or an alkenyl or alkynyl group having 2 to 40 carbon atoms, each of which may be substituted by one or more $R^3$ radicals, an aromatic or heteroaromatic ring system which has 5 to 60 ring atoms and may in each case be substituted by one or more $R^3$ radicals, an aryloxy or heteroaryloxy group which has 5 to 60 ring atoms and may be substituted in each case by one or more $R^3$ radicals. The substituent $R^2$ when it occurs is more preferably an aromatic or heteroaromatic ring system as described above, preferably selected and derived from the group of carbazole, 9-phenylcarbazole, dibenzofuran, dibenzothiophene, fluorene, terphenyl or spirobifluorene.

In the case of substitution of one of the substituents $R^2$ as described above by a substituent $R^3$, the definitions of $R^3$ as described above or described as preferred are applicable.

$R^3$ is preferably the same or different at each instance and is H or an aromatic or heteroaromatic ring system having 5 to 30 ring atoms. $R^3$ is more preferably H or phenyl.

Examples of suitable compounds of the formula (2), (2a), (2b) or (2c) that are selected in accordance with the invention are the structures shown below in Table 2.

TABLE 2

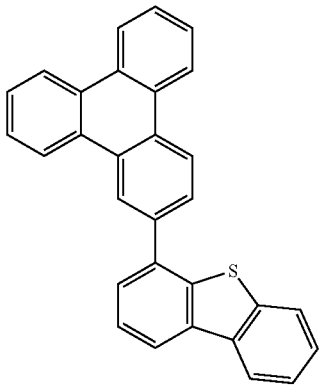 [SMILES: c1ccc2c(c1)sc1c(-c3ccc4c5ccccc5c5ccccc5c4c3)cccc12]

9

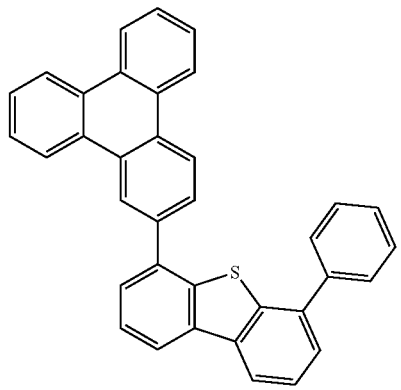 [SMILES: c1ccc(-c2cccc3c2sc2c(-c4ccc5c6ccccc6c6ccccc6c5c4)cccc23)cc1]

10

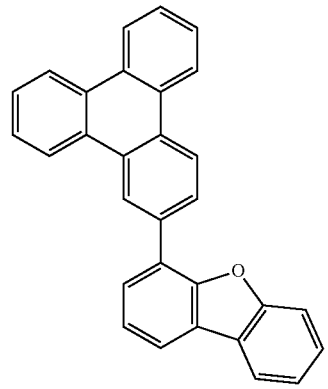 [SMILES: c1ccc2c(c1)oc1c(-c3ccc4c5ccccc5c5ccccc5c4c3)cccc12]

TABLE 2-continued
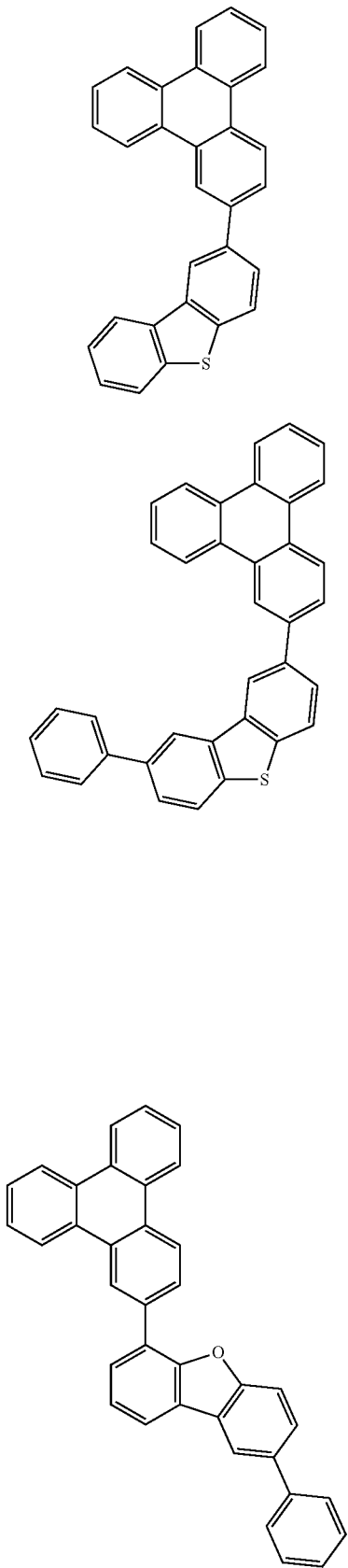

TABLE 2-continued
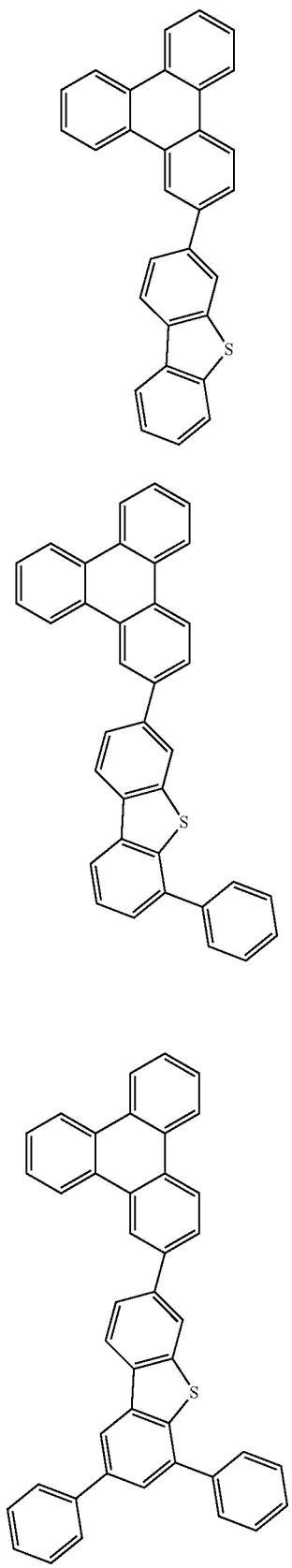
TABLE 2-continued
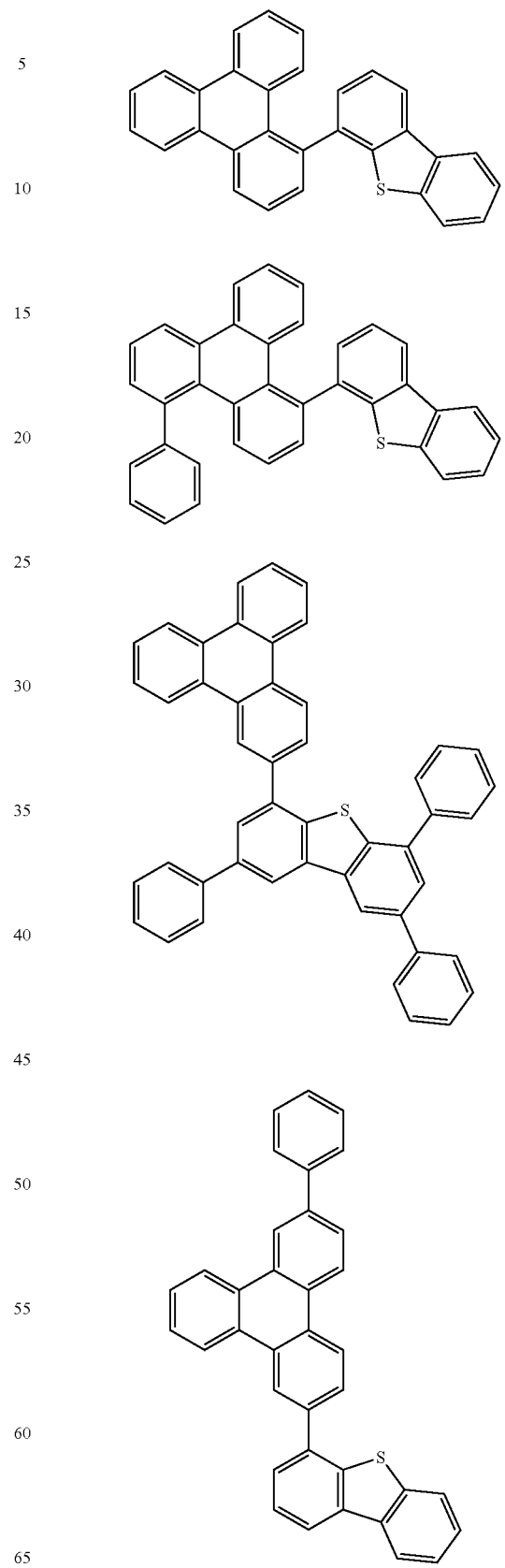

TABLE 2-continued
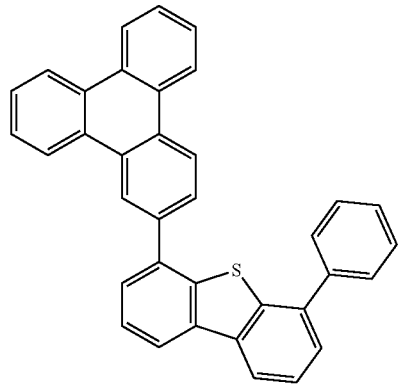 [SMILES: c1ccc(-c2cccc3c2sc2c(-c4ccc5c6ccccc6c6ccccc6c5c4)cccc23)cc1]
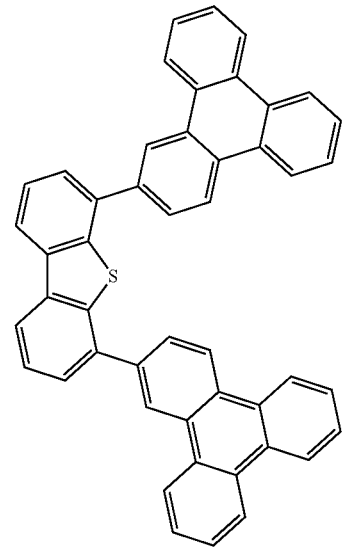 [SMILES: c1cc(-c2ccc3c4ccccc4c4ccccc4c3c2)c2sc3c(-c4ccc5c6ccccc6c6ccccc6c5c4)cccc3c2c1]
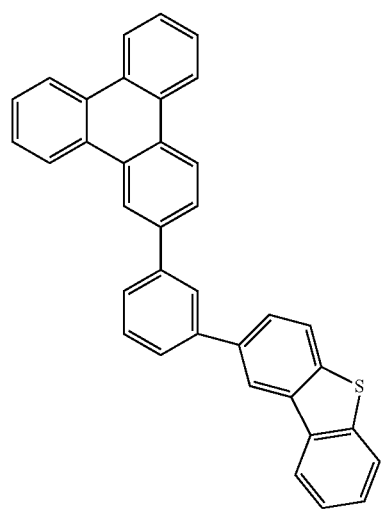 [SMILES: c1cc(-c2ccc3sc4ccccc4c3c2)cc(-c2ccc3c4ccccc4c4ccccc4c3c2)c1]
TABLE 2-continued
12
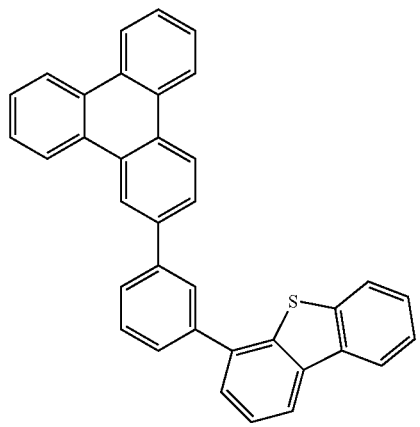 [SMILES: c1cc(-c2ccc3c4ccccc4c4ccccc4c3c2)cc(-c2cccc3c2sc2ccccc23)c1]
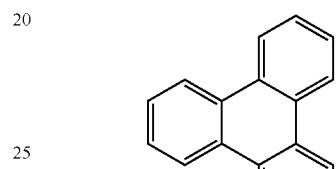
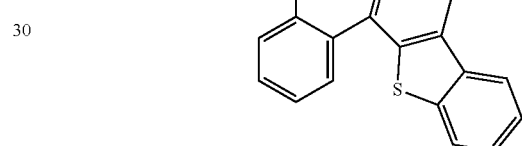
11
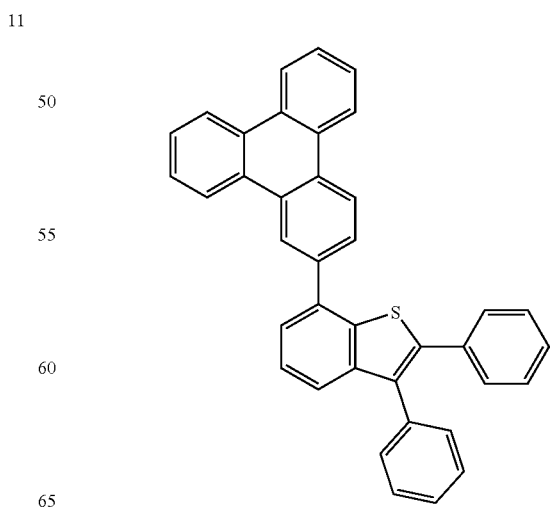

TABLE 2-continued
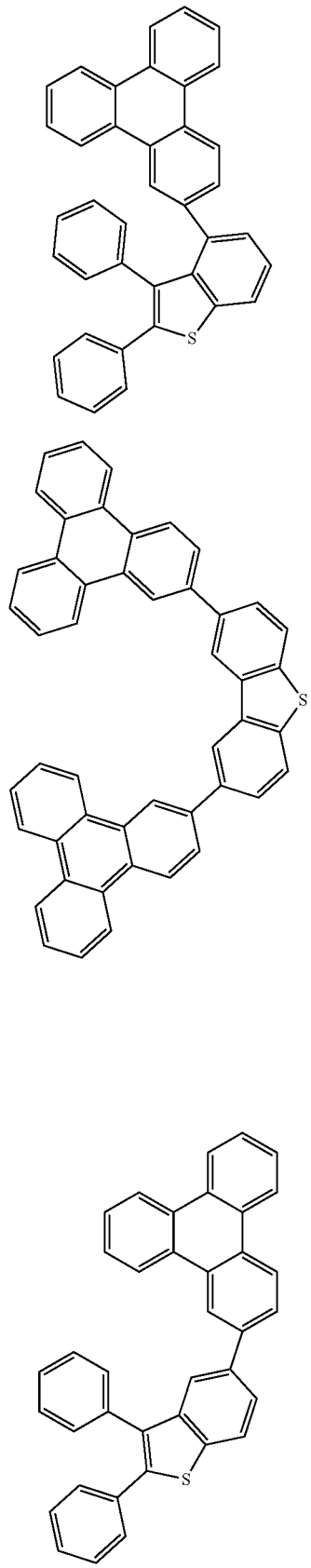
TABLE 2-continued
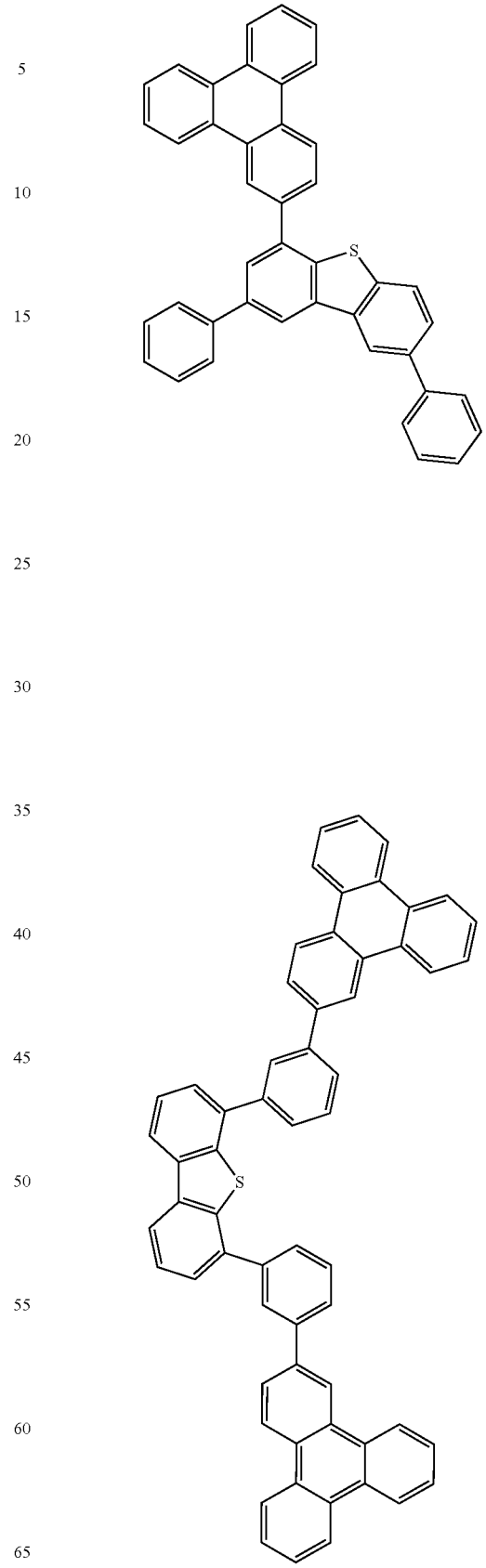

TABLE 2-continued
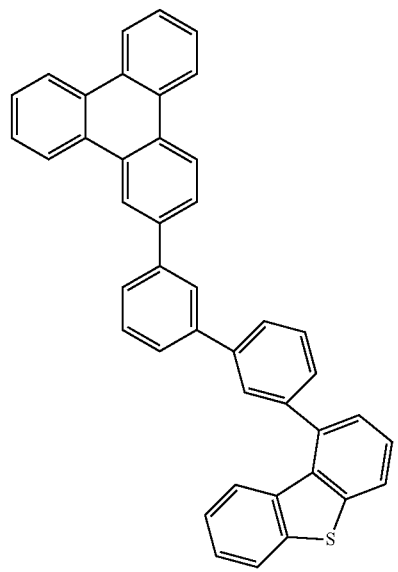 [SMILES: c1cc(-c2cccc(-c3cccc4sc5ccccc5c34)c2)cc(-c2ccc3c4ccccc4c4ccccc4c3c2)c1]
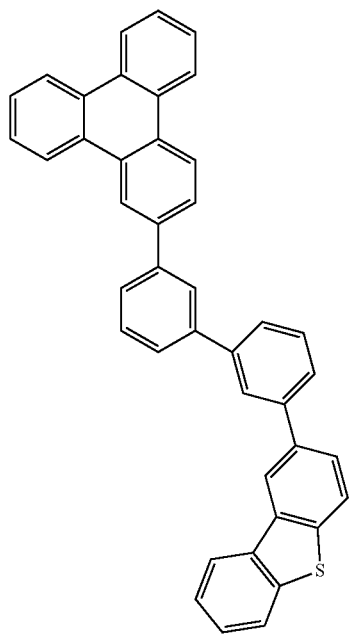
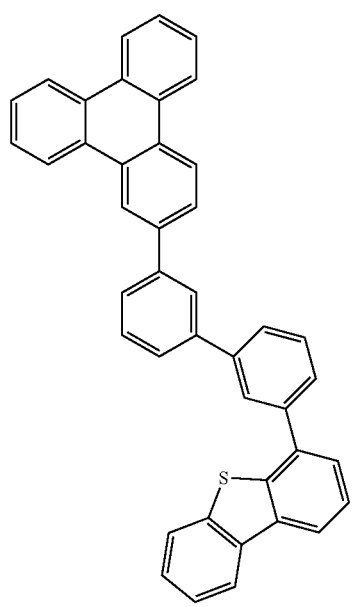 [SMILES: c1cc(-c2cccc(-c3cccc4c3sc3ccccc34)c2)cc(-c2ccc3c4ccccc4c4ccccc4c3c2)c1]
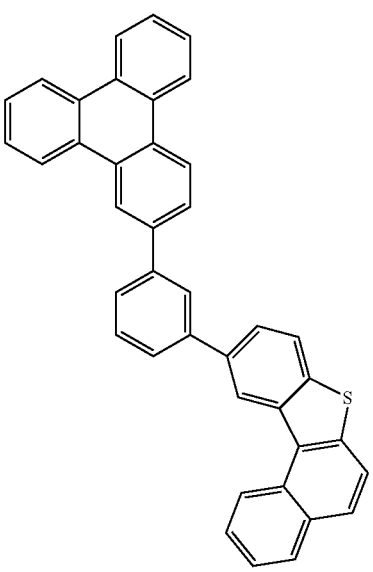 [SMILES: c1cc(-c2ccc3c4ccccc4c4ccccc4c3c2)cc(-c2ccc3sc4ccc5ccccc5c4c3c2)c1]

TABLE 2-continued
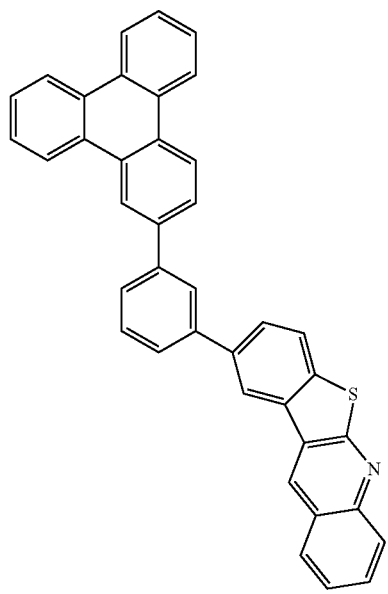 [SMILES: c1cc(-c2ccc3sc4nc5ccccc5cc4c3c2)cc(-c2ccc3c4ccccc4c4ccccc4c3c2)c1]
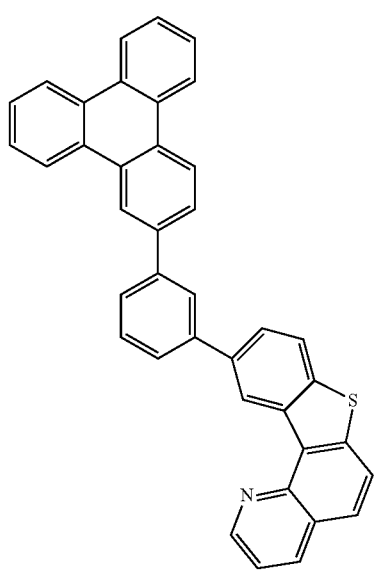 [SMILES: c1cc(-c2ccc3c4ccccc4c4ccccc4c3c2)cc(-c2ccc3sc4ccc5cccnc5c4c3c2)c1]
TABLE 2-continued
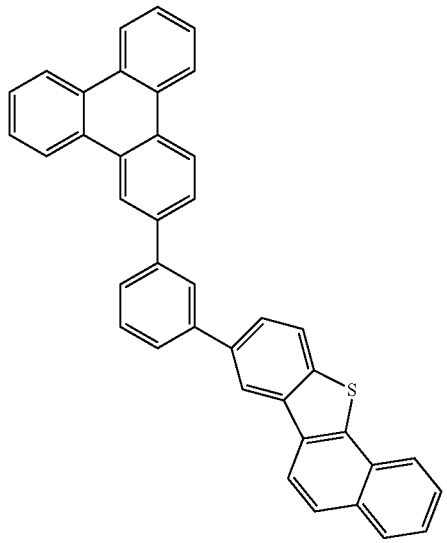 [SMILES: c1cc(-c2ccc3sc4c5ccccc5ccc4c3c2)cc(-c2ccc3c4ccccc4c4ccccc4c3c2)c1]
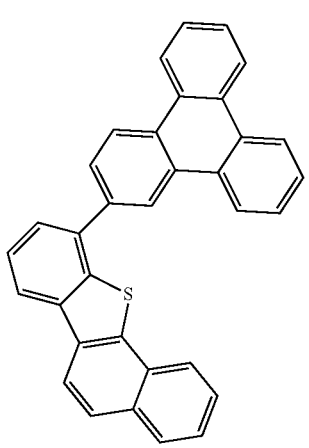 [SMILES: c1ccc2c(c1)ccc1c3cccc(-c4ccc5c6ccccc6c6ccccc6c5c4)c3sc21]
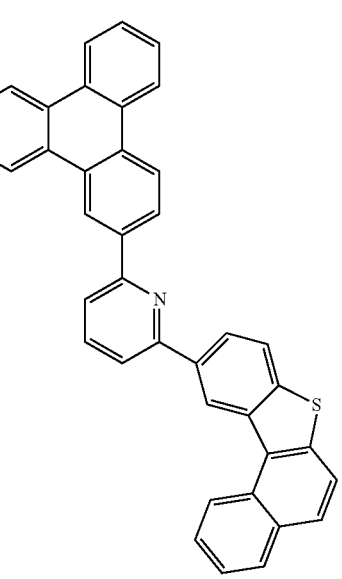

TABLE 2-continued
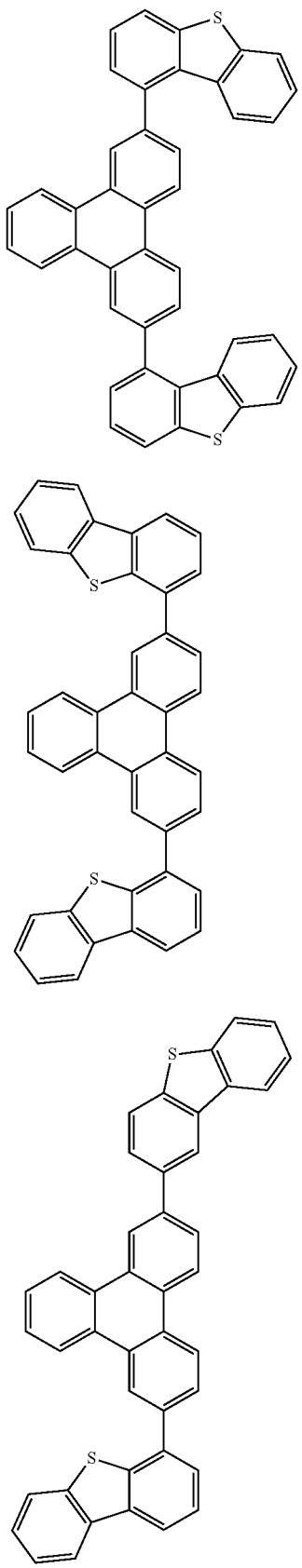
14
TABLE 2-continued
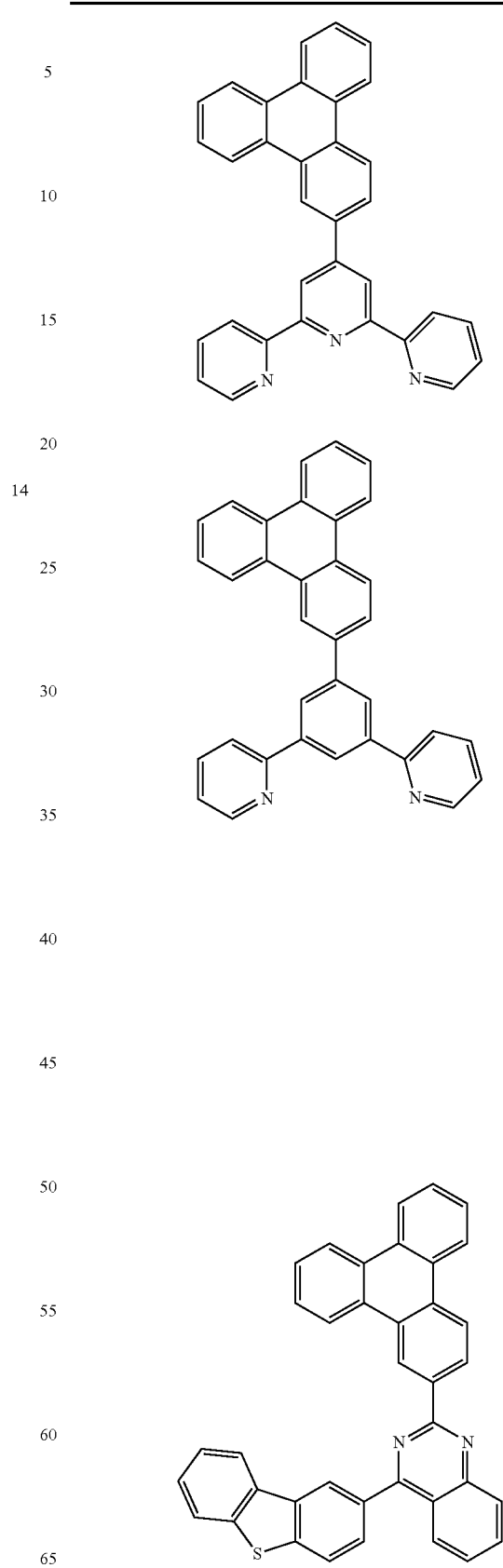

TABLE 2-continued
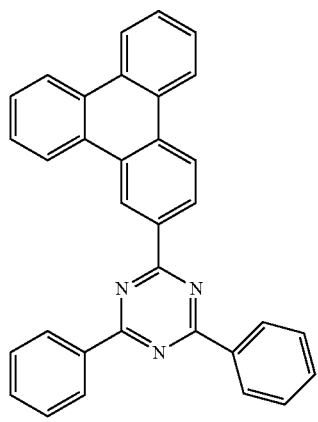 [SMILES: c1ccc(-c2nc(-c3ccccc3)nc(-c3ccc4c5ccccc5c5ccccc5c4c3)n2)cc1]
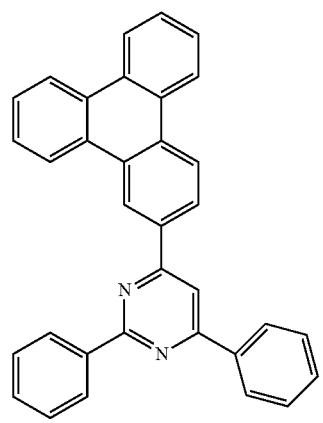 [SMILES: c1ccc(-c2cc(-c3ccc4c5ccccc5c5ccccc5c4c3)nc(-c3ccccc3)n2)cc1]
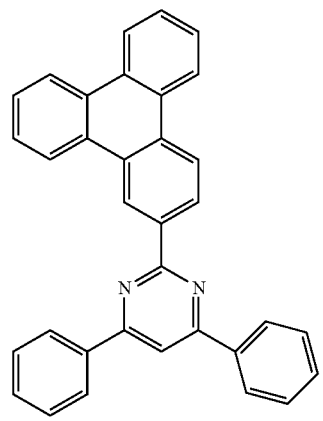 [SMILES: c1ccc(-c2cc(-c3ccccc3)nc(-c3ccc4c5ccccc5c5ccccc5c4c3)n2)cc1]
TABLE 2-continued
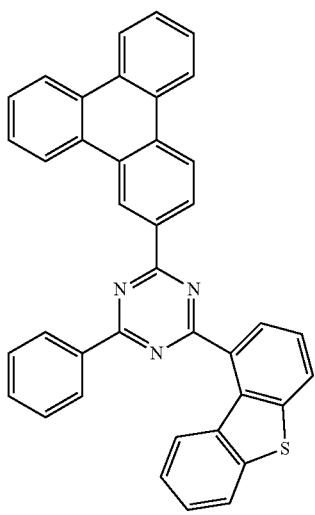 [SMILES: c1ccc(-c2nc(-c3ccc4c5ccccc5c5ccccc5c4c3)nc(-c3cccc4sc5ccccc5c34)n2)cc1]
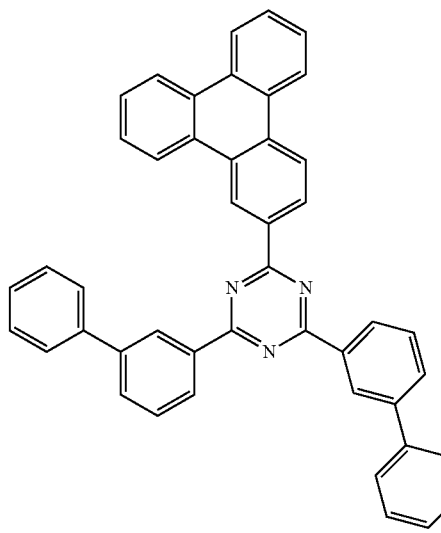
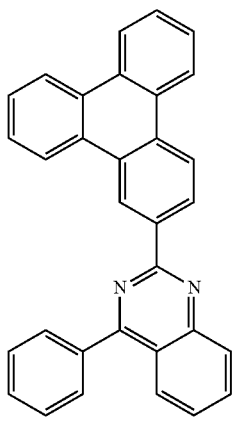 [SMILES: c1ccc(-c2nc(-c3ccc4c5ccccc5c5ccccc5c4c3)nc3ccccc23)cc1]

TABLE 2-continued
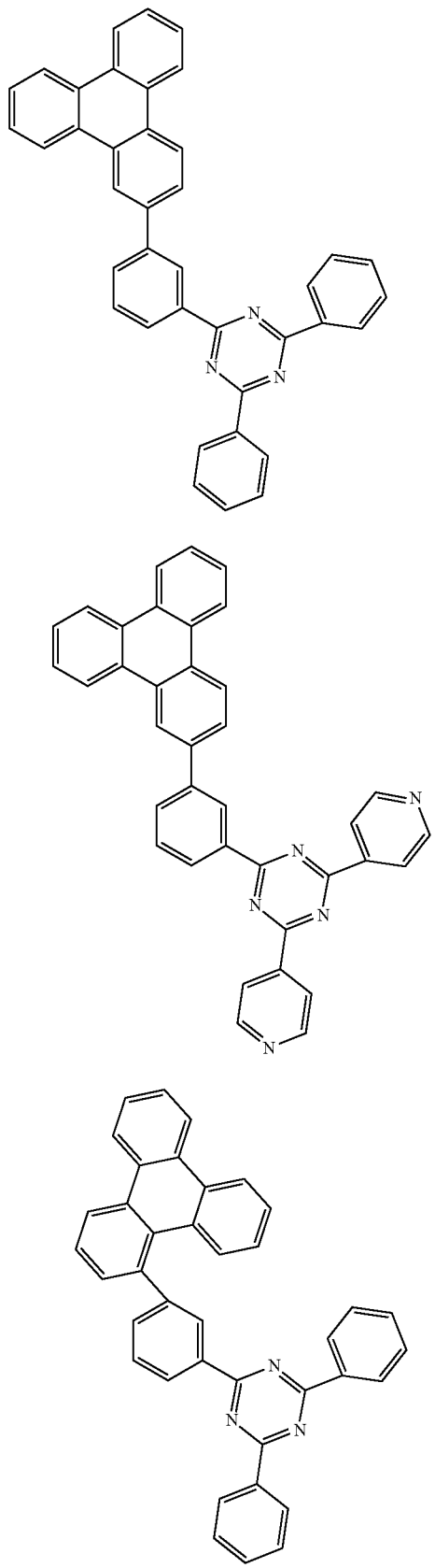
16
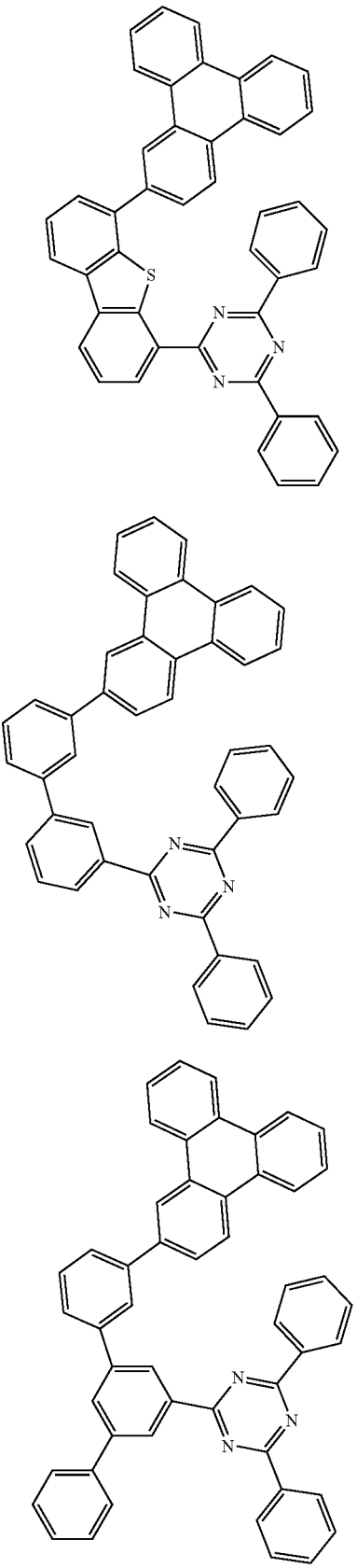
17

TABLE 2-continued
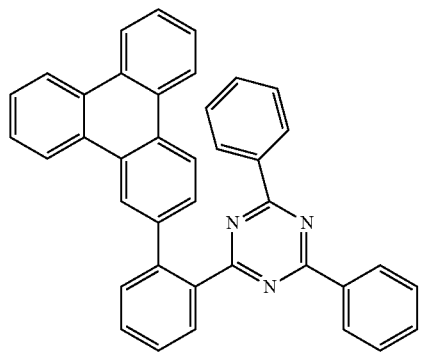 [SMILES: c1ccc(-c2nc(-c3ccccc3)nc(-c3ccccc3-c3ccc4c5ccccc5c5ccccc5c4c3)n2)cc1]
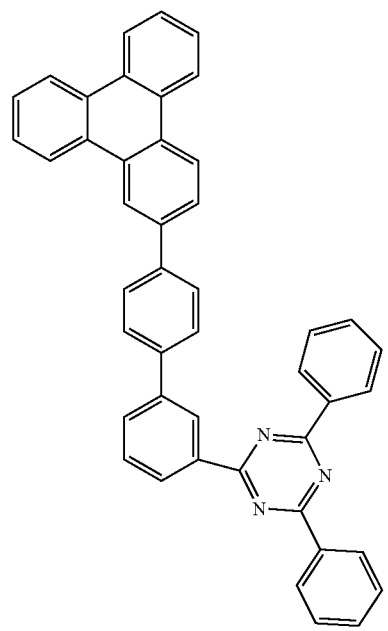 [SMILES: c1ccc(-c2nc(-c3ccccc3)nc(-c3cccc(-c4ccc(-c5ccc6c7ccccc7c7ccccc7c6c5)cc4)c3)n2)cc1]
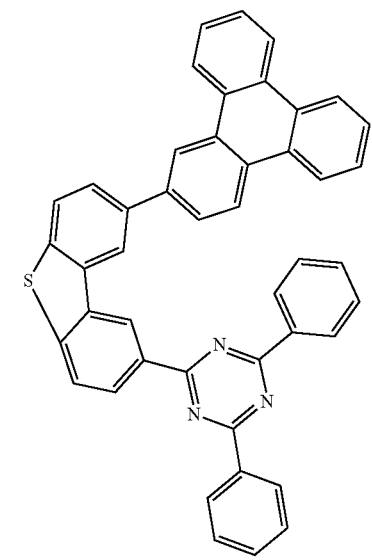 [SMILES: c1ccc(-c2nc(-c3ccccc3)nc(-c3ccc4sc5ccc(-c6ccc7c8ccccc8c8ccccc8c7c6)cc5c4c3)n2)cc1]
TABLE 2-continued
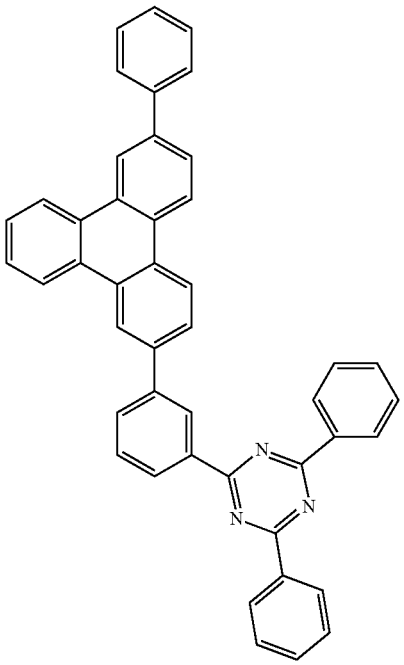 [SMILES: c1ccc(-c2ccc3c4ccc(-c5cccc(-c6nc(-c7ccccc7)nc(-c7ccccc7)n6)c5)cc4c4ccccc4c3c2)cc1]
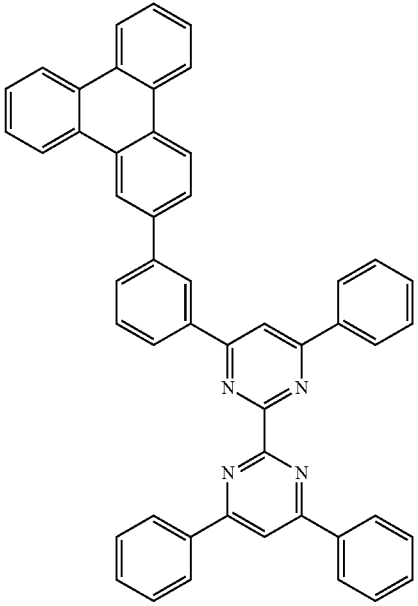 [SMILES: c1ccc(-c2cc(-c3ccccc3)nc(-c3nc(-c4ccccc4)cc(-c4cccc(-c5ccc6c7ccccc7c7ccccc7c6c5)c4)n3)n2)cc1]

TABLE 2-continued

TABLE 2-continued

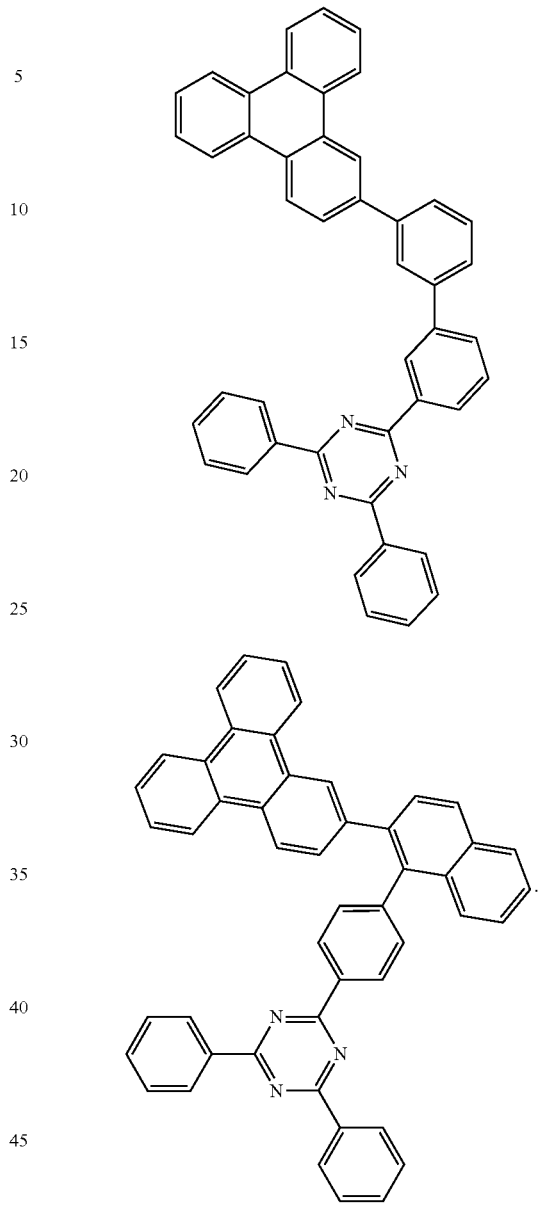

Particularly suitable examples of compounds of the formula (2), (2a), (2b) or (2c) that are selected in accordance with the invention are the compounds 9 to 17, as described above.

The preparation of the compounds of the formula (2) or of the preferred compounds of the formulae (2a), (2b) and (2c) and the compounds from Table 2 is known to those skilled in the art. The compounds can be prepared by synthesis steps known to those skilled in the art, for example bromination, Suzuki coupling. The preparation of the triphenylene derivatives is also described, for example, in WO 2009/021126 or US 2015340618.

The compounds of the formula (2) or the preferred compounds of the formula (2a) can be prepared, for example, according to Scheme 3. The reaction conditions are known to the person skilled in the art. The bromination of triphenylene is described, for example, in US20060280965. Suzuki coupling is described, for example, in WO 2009/021126.

Scheme 3

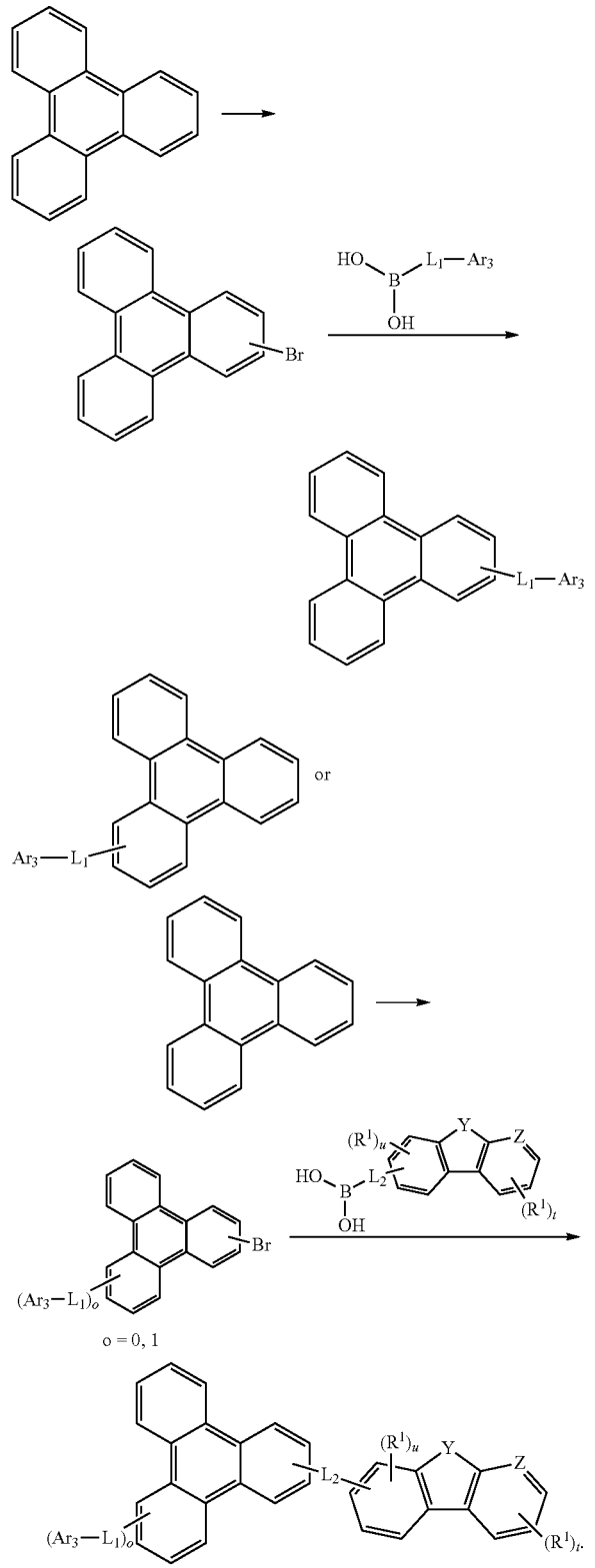

The compounds of the formula (2) or the preferred compounds of the formula (2b) can be prepared, for example, according to Scheme 4. The reaction conditions are known to the person skilled in the art. The bromination of triphenylene is described, for example, in US20060280965. Suzuki coupling is described, for example, in WO 2009/021126.

Scheme 4

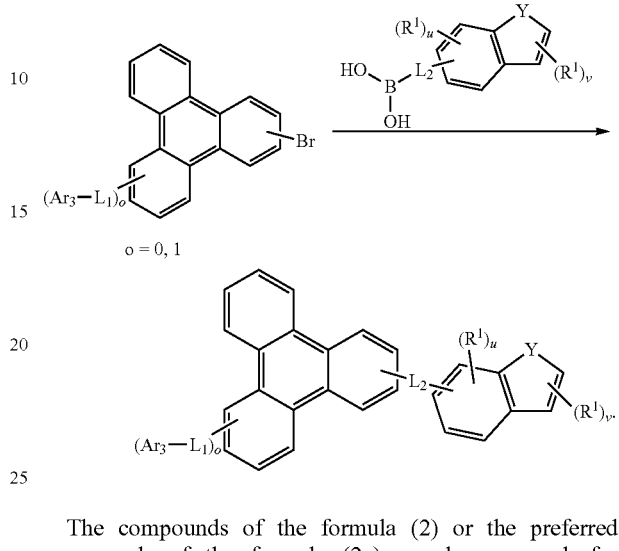

The compounds of the formula (2) or the preferred compounds of the formula (2c) can be prepared, for example, according to Scheme 5. The reaction conditions are known to the person skilled in the art. The bromination of triphenylene is described, for example, in US20060280965. Suzuki coupling is described, for example, in WO 2009/021126.

Scheme 5

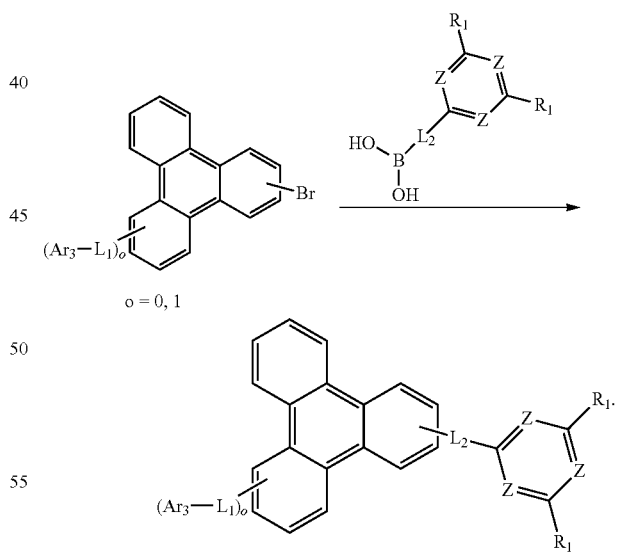

All the indices and symbols used in Schemes 3 to 5 have the same meaning as described above or described as preferred.

Further details of the syntheses and further literature references are cited in the examples.

The aforementioned host materials of the formulae (1) and (1a) to (1j) and the embodiments thereof described as preferred for the compounds from Table 1 can be combined as desired in accordance with the invention with the specified host materials of the formulae (2), (2a), (2b) and (2c) and the embodiments thereof described as preferred for the compounds from Table 2.

Particularly preferred mixtures of the host materials of the formula (1) with the host materials of the formula (2) for the composition of the invention are obtained by combination of the compounds 1 to 8 from Table 1 with the compounds from Table 2.

Very particularly preferred mixtures M1 to M72 of the host materials of the formula (1) with the host materials of the formula (2) are obtained by combination of the compounds 1 to 8 described in Table 1 with the compounds 9 to 17 described in Table 2, as shown in Table 3 below.

TABLE 3

| M1  | 1 | 9  | M2  | 1 | 10 |
|-----|---|----|-----|---|----|
| M3  | 1 | 11 | M4  | 1 | 12 |
| M5  | 1 | 13 | M6  | 1 | 14 |
| M7  | 1 | 15 | M8  | 1 | 16 |
| M9  | 1 | 17 | M10 | 2 | 9  |
| M11 | 2 | 10 | M12 | 2 | 11 |
| M13 | 2 | 12 | M14 | 2 | 13 |
| M15 | 2 | 14 | M16 | 2 | 15 |
| M17 | 2 | 16 | M18 | 2 | 17 |
| M19 | 3 | 9  | M20 | 3 | 10 |
| M21 | 3 | 11 | M22 | 3 | 12 |
| M23 | 3 | 13 | M24 | 3 | 14 |
| M25 | 3 | 15 | M26 | 3 | 16 |
| M27 | 3 | 17 | M28 | 4 | 9  |
| M29 | 4 | 10 | M30 | 4 | 11 |
| M31 | 4 | 12 | M32 | 4 | 13 |
| M33 | 4 | 14 | M34 | 4 | 15 |
| M35 | 4 | 16 | M36 | 4 | 17 |
| M37 | 5 | 9  | M38 | 5 | 10 |
| M39 | 5 | 11 | M40 | 5 | 12 |
| M41 | 5 | 13 | M42 | 5 | 14 |
| M43 | 5 | 15 | M44 | 5 | 16 |
| M45 | 5 | 17 | M46 | 6 | 9  |
| M47 | 6 | 10 | M48 | 6 | 11 |
| M49 | 6 | 12 | M50 | 6 | 13 |
| M51 | 6 | 14 | M52 | 6 | 15 |
| M53 | 6 | 16 | M54 | 6 | 17 |
| M55 | 7 | 9  | M56 | 7 | 10 |
| M57 | 7 | 11 | M58 | 7 | 12 |
| M59 | 7 | 13 | M60 | 7 | 14 |
| M61 | 7 | 15 | M62 | 7 | 16 |
| M63 | 7 | 17 | M64 | 8 | 9  |
| M65 | 8 | 10 | M66 | 8 | 11 |
| M67 | 8 | 12 | M68 | 8 | 13 |
| M69 | 8 | 14 | M70 | 8 | 15 |
| M71 | 8 | 16 | M72 | 8 | 17. |

The concentration of the bipolar host of the formula (1) as described above or described as preferred in the composition of the invention is in the range from 5% by weight to 90% by weight, preferably in the range from 10% by weight to 85% by weight, more preferably in the range from 20% by weight to 85% by weight, even more preferably in the range from 30% by weight to 80% by weight, very especially preferably in the range from 20% by weight to 60% by weight and most preferably in the range from 30% by weight to 50% by weight, based on the overall composition.

The concentration of the triphenylene derivative of the formula (2) as described above or described as preferred in the composition is in the range from 10% by weight to 95% by weight, preferably in the range from 15% by weight to 90% by weight, more preferably in the range from 15% by weight to 80% by weight, even more preferably in the range from 20% by weight to 70% by weight, very especially preferably in the range from 40% by weight to 80% by weight and most preferably in the range from 50% by weight to 70% by weight, based on the overall composition.

In a further preferred embodiment, the composition of the invention may comprise, as well as at least one compound of the formula (1) as described above or described as preferred as bipolar host, and at least one compound of the formula (2) as described above or described as preferred as uncharged co-host, further compounds as well, especially organic functional materials. In this embodiment, the composition preferably forms an organic layer in an electronic device as described hereinafter.

The present invention therefore also relates to a composition which, as well as the aforementioned materials of the formulae (1) and (2), also comprises at least one further compound selected from the group consisting of hole injection materials, hole transport materials, hole blocker materials, wide band gap materials, fluorescent emitters, phosphorescent emitters, host materials, electron blocker materials, electron transport materials, electron injection materials, n-dopants and p-dopants. It does not present any difficulties at all to the person skilled in the art to select these from a multitude of materials that are known to such a person.

n-Dopants are understood herein to mean reducing agents, i.e. electron donors. Preferred examples of n-dopants are W(hpp)$_4$ and further electron-rich metal complexes according to WO 2005/086251 A2, P=N compounds (e.g. WO 2012/175535 A1, WO 2012/175219 A1), naphthylenecarbodiimides (e.g. WO 2012/168358 A1), fluorenes (e.g. WO 2012/031735 A1), radicals and diradicals (e.g. EP 1837926 A1, WO 2007/107306 A1), pyridines (e.g. EP 2452946 A1, EP 2463927 A1), N-heterocyclic compounds (e.g. WO 2009/000237 A1) and acridines and phenazines (e.g. US 2007/145355 A1).

p-Dopants are understood herein to mean oxidizing agents, i.e. electron acceptors. Preferred examples of p-dopants are $F_4$-TCNQ, $F_6$-TNAP, NDP-2 (from Novaled), NDP-9 (from Novaled), quinones (e.g. EP 1538684 A1, WO 2006/081780 A1, WO 2009/003455 A1, WO 2010/097433 A1), radialenes (e.g. EP 1988587 A1, US 2010/102709 A1, EP 2180029 A1, WO 2011/131185 A1, WO 2011134458 A1, US 2012/223296 A1), S-containing transition metal complexes (e.g. WO 2007/134873 A1, WO 2008/061517 A2, WO 2008/061518 A2, DE 102008051737 A1, WO 2009/089821 A1, US 2010/096600 A1), bisimidazoles (e.g. WO 2008/138580 A1), phthalocyanines (e.g. WO 2008/058525 A2), bora-tetraazapentalenes (e.g. WO 2007/115540 A1), fullerenes (e.g. DE 102010046040 A1) and main group halides (e.g. WO 2008/128519 A2).

A wide band gap material is understood herein to mean a material within the scope of the disclosure of U.S. Pat. No. 7,294,849 which is characterized by a band gap of at least 3.5 eV, the band gap being understood to mean the gap between the HOMO and LUMO energy of a material.

It is preferable when the composition of the invention comprising a bipolar host of the formula (1) and an uncharged co-host of the formula (2) additionally comprises at least one light-emitting compound or an emitter, particular preference being given to phosphorescent emitters.

The term "phosphorescent emitters" typically encompasses compounds where the light is emitted through a spin-forbidden transition from an excited state having high spin multiplicity, i.e. a spin state >1, for example through a transition from a triplet state or a state having an even higher spin quantum number, for example a quintet state. This is preferably understood to mean a transition from a triplet state.

Suitable phosphorescent emitters (=triplet emitters) are especially compounds which, when suitably excited, emit light, preferably in the visible region, and also contain at least one atom of atomic number greater than 20, preferably greater than 38 and less than 84, more preferably greater than 56 and less than 80, especially a metal having this atomic number.

Preferred phosphorescence emitters used are compounds containing copper, molybdenum, tungsten, rhenium, ruthenium, osmium, rhodium, iridium, palladium, platinum, silver, gold or europium, especially compounds containing iridium or platinum. In the context of the present invention, all luminescent compounds containing the abovementioned metals are regarded as phosphorescent emitters.

In general, all phosphorescent complexes as used for phosphorescent OLEDs according to the prior art and as known to those skilled in the art in the field of organic electroluminescent devices are suitable.

Examples of the above-described emitters can be found in applications WO 2016/015815, WO 00/70655, WO 2001/41512, WO 2002/02714, WO 2002/15645, EP 1191613, EP 1191612, EP 1191614, WO 05/033244, WO 05/019373, US 2005/0258742, WO 2009/146770, WO 2010/015307, WO 2010/031485, WO 2010/054731, WO 2010/054728, WO 2010/086089, WO 2010/099852, WO 2010/102709, WO 2011/032626, WO 2011/066898, WO 2011/157339, WO 2012/007086, WO 2014/008982, WO 2014/023377, WO 2014/094961, WO 2014/094960, WO 2015/036074, WO 2015/104045, WO 2015/117718, WO 2016/015815, WO 2016/124304, WO 2017/032439, WO 2015/036074, WO 2015/117718 and WO 2016/015815.

Preferred examples of phosphorescent emitters are listed in Table 4 below.

TABLE 4

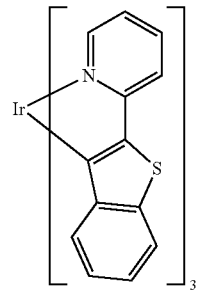

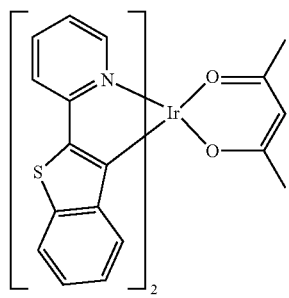

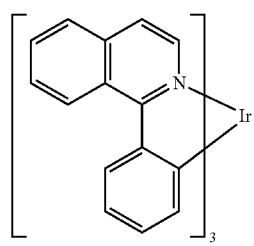

TABLE 4-continued

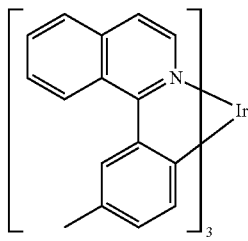

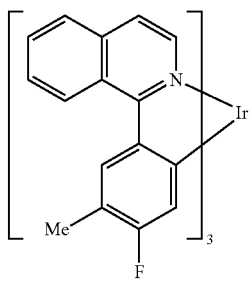

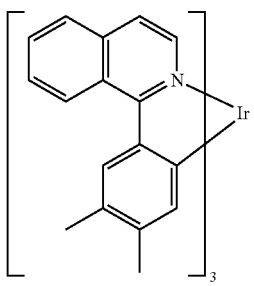

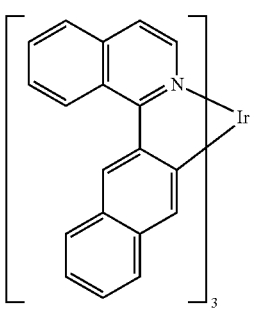

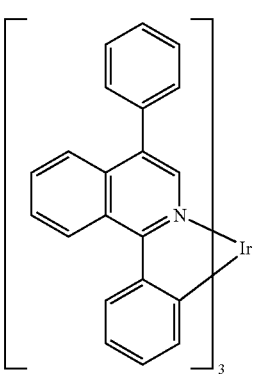

TABLE 4-continued
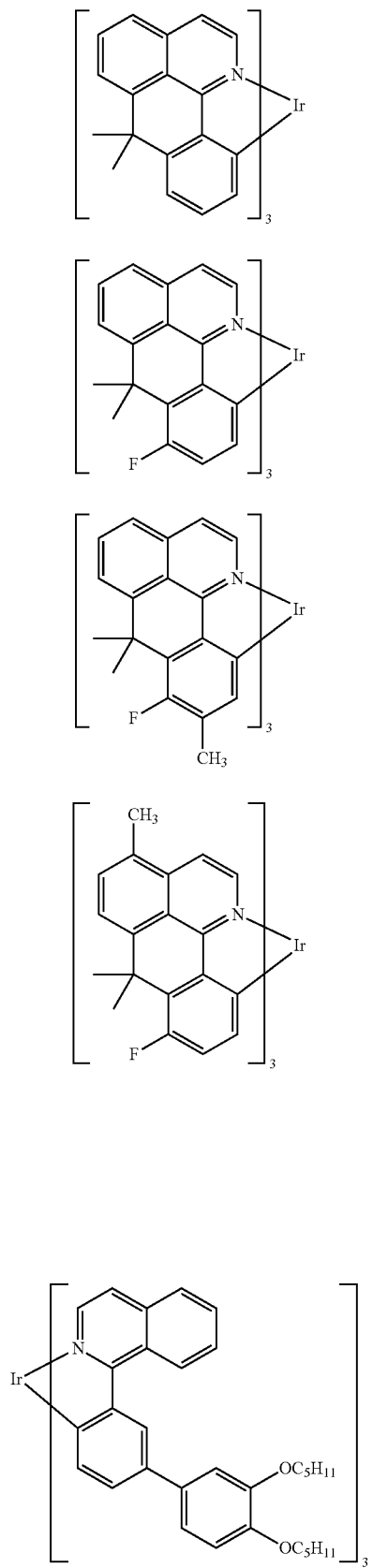
TABLE 4-continued
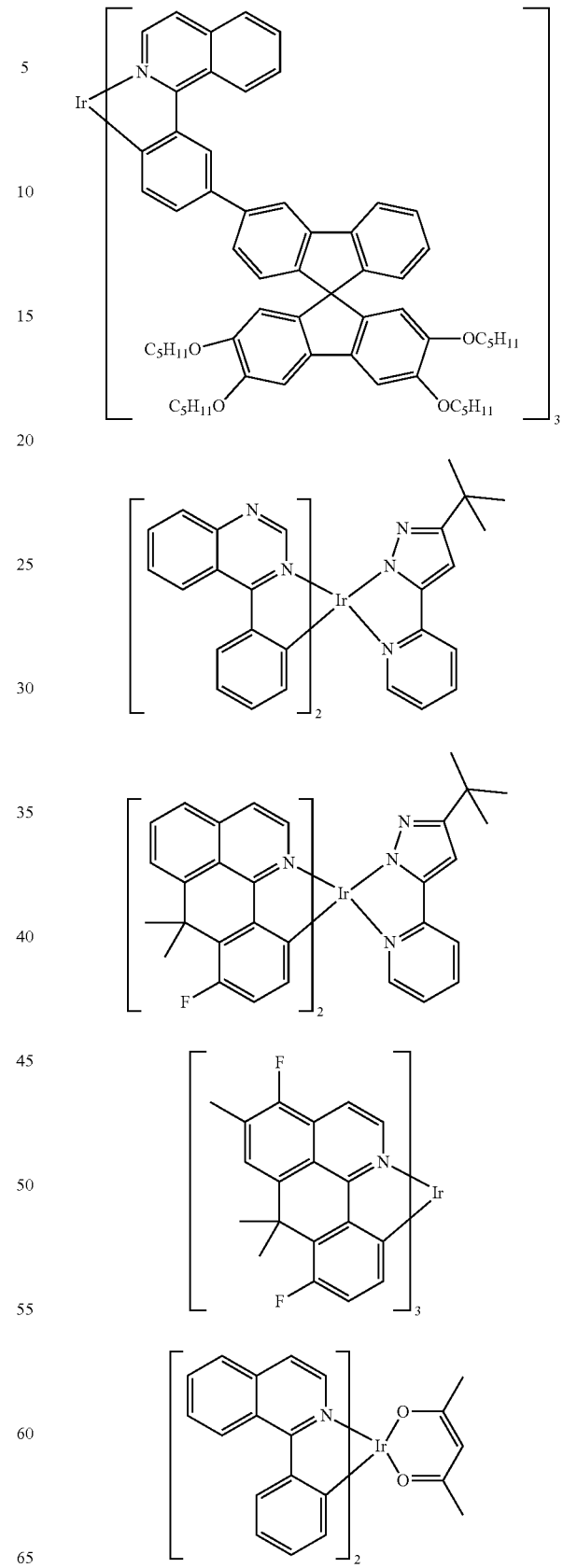

TABLE 4-continued
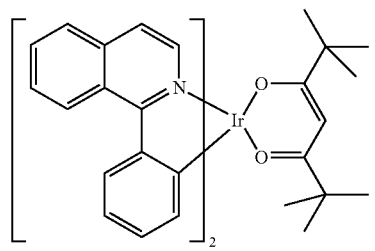
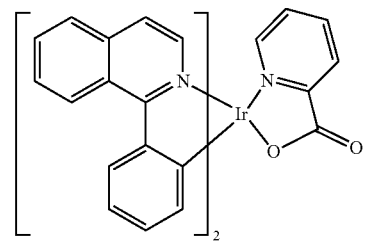
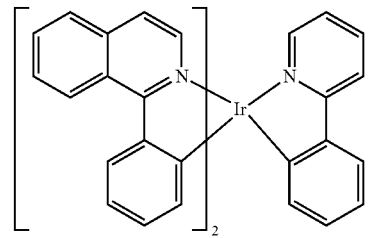
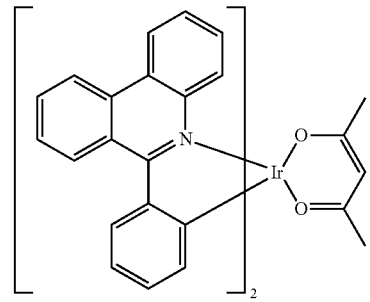
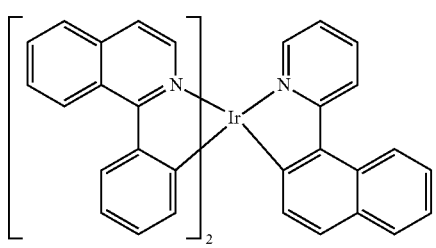
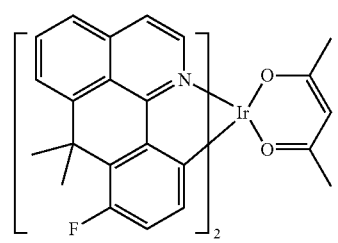
TABLE 4-continued
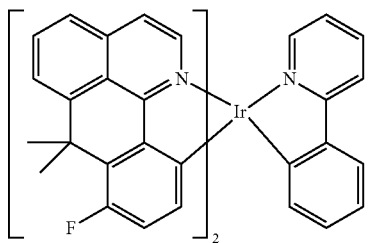
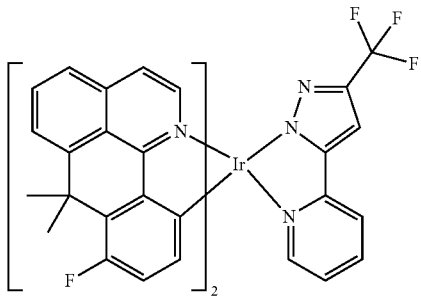
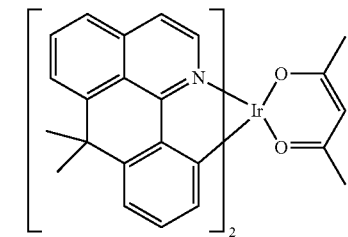
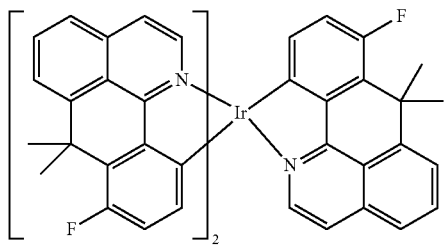
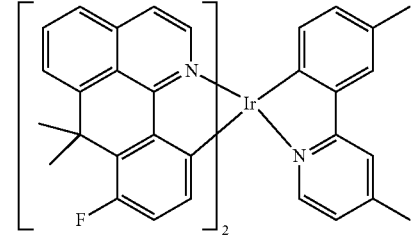
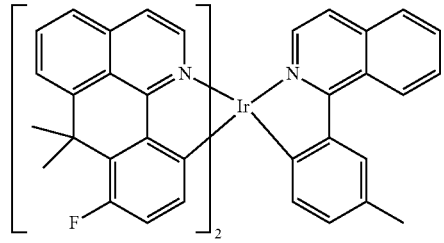

TABLE 4-continued
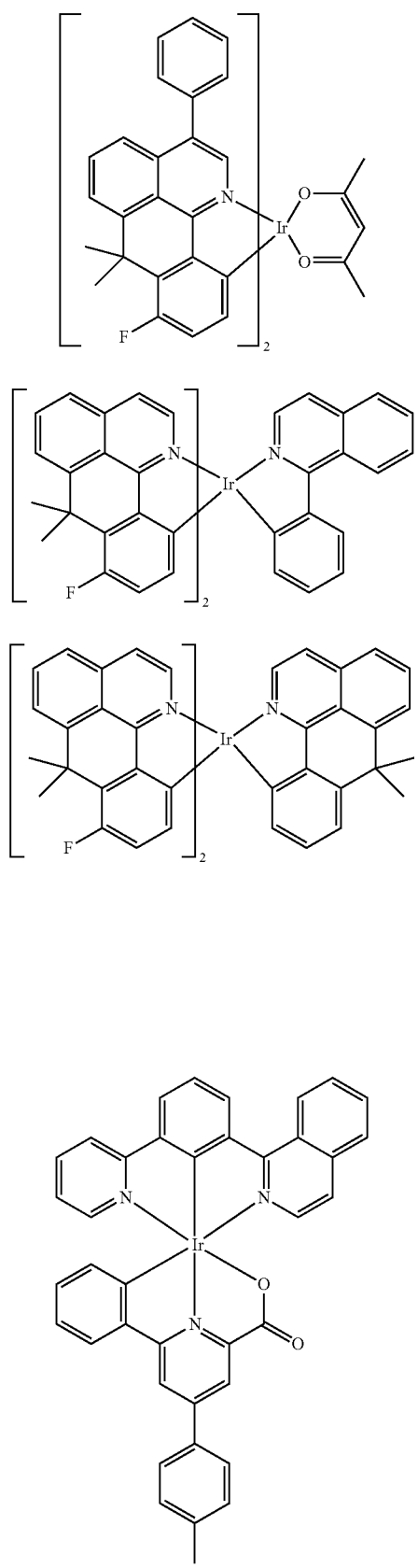
TABLE 4-continued
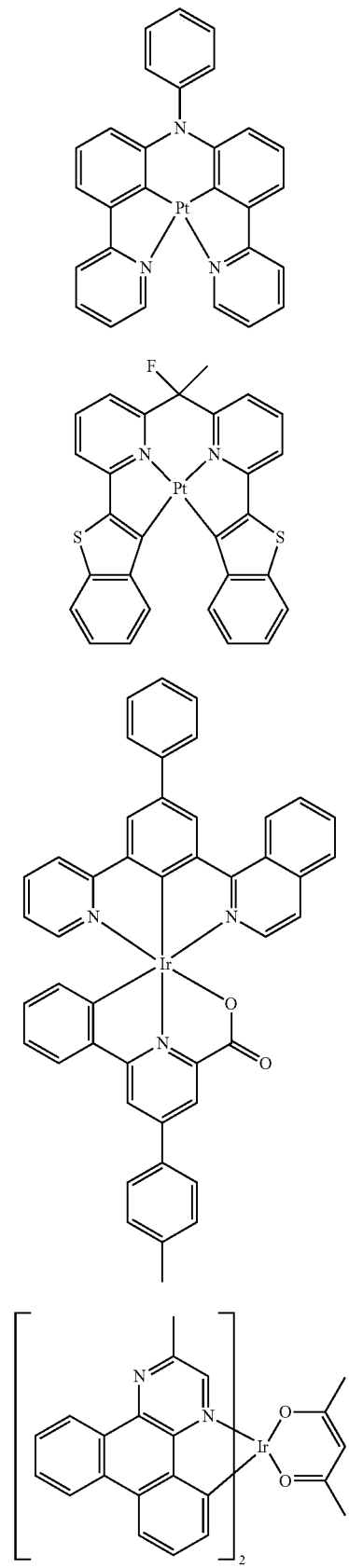

TABLE 4-continued
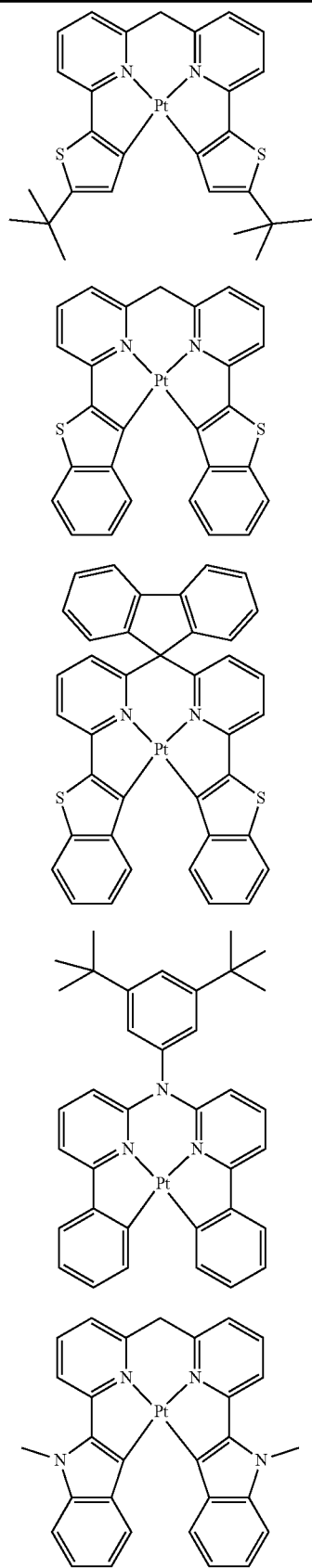
TABLE 4-continued
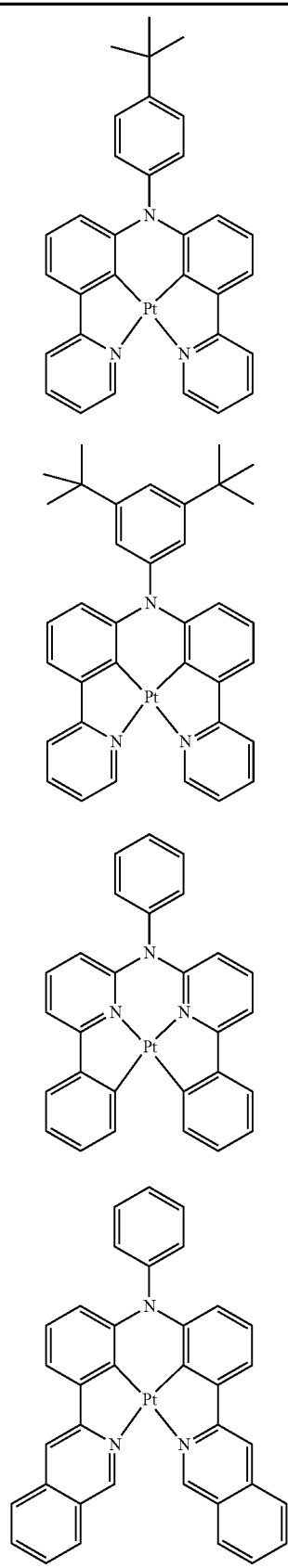

TABLE 4-continued
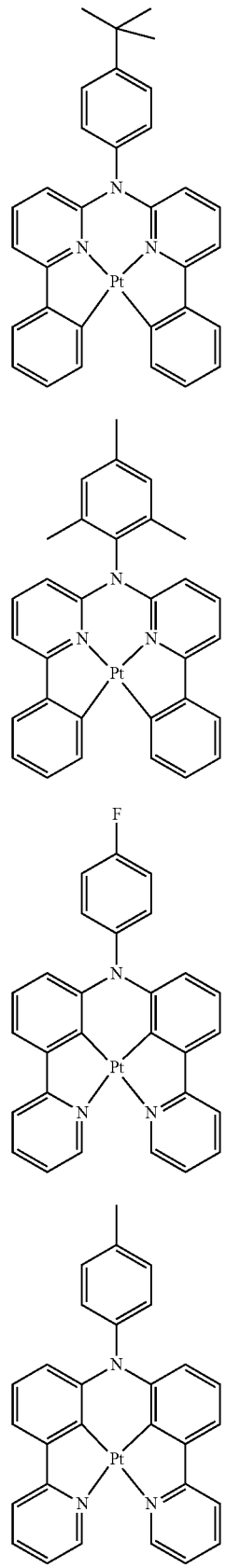
TABLE 4-continued
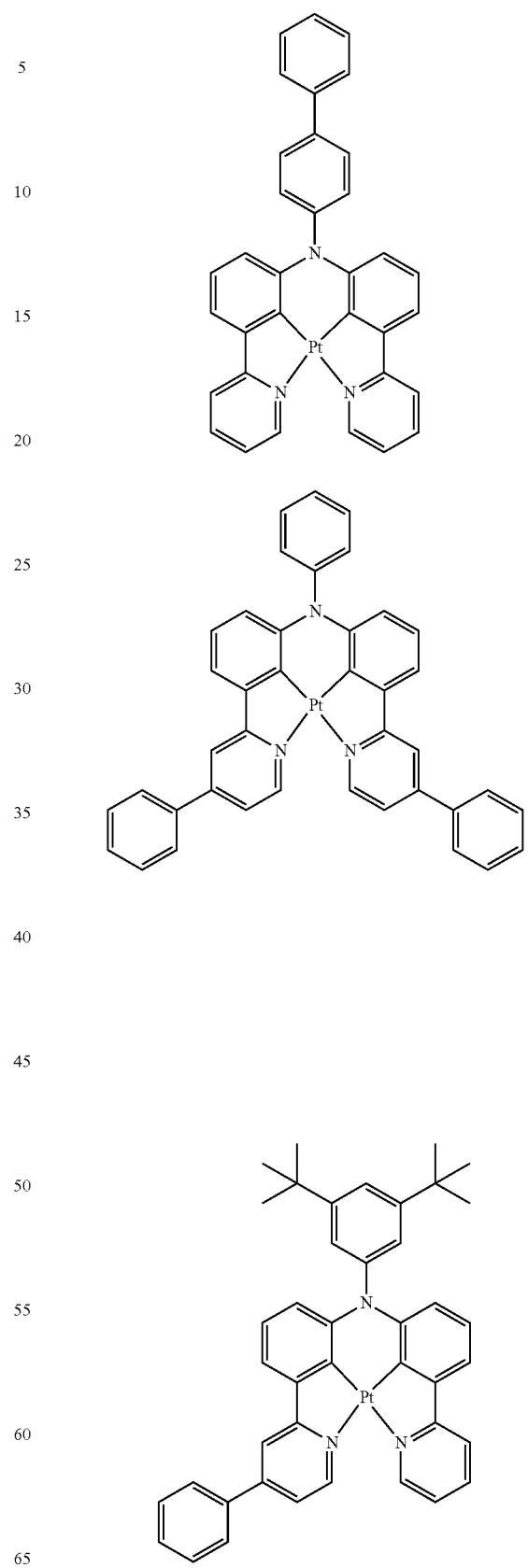

TABLE 4-continued
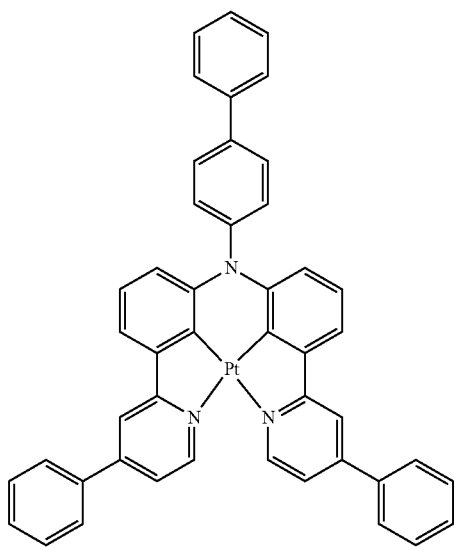
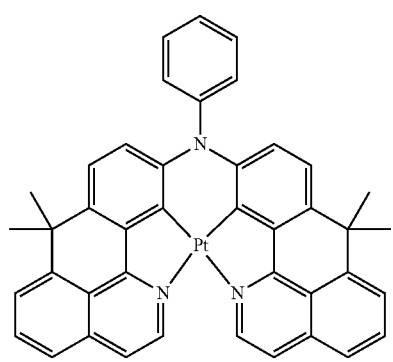
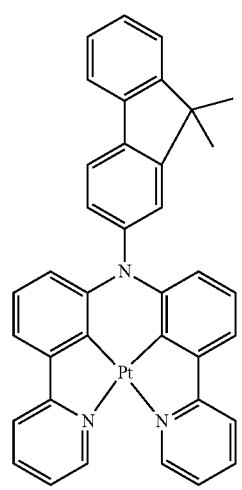
TABLE 4-continued
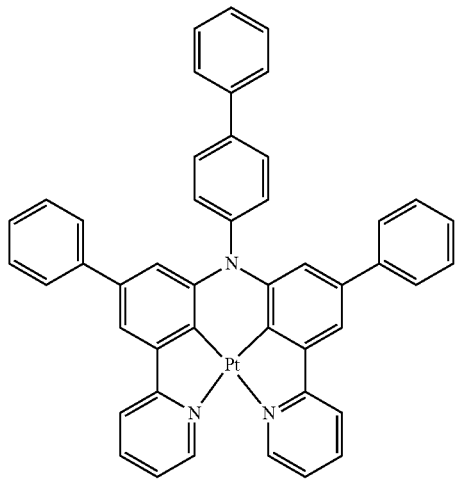
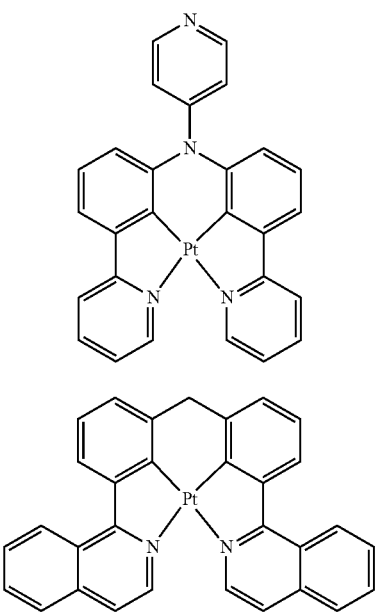
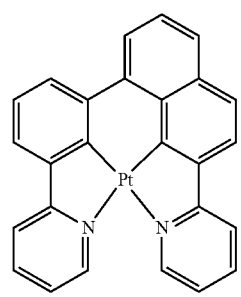

TABLE 4-continued
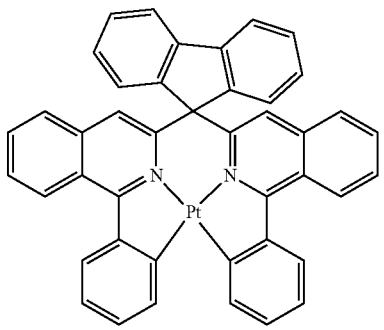
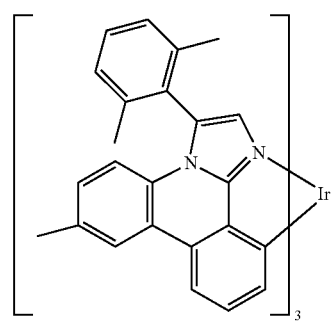
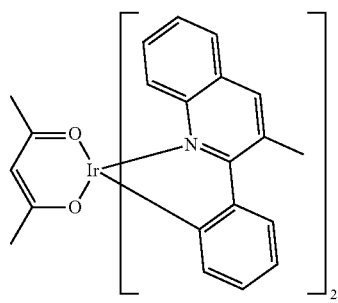
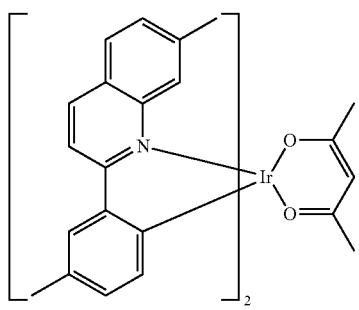
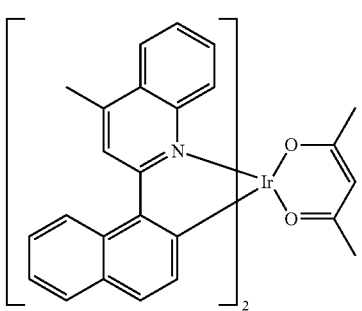
TABLE 4-continued
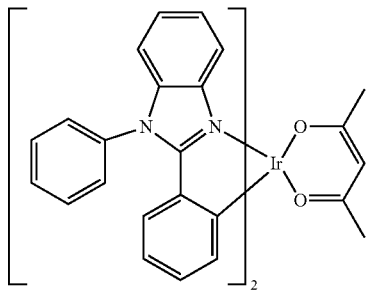
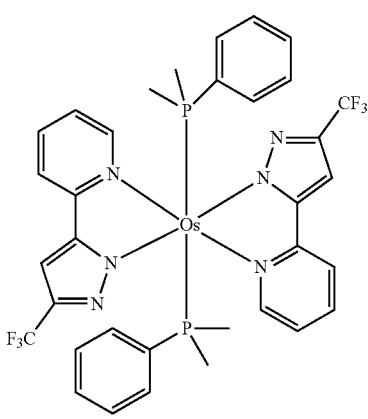
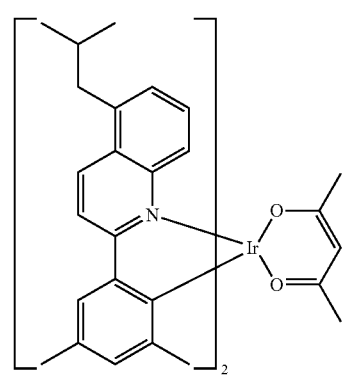
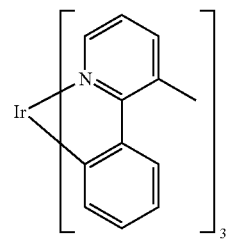
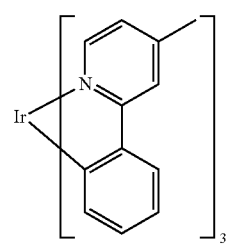

TABLE 4-continued
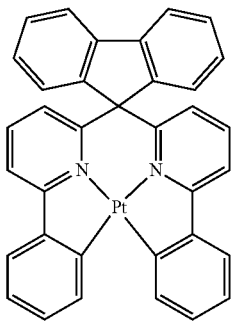
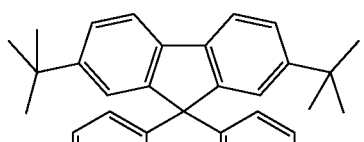
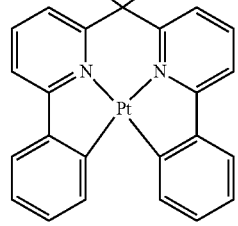
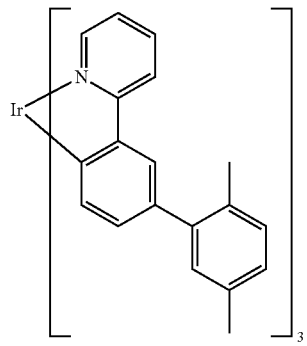
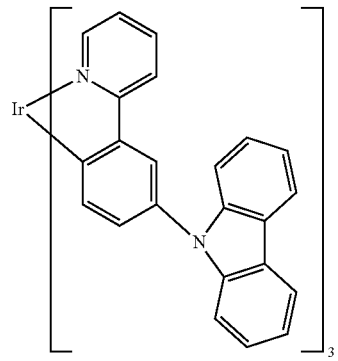
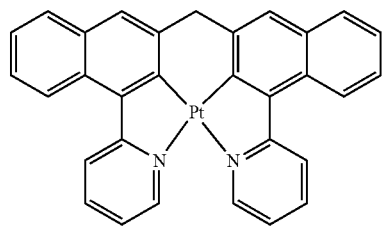
TABLE 4-continued
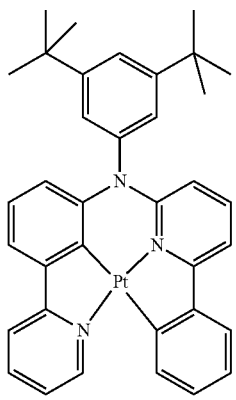
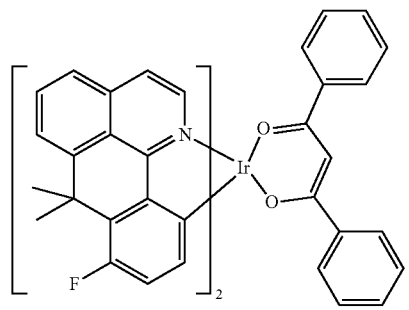
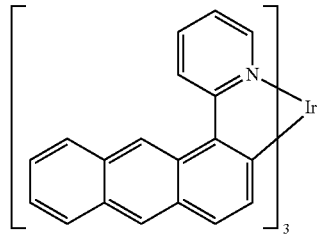
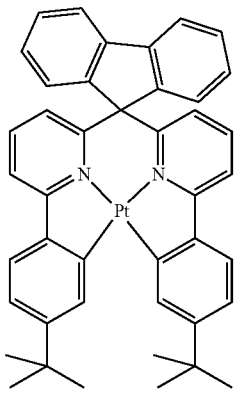

TABLE 4-continued
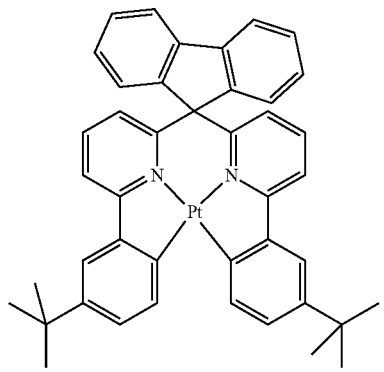
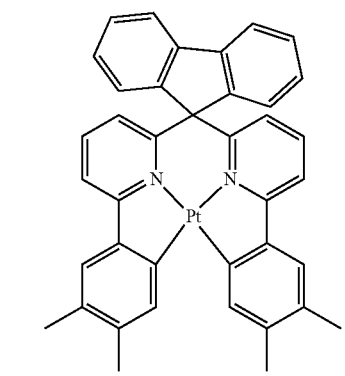
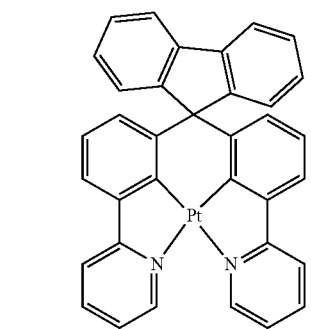
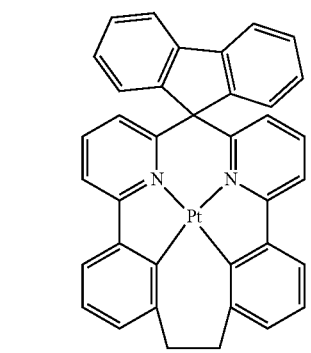
TABLE 4-continued
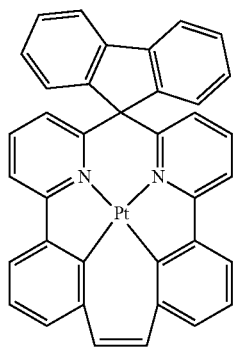
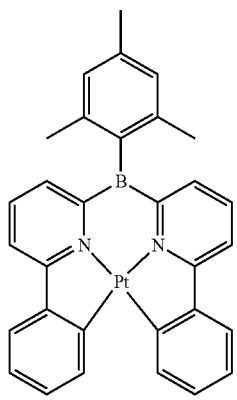
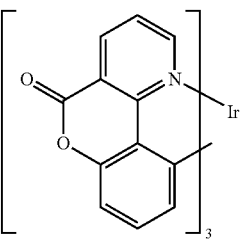
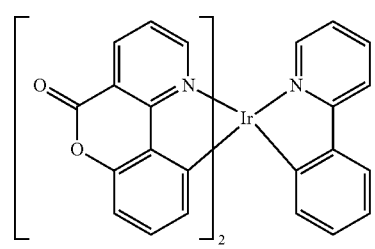
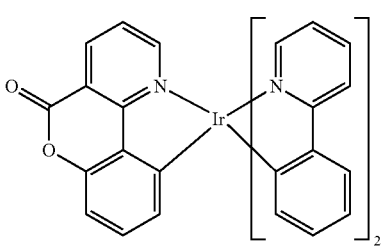

TABLE 4-continued
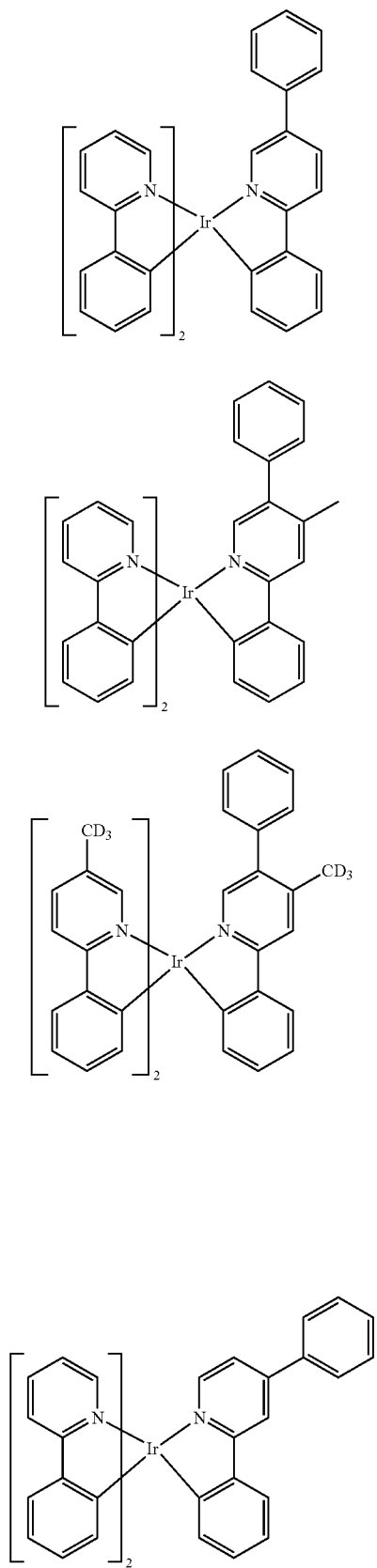
TABLE 4-continued
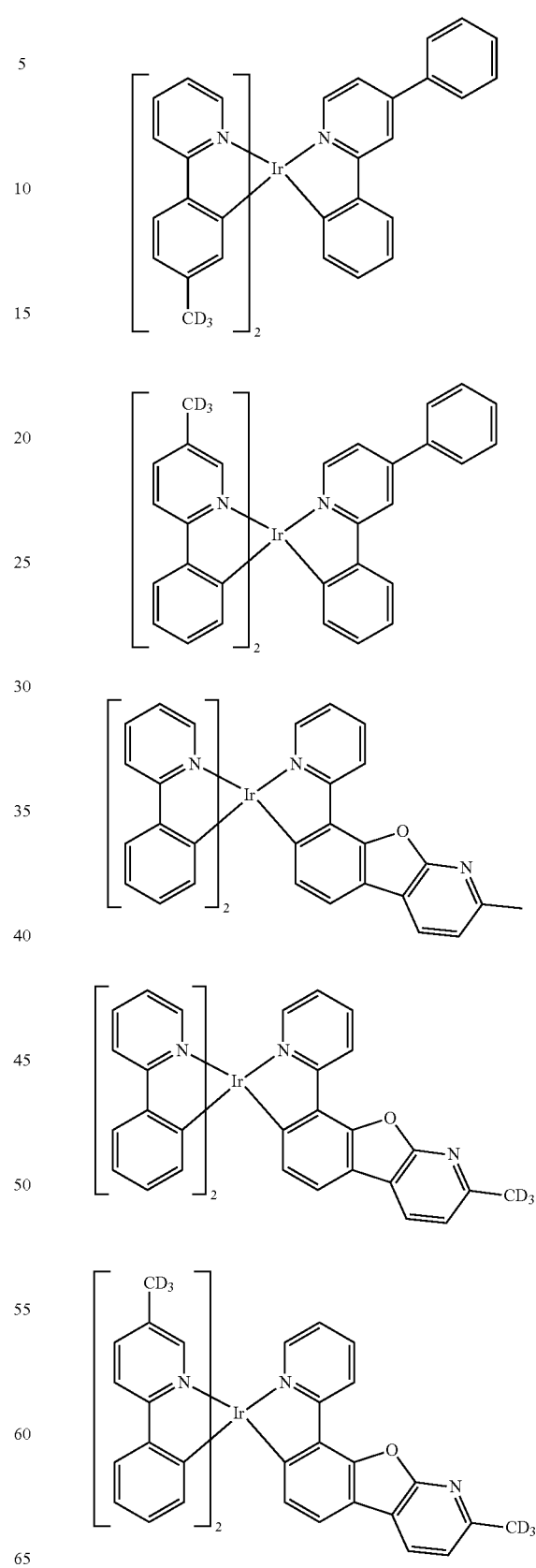

TABLE 4-continued

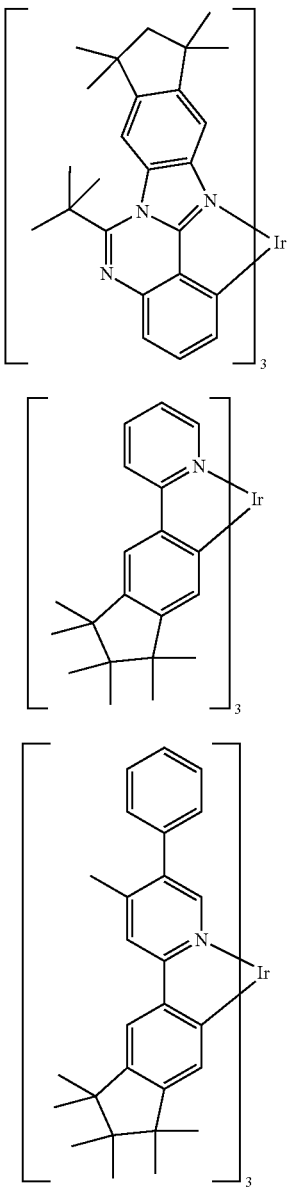

TABLE 4-continued

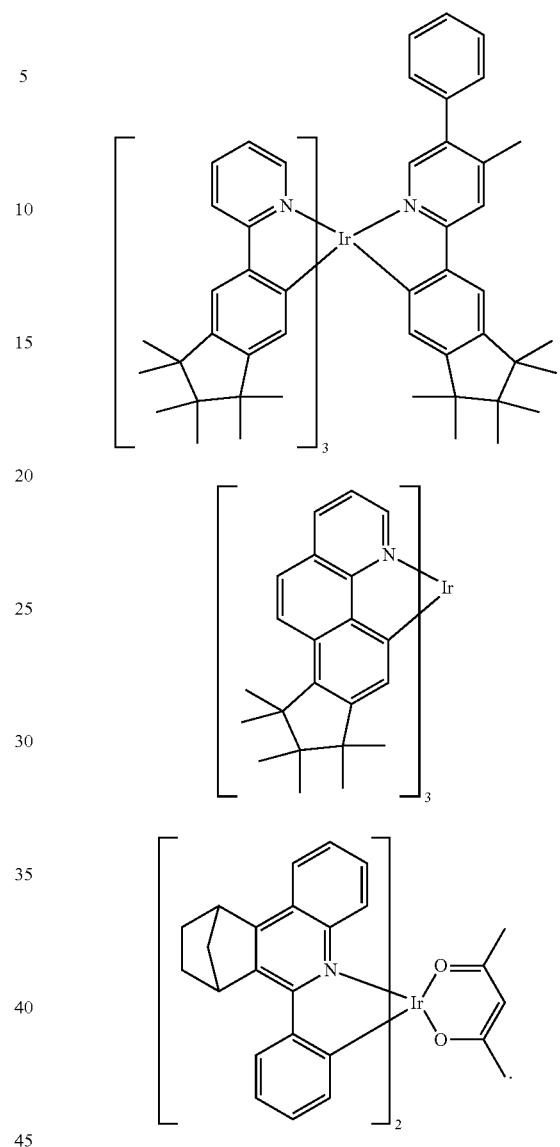

Preferred examples of phosphorescent polypodal emitters are listed in Table 5 below.

TABLE 5

| | | | |
|---|---|---|---|
| CAS-1269508-30-6 | CAS-1989601-68-4 | CAS-1989602-19-8 | CAS-1989602-70-1 |
| CAS-1215692-34-4 | CAS-1989601-69-5 | CAS-1989602-20-1 | CAS-1989602-71-2 |
| CAS-1370364-40-1 | CAS-1989601-70-8 | CAS-1989602-21-2 | CAS-1989602-72-3 |
| CAS-1370364-42-3 | CAS-1989601-71-9 | CAS-1989602-22-3 | CAS-1989602-73-4 |
| CAS-1989600-74-9 | CAS-1989601-72-0 | CAS-1989602-23-4 | CAS-1989602-74-5 |
| CAS-1989600-75-0 | CAS-1989601-73-1 | CAS-1989602-24-5 | CAS-1989602-75-6 |
| CAS-1989600-77-2 | CAS-1989601-74-2 | CAS-1989602-25-6 | CAS-1989602-76-7 |
| CAS-1989600-78-3 | CAS-1989601-75-3 | CAS-1989602-26-7 | CAS-1989602-77-8 |
| CAS-1989600-79-4 | CAS-1989601-76-4 | CAS-1989602-27-8 | CAS-1989602-78-9 |
| CAS-1989600-82-9 | CAS-1989601-77-5 | CAS-1989602-28-9 | CAS-1989602-79-0 |
| CAS-1989600-83-0 | CAS-1989601-78-6 | CAS-1989602-29-0 | CAS-1989602-80-3 |
| CAS-1989600-84-1 | CAS-1989601-79-7 | CAS-1989602-30-3 | CAS-1989602-82-5 |
| CAS-1989600-85-2 | CAS-1989601-80-0 | CAS-1989602-31-4 | CAS-1989602-84-7 |
| CAS-1989600-86-3 | CAS-1989601-81-1 | CAS-1989602-32-5 | CAS-1989602-85-8 |
| CAS-1989600-87-4 | CAS-1989601-82-2 | CAS-1989602-33-6 | CAS-1989602-86-9 |
| CAS-1989600-88-5 | CAS-1989601-83-3 | CAS-1989602-34-7 | CAS-1989602-87-0 |
| CAS-1989600-89-6 | CAS-1989601-84-4 | CAS-1989602-35-8 | CAS-1989602-88-1 |
| CAS-1989601-11-7 | CAS-1989601-85-5 | CAS-1989602-36-9 | CAS-1989604-00-3 |
| CAS-1989601-23-1 | CAS-1989601-86-6 | CAS-1989602-37-0 | CAS-1989604-01-4 |

TABLE 5-continued

| | | | |
|---|---|---|---|
| CAS-1989601-26-4 | CAS-1989601-87-7 | CAS-1989602-38-1 | CAS-1989604-02-5 |
| CAS-1989601-28-6 | CAS-1989601-88-8 | CAS-1989602-39-2 | CAS-1989604-03-6 |
| CAS-1989601-29-7 | CAS-1989601-89-9 | CAS-1989602-40-5 | CAS-1989604-04-7 |
| CAS-1989601-33-3 | CAS-1989601-90-2 | CAS-1989602-41-6 | CAS-1989604-05-8 |
| CAS-1989601-40-2 | CAS-1989601-91-3 | CAS-1989602-42-7 | CAS-1989604-06-9 |
| CAS-1989601-41-3 | CAS-1989601-92-4 | CAS-1989602-43-8 | CAS-1989604-07-0 |
| CAS-1989601-42-4 | CAS-1989601-93-5 | CAS-1989602-44-9 | CAS-1989604-08-1 |
| CAS-1989601-43-5 | CAS-1989601-94-6 | CAS-1989602-45-0 | CAS-1989604-09-2 |
| CAS-1989601-44-6 | CAS-1989601-95-7 | CAS-1989602-46-1 | CAS-1989604-10-5 |
| CAS-1989601-45-7 | CAS-1989601-96-8 | CAS-1989602-47-2 | CAS-1989604-11-6 |
| CAS-1989601-46-8 | CAS-1989601-97-9 | CAS-1989602-48-3 | CAS-1989604-13-8 |
| CAS-1989601-47-9 | CAS-1989601-98-0 | CAS-1989602-49-4 | CAS-1989604-14-9 |
| CAS-1989601-48-0 | CAS-1989601-99-1 | CAS-1989602-50-7 | CAS-1989604-15-0 |
| CAS-1989601-49-1 | CAS-1989602-00-7 | CAS-1989602-51-8 | CAS-1989604-16-1 |
| CAS-1989601-50-4 | CAS-1989602-01-8 | CAS-1989602-52-9 | CAS-1989604-17-2 |
| CAS-1989601-51-5 | CAS-1989602-02-9 | CAS-1989602-53-0 | CAS-1989604-18-3 |
| CAS-1989601-52-6 | CAS-1989602-03-0 | CAS-1989602-54-1 | CAS-1989604-19-4 |
| CAS-1989601-53-7 | CAS-1989602-04-1 | CAS-1989602-55-2 | CAS-1989604-20-7 |
| CAS-1989601-54-8 | CAS-1989602-05-2 | CAS-1989602-56-3 | CAS-1989604-21-8 |
| CAS-1989601-55-9 | CAS-1989602-06-3 | CAS-1989602-57-4 | CAS-1989604-22-9 |
| CAS-1989601-56-0 | CAS-1989602-07-4 | CAS-1989602-58-5 | CAS-1989604-23-0 |
| CAS-1989601-57-1 | CAS-1989602-08-5 | CAS-1989602-59-6 | CAS-1989604-24-1 |
| CAS-1989601-58-2 | CAS-1989602-09-6 | CAS-1989602-60-9 | CAS-1989604-25-2 |
| CAS-1989601-59-3 | CAS-1989602-10-9 | CAS-1989602-61-0 | CAS-1989604-26-3 |
| CAS-1989601-60-6 | CAS-1989602-11-0 | CAS-1989602-62-1 | CAS-1989604-27-4 |
| CAS-1989601-61-7 | CAS-1989602-12-1 | CAS-1989602-63-2 | CAS-1989604-28-5 |
| CAS-1989601-62-8 | CAS-1989602-13-2 | CAS-1989602-64-3 | CAS-1989604-29-6 |
| CAS-1989601-63-9 | CAS-1989602-14-3 | CAS-1989602-65-4 | CAS-1989604-30-9 |
| CAS-1989601-64-0 | CAS-1989602-15-4 | CAS-1989602-66-5 | CAS-1989604-31-0 |
| CAS-1989601-65-1 | CAS-1989602-16-5 | CAS-1989602-67-6 | CAS-1989604-32-1 |
| CAS-1989601-66-2 | CAS-1989602-17-6 | CAS-1989602-68-7 | CAS-1989604-33-2 |
| CAS-1989601-67-3 | CAS-1989602-18-7 | CAS-1989602-69-8 | CAS-1989604-34-3 |
| CAS-1989604-35-4 | CAS-1989604-88-7 | CAS-1989605-52-8 | CAS-1989606-07-6 |
| CAS-1989604-36-5 | CAS-1989604-89-8 | CAS-1989605-53-9 | CAS-1989606-08-7 |
| CAS-1989604-37-6 | CAS-1989604-90-1 | CAS-1989605-54-0 | CAS-1989606-09-8 |
| CAS-1989604-38-7 | CAS-1989604-92-3 | CAS-1989605-55-1 | CAS-1989606-10-1 |
| CAS-1989604-39-8 | CAS-1989604-93-4 | CAS-1989605-56-2 | CAS-1989606-11-2 |
| CAS-1989604-40-1 | CAS-1989604-94-5 | CAS-1989605-57-3 | CAS-1989606-12-3 |
| CAS-1989604-41-2 | CAS-1989604-95-6 | CAS-1989605-58-4 | CAS-1989606-13-4 |
| CAS-1989604-42-3 | CAS-1989604-96-7 | CAS-1989605-59-5 | CAS-1989606-14-5 |
| CAS-1989604-43-4 | CAS-1989604-97-8 | CAS-1989605-61-9 | CAS-1989606-15-6 |
| CAS-1989604-45-6 | CAS-1989605-09-5 | CAS-1989605-62-0 | CAS-1989606-16-7 |
| CAS-1989604-46-7 | CAS-1989605-10-8 | CAS-1989605-63-1 | CAS-1989606-17-8 |
| CAS-1989604-47-8 | CAS-1989605-11-9 | CAS-1989605-64-2 | CAS-1989606-18-9 |
| CAS-1989604-48-9 | CAS-1989605-13-1 | CAS-1989605-65-3 | CAS-1989606-19-0 |
| CAS-1989604-49-0 | CAS-1989605-14-2 | CAS-1989605-66-4 | CAS-1989606-20-3 |
| CAS-1989604-50-3 | CAS-1989605-15-3 | CAS-1989605-67-5 | CAS-1989606-21-4 |
| CAS-1989604-52-5 | CAS-1989605-16-4 | CAS-1989605-68-6 | CAS-1989606-22-5 |
| CAS-1989604-53-6 | CAS-1989605-17-5 | CAS-1989605-69-7 | CAS-1989606-23-6 |
| CAS-1989604-54-7 | CAS-1989605-18-6 | CAS-1989605-70-0 | CAS-1989606-24-7 |
| CAS-1989604-55-8 | CAS-1989605-19-7 | CAS-1989605-71-1 | CAS-1989606-26-9 |
| CAS-1989604-56-9 | CAS-1989605-20-0 | CAS-1989605-72-2 | CAS-1989606-27-0 |
| CAS-1989604-57-0 | CAS-1989605-21-1 | CAS-1989605-73-3 | CAS-1989606-28-1 |
| CAS-1989604-58-1 | CAS-1989605-22-2 | CAS-1989605-74-4 | CAS-1989606-29-2 |
| CAS-1989604-59-2 | CAS-1989605-23-3 | CAS-1989605-75-5 | CAS-1989606-30-5 |
| CAS-1989604-60-5 | CAS-1989605-24-4 | CAS-1989605-76-6 | CAS-1989606-31-6 |
| CAS-1989604-61-6 | CAS-1989605-25-5 | CAS-1989605-77-7 | CAS-1989606-32-7 |
| CAS-1989604-62-7 | CAS-1989605-26-6 | CAS-1989605-78-8 | CAS-1989606-33-8 |
| CAS-1989604-63-8 | CAS-1989605-27-7 | CAS-1989605-79-9 | CAS-1989606-34-9 |
| CAS-1989604-64-9 | CAS-1989605-28-8 | CAS-1989605-81-3 | CAS-1989606-35-0 |
| CAS-1989604-65-0 | CAS-1989605-29-9 | CAS-1989605-82-4 | CAS-1989606-36-1 |
| CAS-1989604-66-1 | CAS-1989605-30-2 | CAS-1989605-83-5 | CAS-1989606-37-2 |
| CAS-1989604-67-2 | CAS-1989605-31-3 | CAS-1989605-84-6 | CAS-1989606-38-3 |
| CAS-1989604-68-3 | CAS-1989605-32-4 | CAS-1989605-85-7 | CAS-1989606-39-4 |
| CAS-1989604-69-4 | CAS-1989605-33-5 | CAS-1989605-86-8 | CAS-1989606-40-7 |
| CAS-1989604-70-7 | CAS-1989605-34-6 | CAS-1989605-87-9 | CAS-1989606-41-8 |
| CAS-1989604-71-8 | CAS-1989605-35-7 | CAS-1989605-88-0 | CAS-1989606-42-9 |
| CAS-1989604-72-9 | CAS-1989605-36-8 | CAS-1989605-89-1 | CAS-1989606-43-0 |
| CAS-1989604-73-0 | CAS-1989605-37-9 | CAS-1989605-90-4 | CAS-1989606-44-1 |
| CAS-1989604-74-1 | CAS-1989605-38-0 | CAS-1989605-91-5 | CAS-1989606-45-2 |
| CAS-1989604-75-2 | CAS-1989605-39-1 | CAS-1989605-92-6 | CAS-1989606-46-3 |
| CAS-1989604-76-3 | CAS-1989605-40-4 | CAS-1989605-93-7 | CAS-1989606-48-5 |
| CAS-1989604-77-4 | CAS-1989605-41-5 | CAS-1989605-94-8 | CAS-1989606-49-6 |
| CAS-1989604-78-5 | CAS-1989605-42-6 | CAS-1989605-95-9 | CAS-1989606-53-2 |
| CAS-1989604-79-6 | CAS-1989605-43-7 | CAS-1989605-96-0 | CAS-1989606-55-4 |
| CAS-1989604-80-9 | CAS-1989605-44-8 | CAS-1989605-97-1 | CAS-1989606-56-5 |
| CAS-1989604-81-0 | CAS-1989605-45-9 | CAS-1989605-98-2 | CAS-1989606-61-2 |
| CAS-1989604-82-1 | CAS-1989605-46-0 | CAS-1989605-99-3 | CAS-1989606-62-3 |
| CAS-1989604-83-2 | CAS-1989605-47-1 | CAS-1989606-00-9 | CAS-1989606-63-4 |
| CAS-1989604-84-3 | CAS-1989605-48-2 | CAS-1989606-01-0 | CAS-1989606-67-8 |

TABLE 5-continued

| | | | |
|---|---|---|---|
| CAS-1989604-85-4 | CAS-1989605-49-3 | CAS-1989606-04-3 | CAS-1989606-69-0 |
| CAS-1989604-86-5 | CAS-1989605-50-6 | CAS-1989606-05-4 | CAS-1989606-70-3 |
| CAS-1989604-87-6 | CAS-1989605-51-7 | CAS-1989606-06-5 | CAS-1989606-74-7 |
| CAS-1989658-39-0 | CAS-2088184-56-7 | CAS-2088185-07-1 | CAS-2088185-66-2 |
| CAS-1989658-41-4 | CAS-2088184-57-8 | CAS-2088185-08-2 | CAS-2088185-67-3 |
| CAS-1989658-43-6 | CAS-2088184-58-9 | CAS-2088185-09-3 | CAS-2088185-68-4 |
| CAS-1989658-47-0 | CAS-2088184-59-0 | CAS-2088185-10-6 | CAS-2088185-69-5 |
| CAS-1989658-49-2 | CAS-2088184-60-3 | CAS-2088185-11-7 | CAS-2088185-70-8 |
| CAS-2088184-07-8 | CAS-2088184-61-4 | CAS-2088185-12-8 | CAS-2088185-71-9 |
| CAS-2088184-08-9 | CAS-2088184-62-5 | CAS-2088185-13-9 | CAS-2088185-72-0 |
| CAS-2088184-09-0 | CAS-2088184-63-6 | CAS-2088185-14-0 | CAS-2088185-73-1 |
| CAS-2088184-10-3 | CAS-2088184-64-7 | CAS-2088185-15-1 | CAS-2088185-74-2 |
| CAS-2088184-11-4 | CAS-2088184-65-8 | CAS-2088185-16-2 | CAS-2088185-75-3 |
| CAS-2088184-13-6 | CAS-2088184-66-9 | CAS-2088185-17-3 | CAS-2088185-76-4 |
| CAS-2088184-14-7 | CAS-2088184-67-0 | CAS-2088185-18-4 | CAS-2088185-77-5 |
| CAS-2088184-15-8 | CAS-2088184-68-1 | CAS-2088185-19-5 | CAS-2088185-78-6 |
| CAS-2088184-16-9 | CAS-2088184-69-2 | CAS-2088185-20-8 | CAS-2088185-79-7 |
| CAS-2088184-17-0 | CAS-2088184-70-5 | CAS-2088185-21-9 | CAS-2088185-80-0 |
| CAS-2088184-18-1 | CAS-2088184-71-6 | CAS-2088185-22-0 | CAS-2088185-81-1 |
| CAS-2088184-19-2 | CAS-2088184-72-7 | CAS-2088185-23-1 | CAS-2088185-82-2 |
| CAS-2088184-20-5 | CAS-2088184-73-8 | CAS-2088185-32-2 | CAS-2088185-83-3 |
| CAS-2088184-21-6 | CAS-2088184-74-9 | CAS-2088185-33-3 | CAS-2088185-84-4 |
| CAS-2088184-22-7 | CAS-2088184-75-0 | CAS-2088185-34-4 | CAS-2088185-85-5 |
| CAS-2088184-23-8 | CAS-2088184-76-1 | CAS-2088185-35-5 | CAS-2088185-86-6 |
| CAS-2088184-24-9 | CAS-2088184-77-2 | CAS-2088185-36-6 | CAS-2088185-87-7 |
| CAS-2088184-25-0 | CAS-2088184-78-3 | CAS-2088185-37-7 | CAS-2088185-88-8 |
| CAS-2088184-26-1 | CAS-2088184-79-4 | CAS-2088185-38-8 | CAS-2088185-89-9 |
| CAS-2088184-27-2 | CAS-2088184-80-7 | CAS-2088185-39-9 | CAS-2088185-90-2 |
| CAS-2088184-28-3 | CAS-2088184-81-8 | CAS-2088185-40-2 | CAS-2088185-91-3 |
| CAS-2088184-29-4 | CAS-2088184-82-9 | CAS-2088185-41-3 | CAS-2088185-92-4 |
| CAS-2088184-30-7 | CAS-2088184-83-0 | CAS-2088185-42-4 | CAS-2088185-93-5 |
| CAS-2088184-32-9 | CAS-2088184-84-1 | CAS-2088185-43-5 | CAS-2088185-94-6 |
| CAS-2088184-34-1 | CAS-2088184-85-2 | CAS-2088185-44-6 | CAS-2088185-95-7 |
| CAS-2088184-35-2 | CAS-2088184-86-3 | CAS-2088185-45-7 | CAS-2088185-96-8 |
| CAS-2088184-36-3 | CAS-2088184-87-4 | CAS-2088185-46-8 | CAS-2088185-97-9 |
| CAS-2088184-37-4 | CAS-2088184-88-5 | CAS-2088185-47-9 | CAS-2088185-98-0 |
| CAS-2088184-38-5 | CAS-2088184-89-6 | CAS-2088185-48-0 | CAS-2088185-99-1 |
| CAS-2088184-39-6 | CAS-2088184-90-9 | CAS-2088185-49-1 | CAS-2088186-00-7 |
| CAS-2088184-40-9 | CAS-2088184-91-0 | CAS-2088185-50-4 | CAS-2088186-01-8 |
| CAS-2088184-41-0 | CAS-2088184-92-1 | CAS-2088185-51-5 | CAS-2088186-02-9 |
| CAS-2088184-42-1 | CAS-2088184-93-2 | CAS-2088185-52-6 | CAS-2088195-88-2 |
| CAS-2088184-43-2 | CAS-2088184-94-3 | CAS-2088185-53-7 | CAS-2088195-89-3 |
| CAS-2088184-44-3 | CAS-2088184-95-4 | CAS-2088185-54-8 | CAS-2088195-90-6 |
| CAS-2088184-45-4 | CAS-2088184-96-5 | CAS-2088185-55-9 | CAS-2088195-91-7 |
| CAS-2088184-46-5 | CAS-2088184-97-6 | CAS-2088185-56-0 | CAS-861806-70-4 |
| CAS-2088184-47-6 | CAS-2088184-98-7 | CAS-2088185-57-1 | CAS-1269508-30-6 |
| CAS-2088184-48-7 | CAS-2088184-99-8 | CAS-2088185-58-2 | |
| CAS-2088184-49-8 | CAS-2088185-00-4 | CAS-2088185-59-3 | |
| CAS-2088184-50-1 | CAS-2088185-01-5 | CAS-2088185-60-6 | |
| CAS-2088184-51-2 | CAS-2088185-02-6 | CAS-2088185-61-7 | |
| CAS-2088184-52-3 | CAS-2088185-03-7 | CAS-2088185-62-8 | |
| CAS-2088184-53-4 | CAS-2088185-04-8 | CAS-2088185-63-9 | |
| CAS-2088184-54-5 | CAS-2088185-05-9 | CAS-2088185-64-0 | |
| CAS-2088184-55-6 | CAS-2088185-06-0 | CAS-2088185-65-1 | |

In the composition of the invention, preferably any mixture M1, M2, M3, M4, M5, M6, M7, M8, M9, M10, M11, M12, M13, M14, M15, M16, M17, M18, M19, M20, M21, M22, M23, M24, M25, M26, M27, M28, M29, M30, M31, M32, M33, M34, M35, M36, M37, M38, M39, M40, M41, M42, M43, M44, M45, M46, M47, M48, M49, M50, M51, M52, M53, M54, M55, M56, M57, M58, M59, M60, M61, M62, M63, M64, M65, M66, M67, M68, M69, M70, M71 or M72 is combined with a compound from Table 4 or 5.

The composition of the invention comprising at least one phosphorescent emitter preferably forms an infrared-emitting or yellow-, orange-, red-, green-, blue- or ultraviolet-emitting layer, more preferably a green-emitting layer.

A yellow-emitting layer is understood here to mean a layer having a photoluminescence maximum within the range from 540 to 570 nm. An orange-emitting layer is understood to mean a layer having a photoluminescence maximum within the range from 570 to 600 nm. A red-emitting layer is understood to mean a layer having a photoluminescence maximum within the range from 600 to 750 nm. A green-emitting layer is understood to mean a layer having a photoluminescence maximum within the range from 490 to 540 nm. A blue-emitting layer is understood to mean a layer having a photoluminescence maximum within the range from 440 to 490 nm. The photoluminescence maximum of the layer is determined here by measuring the photoluminescence spectrum of the layer having a layer thickness of 50 nm at room temperature, said layer having the composition of the invention, i.e. comprising emitter and matrix.

The photoluminescence spectrum of the layer is recorded, for example, with a commercial photoluminescence spectrometer.

The photoluminescence spectrum of the emitter chosen is generally measured in oxygen-free solution, $10^{-5}$ molar, generally at room temperature, a suitable solvent being any in which the chosen emitter dissolves in the concentration mentioned. Particularly suitable solvents are typically toluene or 2-methyl-THF, but also dichloromethane. Measurement is effected with a commercial photoluminescence spectrometer. The triplet energy T1 in eV is determined from the photoluminescence spectra of the emitters. Firstly, the peak maximum PImax. (in nm) of the photoluminescence spectrum is determined. The peak maximum PImax. (in nm) is then converted to eV by: E(T1 in eV)=1240/E(T1 in nm)=1240/PImax. (in nm).

Preferred phosphorescent emitters are accordingly infrared emitters, preferably from Table 4 or 5, the triplet energy $T_1$ of which is preferably ~1.9 eV to 1.0 eV.

Preferred phosphorescent emitters are accordingly red emitters, preferably from Table 4 or 5, the triplet energy $T_1$ of which is preferably ~2.1 eV to ~1.9 eV.

Preferred phosphorescent emitters are accordingly yellow emitters, preferably from Table 4 or 5, the triplet energy $T_1$ of which is preferably ~2.3 eV to ~2.1 eV.

Preferred phosphorescent emitters are accordingly green emitters, preferably from Table 4 or 5, the triplet energy $T_1$ of which is preferably ~2.5 eV to ~2.3 eV.

Preferred phosphorescent emitters are accordingly blue emitters, preferably from Table 4 or 5, the triplet energy $T_1$ of which is preferably ~3.1 eV to ~2.5 eV.

Preferred phosphorescent emitters are accordingly ultraviolet emitters, preferably from Table 4 or 5, the triplet energy $T_1$ of which is preferably ~4.0 eV to ~3.1 eV.

Particularly preferred phosphorescent emitters are accordingly green emitters, preferably from Table 4 or 5 as described above.

Very particularly preferred phosphorescent emitters are accordingly green emitters, preferably from Table 4 or 5, the triplet energy $T_1$ of which is preferably ~2.5 eV to ~2.3 eV.

Most preferably, green emitters, preferably from Table 4 or 5, as described above, are selected for the composition of the invention or emitting layer of the invention.

Preferred fluorescent emitters are selected from the class of the arylamines. An arylamine or an aromatic amine in the context of this invention is understood to mean a compound containing three substituted or unsubstituted aromatic or heteroaromatic ring systems bonded directly to the nitrogen. Preferably, at least one of these aromatic or heteroaromatic ring systems is a fused ring system, more preferably having at least 14 ring atoms. Preferred examples of these are aromatic anthraceneamines, aromatic anthracenediamines, aromatic pyreneamines, aromatic pyrenediamines, aromatic chryseneamines or aromatic chrysenediamines. An aromatic anthraceneamine is understood to mean a compound in which a diarylamino group is bonded directly to an anthracene group, preferably in the 9 position. An aromatic anthracenediamine is understood to mean a compound in which two diarylamino groups are bonded directly to an anthracene group, preferably in the 9,10 positions. Aromatic pyreneamines, pyrenediamines, chryseneamines and chrysenediamines are defined analogously, where the diarylamino groups are bonded to the pyrene preferably in the 1 position or 1,6 positions. Further preferred fluorescent emitters are indenofluoreneamines or -diamines, for example according to WO 2006/108497 or WO 2006/122630, benzoindenofluoreneamines or -diamines, for example according to WO 2008/006449, and dibenzoindenofluoreneamines or -diamines, for example according to WO 2007/140847, and the indenofluorene derivatives having fused aryl groups disclosed in WO 2010/012328.

In a further preferred embodiment of the invention, the composition of the invention is used as a component of mixed matrix systems. The mixed matrix systems preferably comprise three or four different matrix materials, more preferably three different matrix materials (in other words, one further matrix component in addition to the composition of the invention). Examples of suitable matrix materials which can be used in combination with the composition of the invention as matrix component(s) in a mixed matrix system are selected from wide band gap materials, electron transport materials (ETM) and hole transport materials (HTM).

Preference is given to using mixed matrix systems in phosphorescent organic electroluminescent devices. One source of more detailed information about mixed matrix systems is the application WO 2010/108579. Particularly suitable matrix materials which can be used in combination with the composition of the invention as matrix component(s) of a mixed matrix system in phosphorescent or fluorescent organic electroluminescent devices are selected from the preferred matrix materials specified below for phosphorescent emitters or the preferred matrix materials for fluorescent emitters, according to what type of emitter is used. Preferably, the mixed matrix system is optimized for an emitter from Table 4 or 5.

Various substance classes are useful as further host materials, preferably for fluorescent emitters, as well as the composition of the invention as described above, more preferably comprising a mixture of materials selected from M1 to M72. Preferred further host materials are selected from the classes of the oligoarylenes (e.g. 2,2',7,7'-tetraphenylspirobifluorene according to EP 676461 or dinaphthylanthracene), especially of the oligoarylenes containing fused aromatic groups, the oligoarylenevinylenes (e.g. DPVBi or spiro-DPVBi according to EP 676461), the polypodal metal complexes (for example according to WO 2004/081017), the hole-conducting compounds (for example according to WO 2004/058911), the electron-conducting compounds, especially ketones, phosphine oxides, sulfoxides, etc. (for example according to WO 2005/084081 and WO 2005/084082), the atropisomers (for example according to WO 2006/048268), the boronic acid derivatives (for example according to WO 2006/117052) or the benzanthracenes (for example according to WO 2008/145239). Particularly preferred host materials are selected from the classes of the oligoarylenes comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes comprising anthracene, benzanthracene, benzophenanthrene and/or pyrene or atropisomers of these compounds.

An oligoarylene in the context of this invention shall be understood to mean a compound in which at least three aryl or arylene groups are bonded to one another.

Various substance classes are useful as further matrix materials, preferably for phosphorescent emitters, as well as the composition of the invention as described above, more preferably comprising a mixture of materials selected from M1 to M72. Preferred further matrix materials are selected from the classes of the aromatic amines, especially triarylamines, for example according to US 2005/0069729, carbazole derivatives (e.g. CBP, N,N-biscarbazolylbiphenyl) or compounds according to WO 2005/039246, US 2005/0069729, JP 2004/288381, EP 1205527 or WO 2008/086851, bridged carbazole derivatives, for example according to WO 2011/088877 and WO 2011/128017, indenocarbazole derivatives, for example according to WO 2010/136109 and WO 2011/000455, azacarbazole derivatives, for example according to EP 1617710, EP 1617711, EP 1731584, JP 2005/347160, indolocarbazole derivatives, for example according to WO 2007/063754 or WO 2008/056746, ketones, for example according to WO 2004/093207 or WO 2010/006680, phosphine oxides, sulfoxides and sulfones, for example according to WO 2005/003253, oligophenylenes, bipolar matrix materials, for example according to WO 2007/137725, silanes, for example according to WO 2005/111172, azaboroles or boronic esters, for example according to WO 2006/117052, triazine derivatives, for example according to WO 2010/015306, WO 2007/063754 or WO 2008/056746, zinc complexes, for example according to EP 652273 or WO 2009/062578, aluminum complexes, e.g. BAlq, diazasilole derivatives and tetraazasilole derivatives, for example according to WO 2010/054729, diazaphosphole derivatives, for example according to WO 2010/054730, and aluminum complexes, e.g. BAlQ.

In an alternative embodiment of the present invention, the composition, aside from the bipolar host and uncharged co-host constituents and optionally a phosphorescent emitter, does not contain any further constituents, i.e. any functional materials.

The invention accordingly further provides a composition consisting of a compound of the formula (1), (1a) to (1j) or a compound selected from 1 to 8 and a compound of the formula (2), (2a), (2b), (2c) or a compound selected from 9 to 17.

The invention accordingly further provides a composition consisting of a phosphorescent emitter, a compound of the formula (1), (1a) to (1j) or a compound selected from 1 to 8 and a compound of the formula (2), (2a), (2b), (2c) or a compound selected from 9 to 17.

The composition of the invention as described above or described as preferred is suitable for use in an organic electronic device. An organic electronic device is understood here to mean a device containing at least one layer containing at least one organic compound. The device may also comprise inorganic materials or else layers formed entirely from inorganic materials.

The invention accordingly further provides for the use of a composition as described above or described as preferred, especially of a mixture selected from M1 to M72, in an organic electronic device.

The components or constituents of the compositions may be processed by vapour deposition or from solution. If the compositions are applied from solution, formulations of the composition of the invention comprising at least one further solvent are required. These formulations may, for example, be solutions, dispersions or emulsions. For this purpose, it may be preferable to use mixtures of two or more solvents.

The present invention therefore further provides a formulation comprising a composition of the invention and at least one solvent.

Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (-)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane, hexamethylindane or mixtures of these solvents.

The formulation may also comprise at least one further organic or inorganic compound which is likewise used in the electronic device, especially an emitting compound, especially a phosphorescent emitter and/or a further matrix material. Suitable emitting compounds and further matrix materials have already been detailed above.

The present invention also provides for the use of the composition of the invention in an organic electronic device, preferably in an electron-transporting layer and/or in an emitting layer.

The organic electronic device is preferably selected from organic integrated circuits (OICs), organic field-effect transistors (OFETs), organic thin-film transistors (OTFTs), organic electroluminescent devices, organic solar cells (OSCs), organic optical detectors and organic photoreceptors, particular preference being given to organic electroluminescent devices.

Very particularly preferred organic electroluminescent devices for the use of the composition of the invention are organic light-emitting transistors (OLETs), organic field-quench devices (OFQDs), organic light-emitting electrochemical cells (OLECs, LECs, LEECs), organic laser diodes (0-lasers) and organic light-emitting diodes (OLEDs); OLECs and OLEDs are especially preferred and OLEDs are most preferred.

Preferably, the composition of the invention as described above or described as preferred is used in a layer having an electron-transporting function in an electronic device. The layer is preferably an electron injection layer (EIL), an electron transport layer (ETL), a hole blocker layer (HBL) and/or an emission layer (EML), more preferably an ETL, EIL and/or an EML. Most preferably, the composition of the invention is used in an EML, especially as matrix material.

Therefore, the present invention further provides an organic electronic device which is especially selected from one of the aforementioned electronic devices and which comprises the composition of the invention, as described above or described as preferred, preferably in an emission layer (EML), in an electron transport layer (ETL), in an electron injection layer (EIL) and/or in a hole blocker layer (HBL), very preferably in an EML, EIL and/or ETL and most preferably in an EML.

When the layer is an emitting layer, it is especially preferably a phosphorescent layer which is characterized in that it comprises, in addition to the composition as described above or described as preferred, a phosphorescent emitter, especially together with an emitter from Table 4 or 5 or a preferred emitter as described above.

In a particularly preferred embodiment of the present invention, therefore, the electronic device is an organic electroluminescent device, most preferably an organic light-emitting diode (OLED), comprising the composition of the invention as described above or described as preferred together with a phosphorescent emitter, preferably an emitter from Table 4 or 5, more preferably with a green emitter, in the emission layer (EML).

The composition of the invention in the preferred embodiments, comprising at least one emitting compound, contains preferably between 99.9% and 1% by volume, further preferably between 99% and 10% by volume, especially preferably between 98% and 60% by volume, very especially preferably between 97% and 80% by volume, of matrix material composed of at least one compound of the formula (1) and at least one compound of the formula (2) according to the preferred embodiments, based on the overall mixture of emitter and matrix material. Correspondingly, the composition preferably contains between 0.1% and 99% by volume, further preferably between 1% and 90% by volume, more preferably between 2% and 40% by volume, most preferably between 3% and 20% by volume, of the emitter based on the overall composition of emitter and matrix material. If the compounds are processed from solution, preference is given to using the corresponding amounts in % by weight rather than the above-specified amounts in % by volume.

Apart from the cathode, anode and the layer comprising the composition of the invention, an electronic device may comprise further layers. These are selected, for example, from in each case one or more hole injection layers, hole transport layers, hole blocker layers, emitting layers, electron transport layers, electron injection layers, electron blocker layers, exciton blocker layers, interlayers, charge generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*) and/or organic or inorganic p/n junctions. However, it should be pointed out that not necessarily every one of these layers need be present.

The sequence of layers in an organic electroluminescent device is preferably as follows:

anode/hole injection layer/hole transport layer/emitting layer/electron transport layer/electron injection layer/cathode.

The sequence of the layers is a preferred sequence.

At the same time, it should be pointed out again that not all the layers mentioned need be present and/or that further layers may additionally be present.

An organic electroluminescent device comprising the composition of the invention may comprise multiple emitting layers. More preferably, these emission layers in this case have several emission maxima between 380 nm and 750 nm overall, such that the overall result is white emission; in other words, various emitting compounds which may fluoresce or phosphoresce and which emit blue or yellow or orange or red light are used in the emitting layers. Especially preferred are three-layer systems, i.e. systems having three emitting layers, where the three layers show blue, green and orange or red emission (for the basic construction see, for example, WO 2005/011013). It should be noted that, for the production of white light, rather than a plurality of color-emitting emitter compounds, an emitter compound used individually which emits over a broad wavelength range may also be suitable.

Suitable charge transport materials as usable in the hole injection or hole transport layer or electron blocker layer or in the electron transport layer of the organic electroluminescent device of the invention are, for example, the compounds disclosed in Y. Shirota et al., Chem. Rev. 2007, 107(4), 953-1010, or other materials as used in these layers according to the prior art. Materials used for the electron transport layer may be any materials as used according to the prior art as electron transport materials in the electron transport layer. Especially suitable are aluminium complexes, for example $Alq_3$, zirconium complexes, for example $Zrq_4$, benzimidazole derivatives, triazine derivatives, pyrimidine derivatives, pyridine derivatives, pyrazine derivatives, quinoxaline derivatives, quinoline derivatives, oxadiazole derivatives, aromatic ketones, lactams, boranes, diazaphosphole derivatives and phosphine oxide derivatives. Further suitable materials are derivatives of the above-mentioned compounds as disclosed in JP 2000/053957, WO 2003/060956, WO 2004/028217, WO 2004/080975 and WO 2010/072300.

Preferred hole transport materials are especially materials which can be used in a hole transport, hole injection or electron blocker layer, such as indenofluoreneamine derivatives (for example according to WO 06/122630 or WO 06/100896), the amine derivatives disclosed in EP 1661888, hexaazatriphenylene derivatives (for example according to WO 01/049806), amine derivatives having fused aromatic systems (for example according to U.S. Pat. No. 5,061,569), the amine derivatives disclosed in WO 95/09147, monobenzoindenofluoreneamines (for example according to WO 08/006449), dibenzoindenofluoreneamines (for example according to WO 07/140847), spirobifluoreneamines (for example according to WO 2012/034627 or the as yet unpublished EP 12000929.5), fluoreneamines (for example according to WO 2014/015937, WO 2014/015938 and WO 2014/015935), spirodibenzopyranamines (for example according to WO 2013/083216) and dihydroacridine derivatives (for example WO 2012/150001).

Preferred cathodes of electronic devices are metals having a low work function, metal alloys or multilayer structures composed of various metals, for example alkaline earth metals, alkali metals, main group metals or lanthanoids (e.g. Ca, Ba, Mg, Al, In, Mg, Yb, Sm, etc.). Additionally suitable are alloys composed of an alkali metal or alkaline earth metal and silver, for example an alloy composed of magnesium and silver. In the case of multilayer structures, in addition to the metals mentioned, it is also possible to use further metals having a relatively high work function, for example Ag or Al, in which case combinations of the metals such as Ca/Ag, Mg/Ag or Ba/Ag, for example, are generally used. It may also be preferable to introduce a thin interlayer of a material having a high dielectric constant between a metallic cathode and the organic semiconductor. Examples of useful materials for this purpose are alkali metal or alkaline earth metal fluorides, but also the corresponding oxides or carbonates (e.g. LiF, $Li_2O$, $BaF_2$, MgO, NaF, CsF, $Cs_2CO_3$, etc.). It is also possible to use lithium quinolinate (LiQ) for this purpose. The layer thickness of this layer is preferably between 0.5 and 5 nm.

Preferred anodes are materials having a high work function. Preferably, the anode has a work function of greater than 4.5 eV versus vacuum. Firstly, metals having a high redox potential are suitable for this purpose, for example Ag, Pt or Au. Secondly, metal/metal oxide electrodes (e.g. Al/Ni/$NiO_x$, Al/$PtO_x$) may also be preferred. For some applications, at least one of the electrodes has to be transparent or partly transparent in order to enable the irradiation of the organic material (organic solar cell) or the emission of light (OLED, O-LASER). Preferred anode materials here are conductive mixed metal oxides. Particular preference is given to indium tin oxide (ITO) or indium zinc oxide (IZO). Preference is further given to conductive doped organic materials, especially conductive doped polymers. In addition, the anode may also consist of two or more layers, for example of an inner layer of ITO and an outer layer of a metal oxide, preferably tungsten oxide, molybdenum oxide or vanadium oxide.

The organic electronic device, in the course of production, is appropriately (according to the application) structured, contact-connected and finally sealed, since the lifetime of the devices of the invention is shortened in the presence of water and/or air.

In a further preferred embodiment, the organic electronic device comprising the composition of the invention is characterized in that one or more organic layers comprising the composition of the invention are applied by a sublimation method. In this case, the materials are applied by vapour deposition in vacuum sublimation systems at an initial pressure of less than $10^{-5}$ mbar, preferably less than $10^{-6}$ mbar. In this case, however, it is also possible that the initial pressure is even lower, for example less than $10^{-7}$ mbar.

Preference is likewise given to an organic electroluminescent device, characterized in that one or more layers are applied by the OVPD (organic vapour phase deposition) method or with the aid of a carrier gas sublimation. In this case, the materials are applied at a pressure between $10^{-5}$ mbar and 1 bar. A special case of this method is the OVJP (organic vapour jet printing) method, in which the materials are applied directly by a nozzle and thus structured (for example, M. S. Arnold et al., Appl. Phys. Lett. 2008, 92, 053301).

Preference is additionally given to an organic electroluminescent device, characterized in that one or more organic layers comprising the composition of the invention are produced from solution, for example by spin-coating, or by any printing method, for example screen printing, flexographic printing, nozzle printing or offset printing, but more preferably LITI (light-induced thermal imaging, thermal transfer printing) or inkjet printing. For this purpose, soluble compounds of the components of the composition of the invention are needed. High solubility can be achieved by suitable substitution of the corresponding compounds. Processing from solution has the advantage that the layer comprising the composition of the invention can be applied in a very simple and inexpensive manner. This technique is especially suitable for the mass production of organic electronic devices.

In addition, hybrid methods are possible, in which, for example, one or more layers are applied from solution and one or more further layers are applied by vapour deposition.

These methods are known in general terms to those skilled in the art and can be applied to organic electroluminescent devices.

The invention therefore further provides a process for producing an organic electronic device comprising a composition of the invention as described above or described as preferred, characterized in that at least one organic layer comprising a composition of the invention is applied by gas phase deposition, especially by a sublimation method and/or by an OVPD (organic vapour phase deposition) method and/or with the aid of carrier gas sublimation, or from solution, especially by spin-coating or by a printing method.

In the production of an organic electronic device by means of gas phase deposition, there are two methods in principle by which an organic layer which is to comprise the composition of the invention and which may comprise multiple different constituents can be applied, or applied by vapour deposition, to any substrate. Firstly, the materials used can each be initially charged in a material source and ultimately evaporated from the different material sources ("co-evaporation"). Secondly, the various materials can be premixed and the mixture can be initially charged in a single material source from which it is ultimately evaporated ("premix evaporation"). In this way, it is possible in a simple and rapid manner to achieve the vapour deposition of a layer with homogeneous distribution of the components without a need for precise actuation of a multitude of material sources.

The invention accordingly further provides a process characterized in that the at least one compound of the formula (1) as described above or described as preferred and the at least one compound of the formula (2) as described above or described as preferred are deposited from the gas phase successively or simultaneously from at least two material sources, optionally with other materials as described above or described as preferred, and form the organic layer.

In a preferred embodiment of the present invention, the at least one organic layer is applied by means of gas phase deposition, wherein the constituents of the composition are premixed and evaporated from a single material source.

The invention accordingly further provides a process characterized in that the composition of the invention as described above or described as preferred is utilized as material source for the gas phase deposition and, optionally together with further materials, forms the organic layer.

The invention further provides a process for producing an organic electronic device comprising a composition of the invention as described above or described as preferred, characterized in that the formulation of the invention as described above is used to apply the organic layer.

The compositions of the invention and the devices of the invention feature the following surprising advantages over the prior art:

The use of the compositions of the invention in organic electronic devices, especially in an organic electroluminescent device, and especially in an OLED or OLEC, leads to distinct increases in the lifetime of the devices.

As apparent in Example 1 cited below, the use of host materials of the formula (1) alone, for example of the compound utilized in the OLED C1, achieves good voltages and efficiencies at moderate emitter concentrations in the EML of 12%. However, the lifetime of the components is short.

An improvement in the lifetime together with an improved component efficiency can be achieved by means of the inventive combination of the compounds of the formula (1) as described above with compounds of the formula (2) as described above.

This improvement in the lifetime and improved component efficiency can preferably be achieved by virtue of the inventive combination of the compounds of the formula (1) as described above with compounds of the formula (2) as described above at emitter concentrations of 2% to 15% by weight in the emission layer.

This advantage is shown illustratively and representatively for compounds of the formula (1) through use of the compound 1 (abbreviated to CbzT2) with the triphenylene derivative 9 (abbreviated to WBG1) in Examples I2 and I4 at an emitter concentration of 12%.

Even with a small emitter concentration of only 7% in the EML, at which the lifetime of an OLED typically falls, the lifetimes achieved for the inventive combinations are even more distinctly improved over the prior art. This is shown illustratively and representatively for compounds of the formula (1) through use of the compound 1 (abbreviated to CbzT2) with the triphenylene derivative 9 (abbreviated to WBG1) in Examples I1 and I3 at an emitter concentration of 7%.

The difference from the disclosure of WO 2015/192941 with the data 121 lies in the structure of the bipolar host of the formula (1). The combination with a yellow emitter shows a high lifetime. The person skilled in the art is aware that the lifetime of an electroluminescent device comprising a yellow emitter is generally higher than one comprising a green emitter. In an unforeseeable manner to the person skilled in the art, the change in structure to compounds of the formula (1) as described above or described as preferred, especially to the compounds 1 to 8, leads to an improvement in the lifetime of electronic devices, especially of OLEDs, even those containing a green emitter. This improvement becomes clear since the lifetime and component efficiency is increased compared to the prior art.

The compositions of the invention are of very good suitability for use in an emission layer and exhibit improved performance data, especially in respect of lifetime, over compounds from the prior art as described above.

The compositions of the invention can easily be processed and are therefore of very good suitability for mass production in commercial use.

The compositions of the invention can be premixed and vapour-deposited from a single material source, and so it is possible in a simple and rapid manner to produce an organic layer with homogeneous distribution of the components used.

It should be pointed out that variations of the embodiments described in the present invention are covered by the scope of this invention. Any feature disclosed in the present invention may, unless this is explicitly ruled out, be exchanged for alternative features which serve the same purpose or an equivalent or similar purpose. Any feature disclosed in the present invention, unless stated otherwise, should therefore be considered as an example from a generic series or as an equivalent or similar feature.

All features of the present invention may be combined with one another in any manner, unless particular features and/or steps are mutually exclusive. This is especially true of preferred features of the present invention. Equally, features of non-essential combinations may be used separately (and not in combination).

The technical teaching disclosed with the present invention may be abstracted and combined with other examples.

The invention is illustrated in more detail by the examples which follow, without any intention of restricting it thereby.

General Methods:

Determination of Orbital Energies and Electronic States

The HOMO and LUMO energies and the triplet level and the singlet levels of the materials are determined via quantum-chemical calculations. For this purpose, in the present case, the "Gaussian09, Revision D.01" software package (Gaussian Inc.) is used. For calculation of organic substances without metals (referred to as the "org." method), a geometry optimization is first conducted by the semi-empirical method AM1 (Gaussian input line "#AM1 opt") with charge 0 and multiplicity 1. Subsequently, on the basis of the optimized geometry, a (single-point) energy calculation is effected for the electronic ground state and the triplet level. This is done using the TDDFT (time dependent density functional theory) method B3PW91 with the 6-31G(d) basis set (Gaussian input line "#B3PW91/6-31G(d) td=(50-50, nstates=4)") (charge 0, multiplicity 1). For organometallic compounds (referred to as the "M-org." method), the geometry is optimized by the Hartree-Fock method and the LanL2 MB basis set (Gaussian input line "#HF/LanL2 MB opt") (charge 0, multiplicity 1). The energy calculation is effected, as described above, analogously to that for the organic substances, except that the "LanL2DZ" basis set is used for the metal atom and the "6-31G(d)" basis set for the ligands (Gaussian input line "#B3PW91/gen pseudo=lanl2 td=(50-50,nstates=4)"). From the energy calculation, the HOMO is obtained as the last orbital occupied by two electrons (alpha occ. eigenvalues) and LUMO as the first unoccupied orbital (alpha virt. eigenvalues) in Hartree units, where HEh and LEh represent the HOMO energy in Hartree units and the LUMO energy in Hartree units respectively. This is used to determine the HOMO and LUMO value in electron volts, calibrated by cyclic voltammetry measurements, as follows:

HOMO(eV)=(HEh*27.212)*0.8308−1.118;

LUMO(eV)=(LEh*27.212)*1.0658−0.5049.

The triplet level $T_1$ of a material is defined as the relative excitation energy (in eV) of the triplet state having the lowest energy which is found by the quantum-chemical energy calculation.

The singlet level S1 of a material is defined as the relative excitation energy (in eV) of the singlet state having the second-lowest energy which is found by the quantum-chemical energy calculation.

The energetically lowest singlet state is referred to as S0.

The method described herein is independent of the software package used and always gives the same results. Examples of frequently utilized programs for this purpose are "Gaussian09" (Gaussian Inc.) and Q-Chem 4.1 (Q-Chem, Inc.). In the present case, the energies are calculated using the software package "Gaussian09, Revision D.01".

EXAMPLE 1: PRODUCTION OF THE OLEDS

Examples I1 to I4 which follow (see Table 6) present the use of the material combinations of the invention in OLEDs.

Pretreatment for Examples I1-I4: Glass plaques coated with structured ITO (indium tin oxide) of thickness 50 nm are treated prior to coating, first with an oxygen plasma, followed by an argon plasma. These plasma-treated glass plaques form the substrates to which the OLEDs are applied. The OLEDs basically have the following layer structure: substrate/hole injection layer (HIL)/hole transport layer (HTL)/electron blocker layer (EBL)/emission layer (EML)/optional hole blocker layer (HBL)/electron transport layer (ETL)/optional electron injection layer (EIL) and finally a cathode. The cathode is formed by an aluminium layer of thickness 100 nm. The exact structure of the OLEDs can be found in Table 6. The materials required for production of the OLEDs are shown in Table 7. The data of the OLEDs are listed in Table 8. Example C1 is a comparative example containing, in a representative manner, only a host material of the formula (1); Examples I1 to I4 show data for OLEDs of the invention.

All materials are applied by thermal vapour deposition in a vacuum chamber. In this case, the emission layer always consists of at least one matrix material (host material), for the purposes of the invention the at least two matrix materials, and an emitting dopant (emitter) which is added to the matrix materials in a particular proportion by volume by co-evaporation. Details given in such a form as CbzT2:WBG1:TEG1 (46%:47%:7%) mean here that the material CbzT2 is present in the layer in a proportion by volume of 46%, WBG1 in a proportion of 47% and TEG1 in a proportion of 7%. Analogously, the electron transport layer may also consist of a mixture of two materials.

The OLEDs are characterized in a standard manner. For this purpose, the electroluminescence spectra, the current efficiency (CE, measured in cd/A) and the external quantum efficiency (EQE, measured in %) are determined as a function of luminance, calculated from current-voltage-luminance characteristics assuming Lambertian emission characteristics, as is the lifetime. The electroluminescence spectra are determined at a luminance of 1000 cd/m$^2$, and the CIE 1931 x and y colour coordinates are calculated therefrom. The parameter U1000 in Table 8 refers to the voltage which is required for a luminance of 1000 cd/m$^2$. CE1000 and EQE1000 respectively denote the current efficiency and external quantum efficiency that are attained at 1000 cd/m$^2$.

The lifetime LT is defined as the time after which the luminance drops from the starting luminance to a certain proportion L1 in the course of operation with constant current density $j_0$. A figure of L1=80% in Table 8 means that the lifetime reported in the LT column corresponds to the time after which the luminance falls to 80% of its starting value.

Use of Mixtures of the Invention in OLEDs

The material combinations of the invention can be used in the emission layer in phosphorescent OLEDs. The inventive combination of the compound CbzT2, corresponding to compound 1, with WBG1 (corresponding to compound 9) is used in Examples I1 to I4 as matrix material in the emission layer.

TABLE 6

Structure of the OLEDs

| Ex. | HIL thickness | HTL thickness | EBL thickness | EML thickness | HBL thickness | ETL thickness | EIL thickness |
|---|---|---|---|---|---|---|---|
| C1 | HATCN 5 nm | SpMA1 215 nm | SpMA2 20 nm | CbzT2:TEG1 (88%:12%) 30 nm | ST2 10 nm | ST2:LiQ (50%:50%) 30 nm | LiQ 1 nm |
| I1 | HATCN 5 nm | SpMA1 215 nm | SpMA2 20 nm | CbzT2:WBG1:TEG1 (46%:47%:7%) 30 nm | ST2 10 nm | ST2:LiQ (50%:50%) 30 nm | LiQ 1 nm |
| I2 | HATCN 5 nm | SpMA1 215 nm | SpMA2 20 nm | CbzT2:WBG1:TEG1 (22%:66%:12%) 30 nm | ST2 10 nm | ST2:LiQ (50%:50%) 30 nm | LiQ 1 nm |
| I3 | HATCN 5 nm | SpMA1 215 nm | SpMA2 20 nm | CbzT2:WBG1:TEG2 (46%:47%:7%) 30 nm | ST2 10 nm | ST2:LiQ (50%:50%) 30 nm | LiQ 1 nm |
| I4 | HATCN 5 nm | SpMA1 215 nm | SpMA2 20 nm | CbzT2:WBG1:TEG2 (22%:66%:12%) 30 nm | ST2 10 nm | ST2:LiQ (50%:50%) 30 nm | LiQ 1 nm |

TABLE 7

Structural formulae of the materials for OLEDs

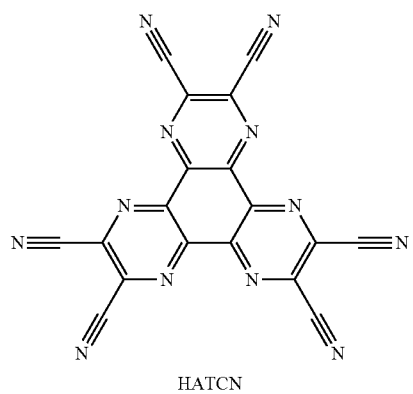

HATCN

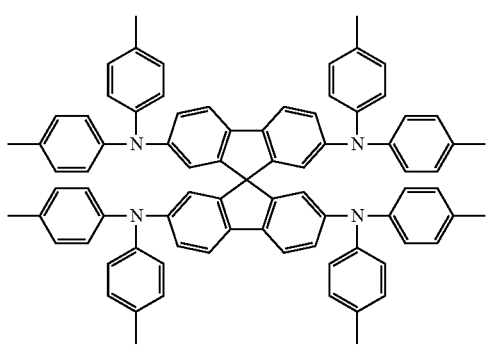

SpA1

TABLE 7-continued

Structural formulae of the materials for OLEDs

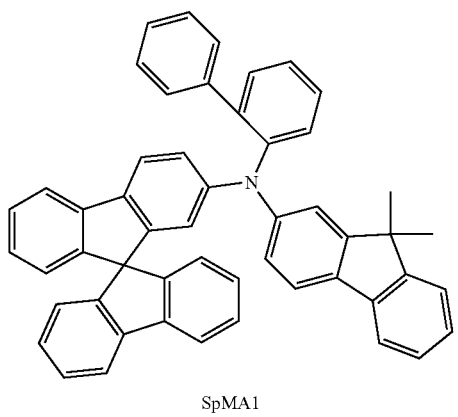 [SMILES: CC1(C)c2ccccc2-c2ccc(N(c3ccc4c(c3)C3(c5ccccc5-c5ccccc53)c3ccccc3-4)c3ccccc3-c3ccccc3)cc21]

SpMA1

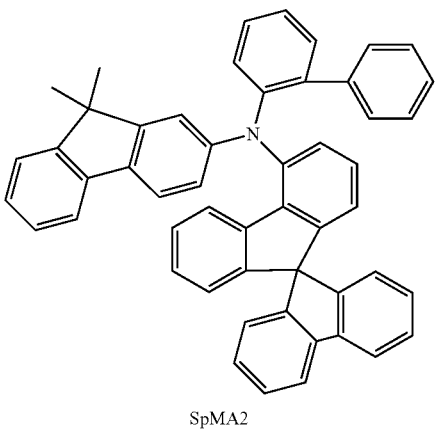 [SMILES: CC1(C)c2ccccc2-c2ccc(N(c3ccccc3-c3ccccc3)c3cccc4c3-c3ccccc3C43c4ccccc4-c4ccccc43)cc21]

SpMA2

TABLE 7-continued
Structural formulae of the materials for OLEDs
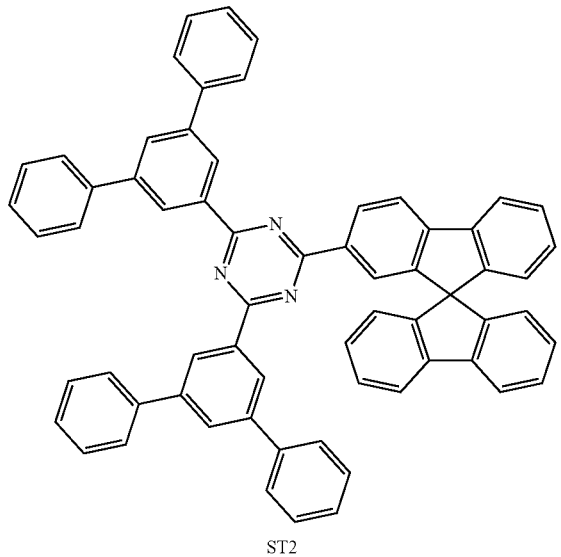
ST2
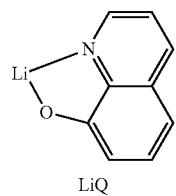
LiQ
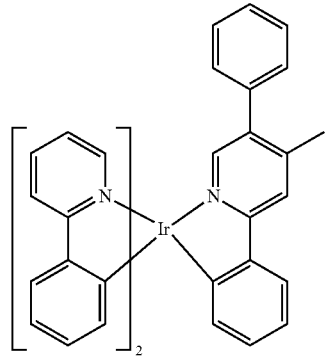
TEG1
TABLE 7-continued
Structural formulae of the materials for OLEDs
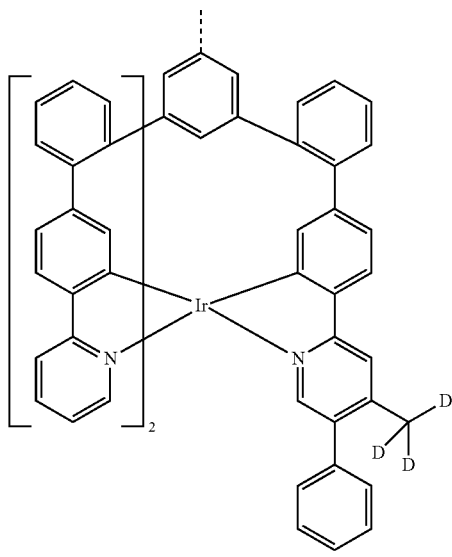
TEG2
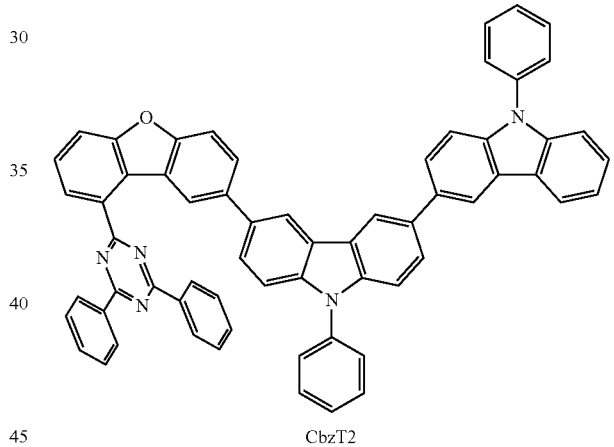
CbzT2
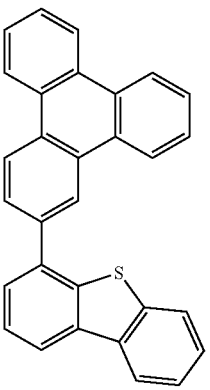
WBG1

TABLE 8

Data of the OLEDs

| Ex. | U1000 (V) | CE1000 (cd/A) | EQE 1000 (%) | CIE x/y at 1000 cd/m² | $j_0$ (mA/cm²) | L1 (%) | LT (h) |
|---|---|---|---|---|---|---|---|
| C1 | 3.0 | 60 | 16.4 | 0.33/0.63 | 20 | 80 | 660 |
| I1 | 3.3 | 76 | 20.6 | 0.32/0.64 | 20 | 80 | 819 |
| I2 | 3.7 | 64 | 17.4 | 0.32/0.64 | 20 | 80 | 1262 |
| I3 | 3.4 | 77 | 20.5 | 0.39/0.59 | 20 | 80 | 1576 |
| I4 | 3.8 | 76 | 19.9 | 0.38/0.60 | 20 | 80 | 3017 |

An excellent improvement in lifetime and efficiency at high and in particular low emitter concentrations (12% or 7%) in the EML is obtained through the specific combination with the emitter TEG1. In combination with the emitter TEG2 (I3 and I4), another distinct improvement in the lifetimes is possible.

The mixtures of the invention which follow show similar behaviour in the electronic device:

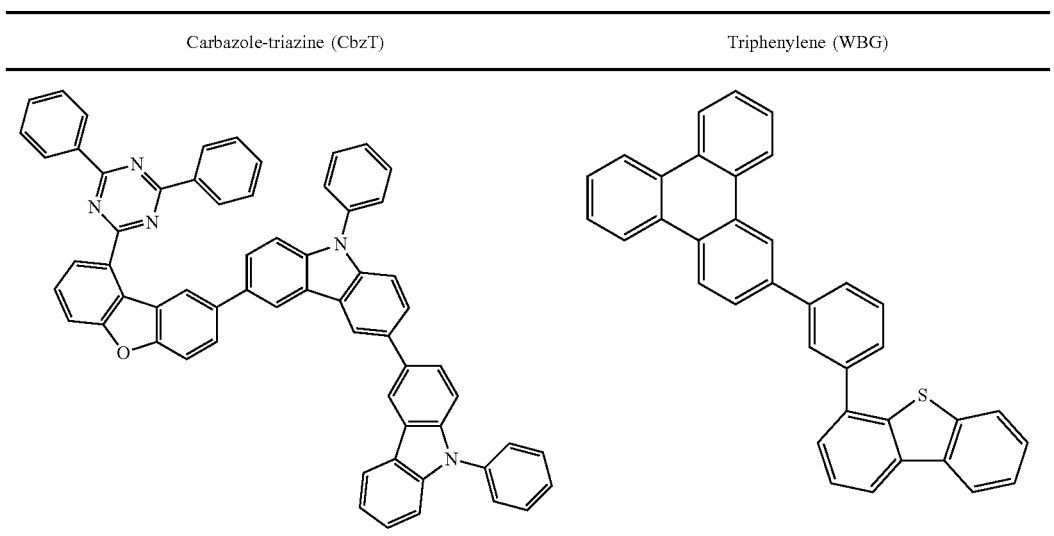

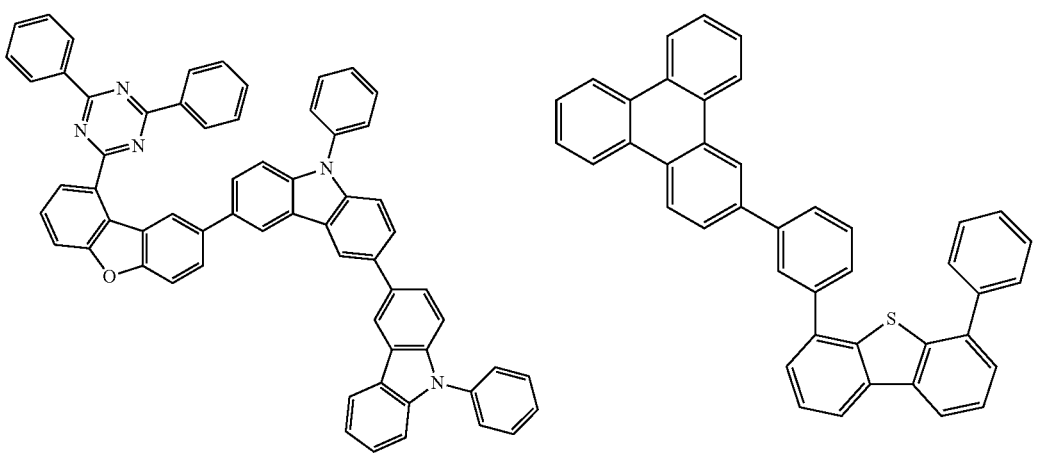

| Carbazole-triazine (CbzT) | Triphenylene (WBG) |
|---|---|
| 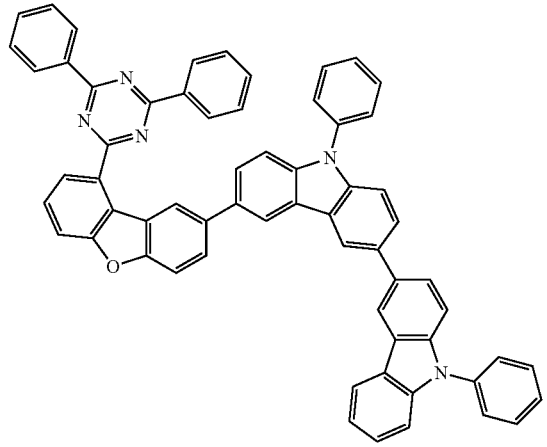<br>1 | 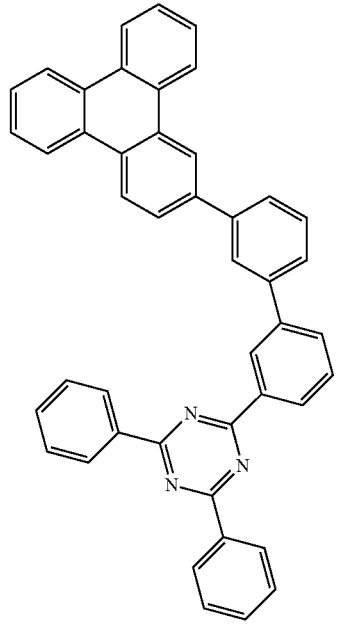 [SMILES: c1ccc(-c2nc(-c3ccccc3)nc(-c3cccc(-c4cccc(-c5ccc6c7ccccc7c7ccccc7c6c5)c4)c3)n2)cc1] |
| 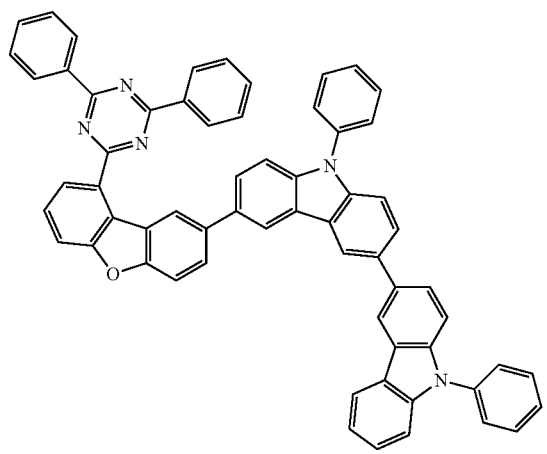<br>1 | 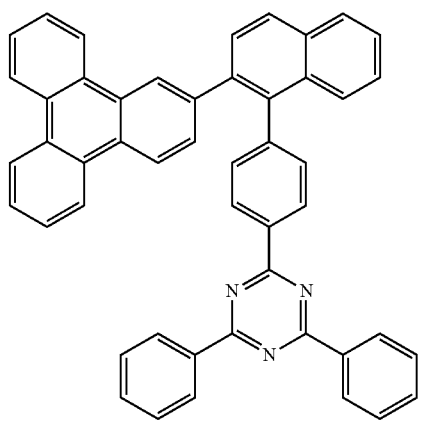 [SMILES: c1ccc(-c2nc(-c3ccccc3)nc(-c3ccc(-c4c(-c5ccc6c7ccccc7c7ccccc7c6c5)ccc5ccccc45)cc3)n2)cc1] |
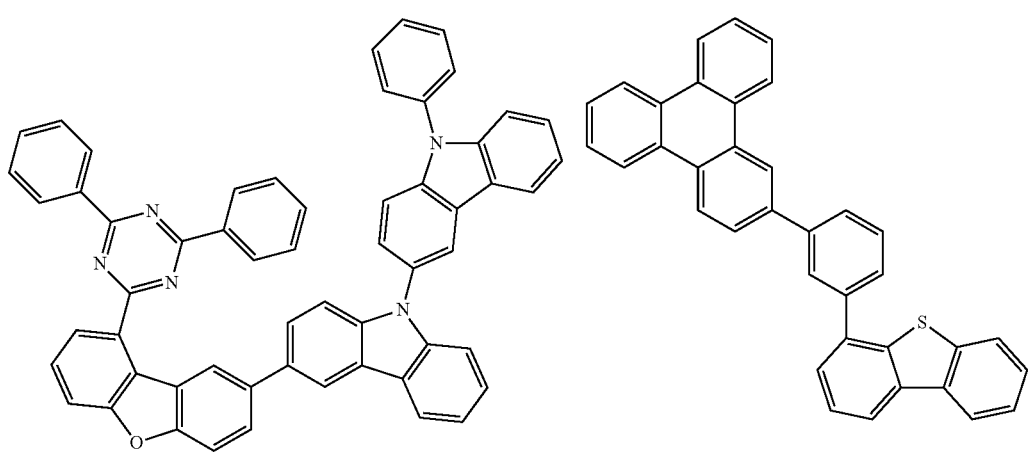
8

-continued
| Carbazole-triazine (CbzT) | Triphenylene (WBG) |
|---|---|
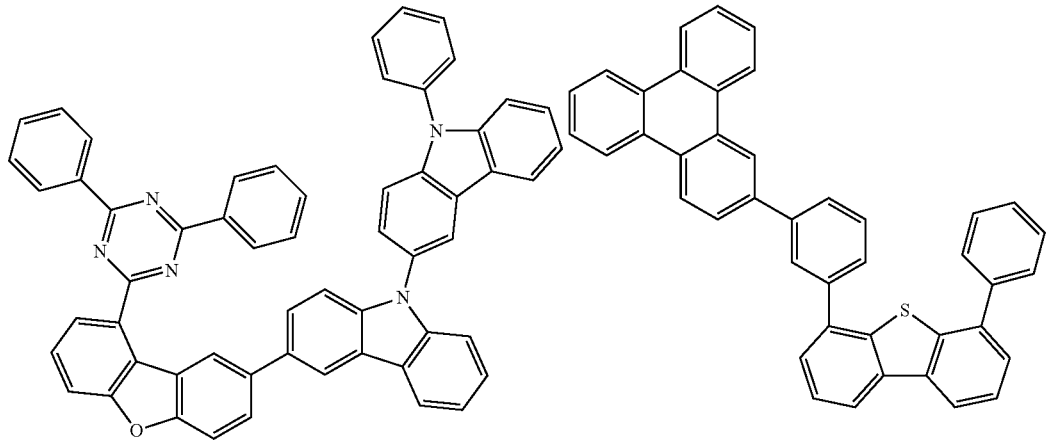
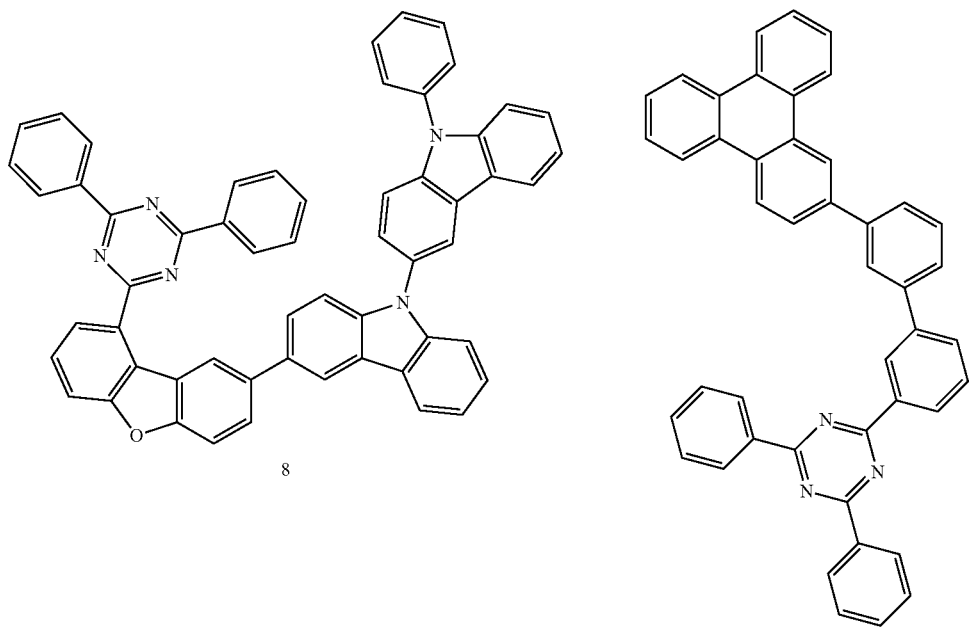
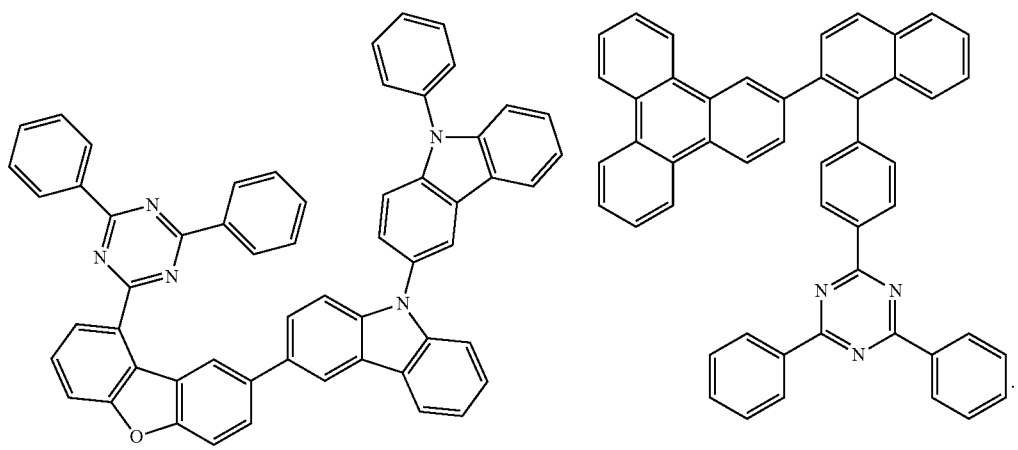

EXAMPLE 2: SYNTHESIS OF COMPOUND 1 (CBZT2)

a) 6-Bromo-2-fluoro-2'-methoxybiphenyl

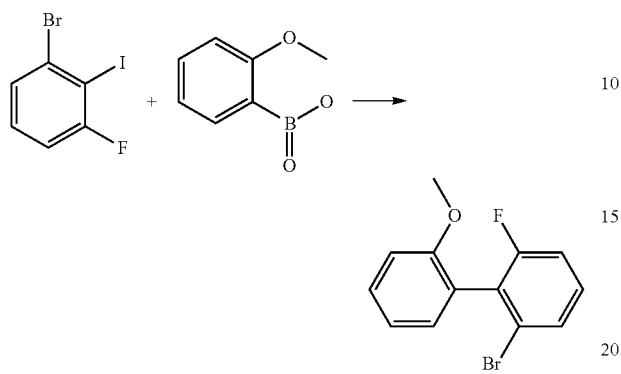

200 g (664 mmol) of 1-bromo-3-fluoro-2-iodobenzene, 101 g (664 mmol) of 2-methoxyphenylboronic acid and 137.5 g (997 mmol) of sodium tetraborate are dissolved in 1000 ml of THF and 600 ml of water, and degassed. 9.3 g (13.3 mmol) of bis(triphenylphosphine)palladium(II) chloride and 1 g (20 mmol) of hydrazinium hydroxide are added. The reaction mixture is then stirred under a protective gas atmosphere at 70° C. for 48 h. The cooled solution is supplemented with toluene, washed repeatedly with water, dried and concentrated. The product is purified via column chromatography on silica gel with toluene/heptane (1:2). Yield: 155 g (553 mmol), 83% of theory.

b) 6'-Bromo-2'-fluorobiphenyl-2-ol

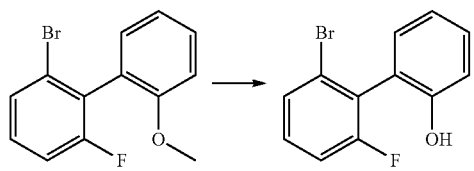 [SMILES: COc1ccccc1-c1c(F)cccc1Br ; Oc1ccccc1-c1c(F)cccc1Br]

112 g (418 mmol) of 6-bromo-2-fluoro-2'-methoxybiphenyl are dissolved in 2 l of dichloromethane and cooled to 5° C. 41.01 ml (431 mmol) of boron tribromide are added dropwise to this solution within 90 min, and stirring of the mixture continues overnight. The mixture is subsequently admixed gradually with water, and the organic phase is washed three times with water, dried over $Na_2SO_4$, concentrated by rotary evaporation and purified by chromatography. Yield: 104 g (397 mmol), 98% of theory.

c) 1-Bromodibenzofuran

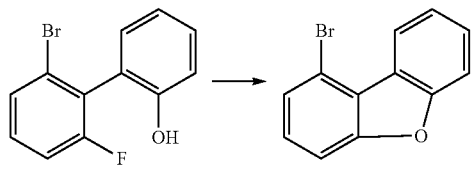 [SMILES: Oc1ccccc1-c1c(F)cccc1Br ; Brc1cccc2oc3ccccc3c12]

111 g (416 mmol) of 6'-bromo-2'-fluorobiphenyl-2-ol are dissolved in 2 l of DMF (max. 0.003% $H_2O$) SeccoSolv® and cooled to 5° C. 20 g (449 mmol) of sodium hydride (60% suspension in paraffin oil) are added to this solution in portions, once the addition has ended the mixture is stirred for 20 min, and then the mixture is heated to 100° C. for 45 min. After cooling, 500 ml of ethanol are added gradually to the mixture, which is concentrated by rotary evaporation and then purified by chromatography. Yield: 90 g (367 mmol), 88.5% of theory.

d) Dibenzofuran-1-boronic Acid

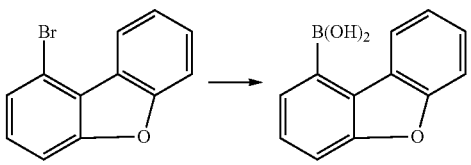 [SMILES: Brc1cccc2oc3ccccc3c12 ; OB(O)c1cccc2oc3ccccc3c12]

180 g (728 mmol) of 1-bromodibenzofuran are dissolved in 1500 ml of dry THF and cooled to −78° C. At this temperature, 305 ml (764 mmol/2.5 M in hexane) of n-butyllithium are added within about 5 min, and then the mixture is stirred at −78° C. for a further 2.5 h. At this temperature, 151 g (1456 mmol) of trimethyl borate are added very rapidly and the reaction is allowed to come gradually to room temperature (about 18 h). The reaction solution is washed with water and the precipitated solids and the organic phase are subjected to azeotropic drying with toluene. The crude product is extracted while stirring from toluene/methylene chloride at about 40° C. and filtered off with suction. Yield: 146 g (690 mmol), 95% of theory.

e) 2-Dibenzofuran-1-yl-4,6-diphenyl[1,3,5]triazine

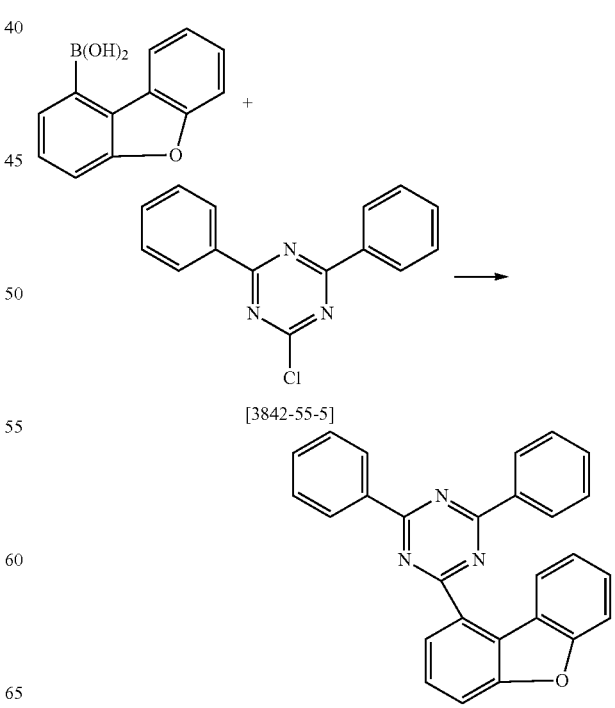

[3842-55-5]

23 g (110.0 mmol) of dibenzofuran-1-boronic acid, 29.5 g (110.0 mmol) of 2-chloro-4,6-diphenyl-1,3,5-triazine and 21 g (210.0 mmol) of sodium carbonate are suspended in 500 ml of ethylene glycol diamine ether and 500 ml of water. Added to this suspension are 913 mg (3.0 mmol) of tri-o-tolylphosphine and then 112 mg (0.5 mmol) of palladium(II) acetate, and the reaction mixture is heated under reflux for 16 h. After cooling, the organic phase is removed, filtered through silica gel, washed three times with 200 ml of water and then concentrated to dryness. The residue is recrystallized from toluene and from dichloromethane/heptane. The yield is 37 g (94 mmol), corresponding to 87% of theory.

f) 2-(8-Bromodibenzofuran-1-yl)-4,6-diphenyl[1,3,5]triazine

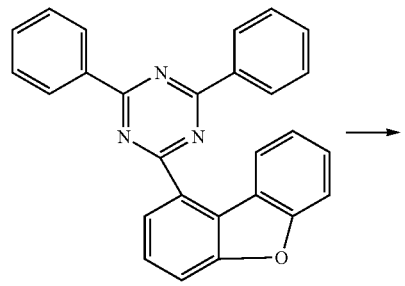

70 g (190.0 mmol) of 2-dibenzofuran-1-yl-4,6-diphenyl[1,3,5]triazine are suspended in 2000 ml of acetic acid (100%) and 2000 ml of sulfuric acid (95-98%). 34 g (190 mmol) of NBS are added to this suspension in portions and the mixture is stirred in the dark for 2 h. Thereafter, water/ice is added and solids are removed and washed with ethanol. The residue is recrystallized from toluene. The yield is 80 g (167 mmol), corresponding to 87% of theory.

g) 3-[9-(4,6-Diphenyl[1,3,5]triazin-2-yl)dibenzofuran-2-yl]-9-phenyl-9H-carbazole

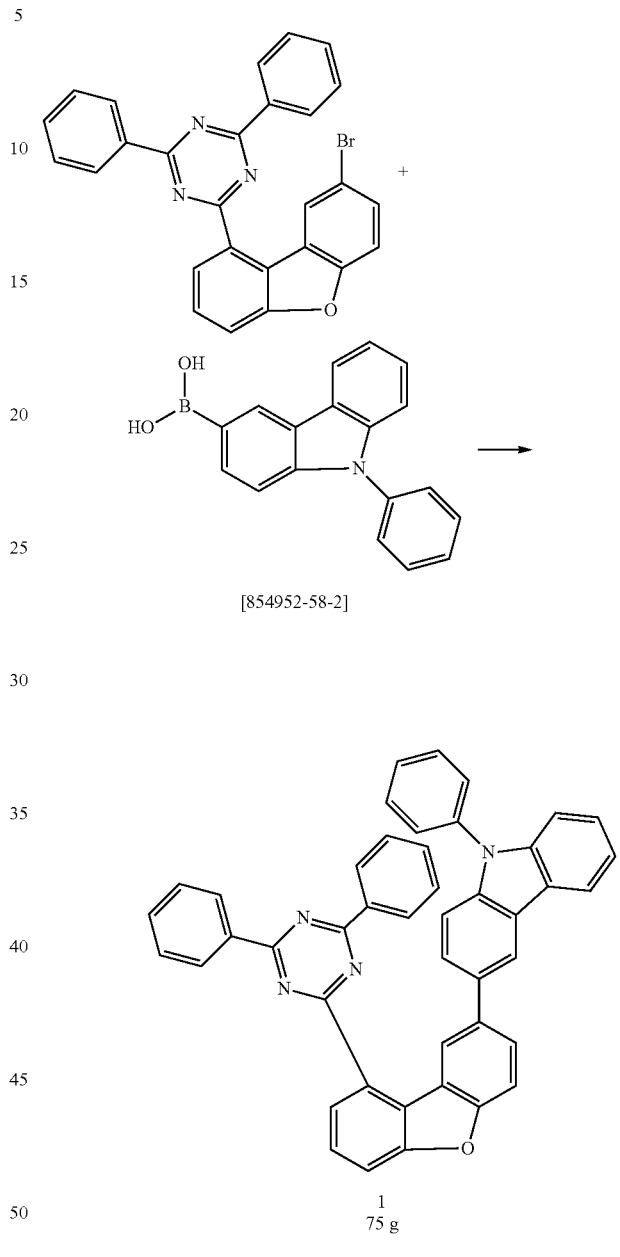

(156 mmol) of 2-(8-bromodibenzofuran-1-yl)-4,6-diphenyl-[1,3,5]-triazine, 50 g (172 mmol) of N-phenylcarbazole-3-boronic acid [854952-58-2] and 36 g (340 mmol) of sodium carbonate are suspended in 1000 ml of ethylene glycol diamine ether and 280 ml of water. 1.8 g (1.5 mmol) of tetrakis(triphenylphosphine)palladium(0) are added to this suspension, and the reaction mixture is heated under reflux for 16 h. After cooling, the organic phase is removed, filtered through silica gel, washed three times with 200 ml of water and then concentrated to dryness. The product is purified via column chromatography on silica gel with toluene/heptane (1:2) and finally sublimed under high vacuum (p=5×10$^{-7}$ mbar) (99.9% purity). The yield is 50 g (78 mmol), corresponding to 50% of theory.

In an analogous manner, it is possible to obtain the following substances:

| | Reactant 1 | Reactant 2 | Product | Yield |
|---|---|---|---|---|
| g1 | | [1572537-61-1] | | 61% |
| g2 | | [1814934-97-8] | | 63% |
| g3 | | [1702359-51-0] | | 64% |

-continued

| Reactant 1 | Reactant 2 | Product | Yield |
|---|---|---|---|
| g4 | [1572537-61-1] | | 66% |
| g5 | [1316311-24-6] | | 72% |
| g6 | [1572537-61-1] | | 77% |

-continued
| | Reactant 1 | Reactant 2 | Product | Yield |
|---|---|---|---|---|
| g7 | 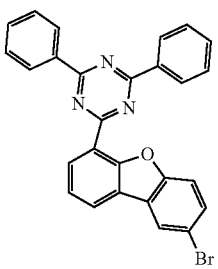 [1821221-55-9] | 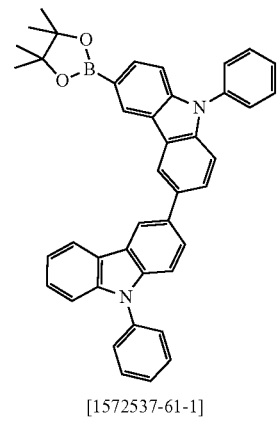 [SMILES: CC1(C)OB(c2ccc3c(c2)c2cc(-c4ccc5c(c4)c4ccccc4n5-c4ccccc4)ccc2n3-c2ccccc2)OC1(C)C] [1572537-61-1] | 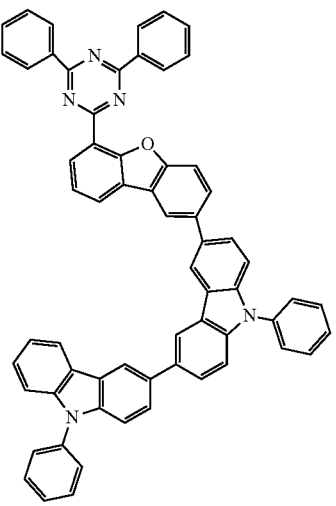 [SMILES: c1ccc(-c2nc(-c3ccccc3)nc(-c3cccc4c3oc3ccc(-c5ccc6c(c5)c5cc(-c7ccc8c(c7)c7ccccc7n8-c7ccccc7)ccc5n6-c5ccccc5)cc34)n2)cc1] | 73% |
| g8 | 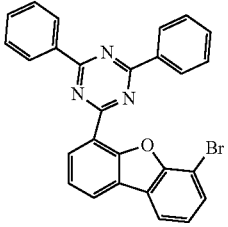 [1651196-06-3] | 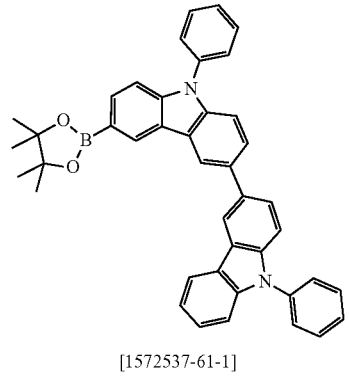 [SMILES: CC1(C)OB(c2ccc3c(c2)c2cc(-c4ccc5c(c4)c4ccccc4n5-c4ccccc4)ccc2n3-c2ccccc2)OC1(C)C] [1572537-61-1] | 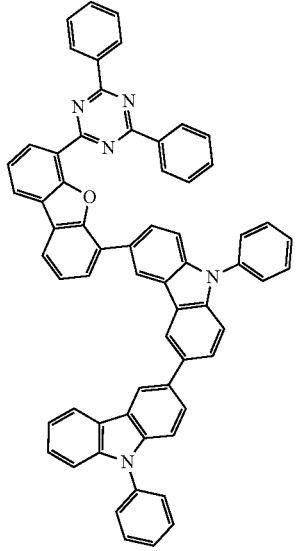 [SMILES: c1ccc(-c2nc(-c3ccccc3)nc(-c3cccc4c3oc3c(-c5ccc6c(c5)c5cc(-c7ccc8c(c7)c7ccccc7n8-c7ccccc7)ccc5n6-c5ccccc5)cccc34)n2)cc1] | 60% |

| Reactant 1 | Reactant 2 | Product | Yield |
|---|---|---|---|
| g9 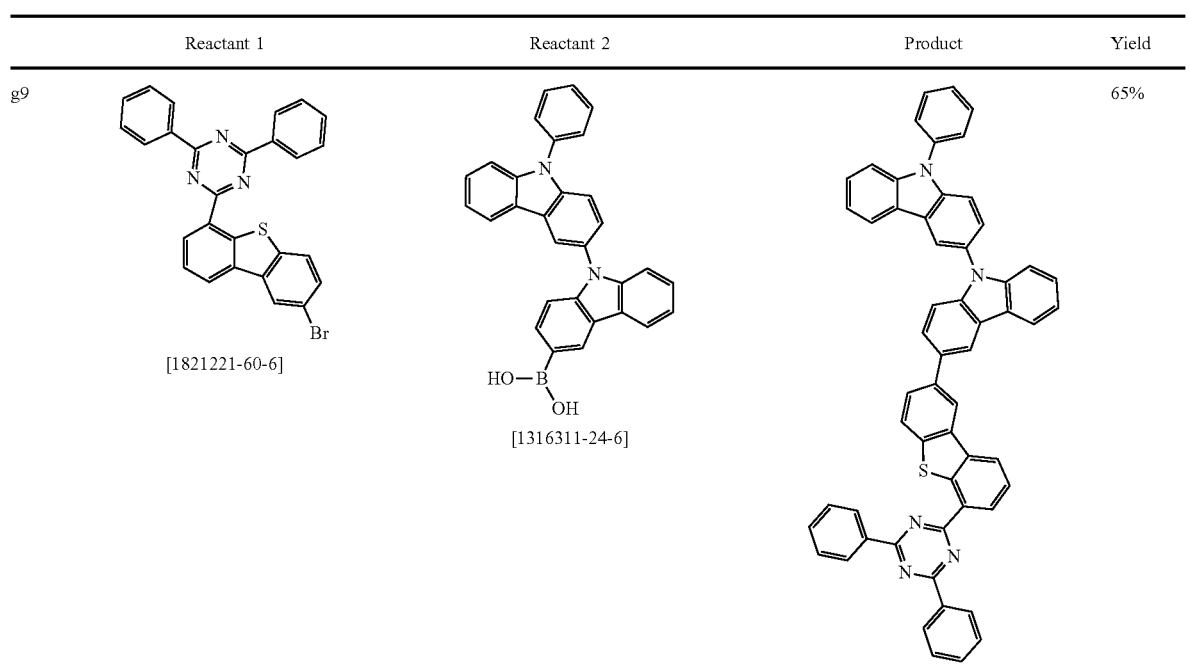 | | | 65% |
| g10 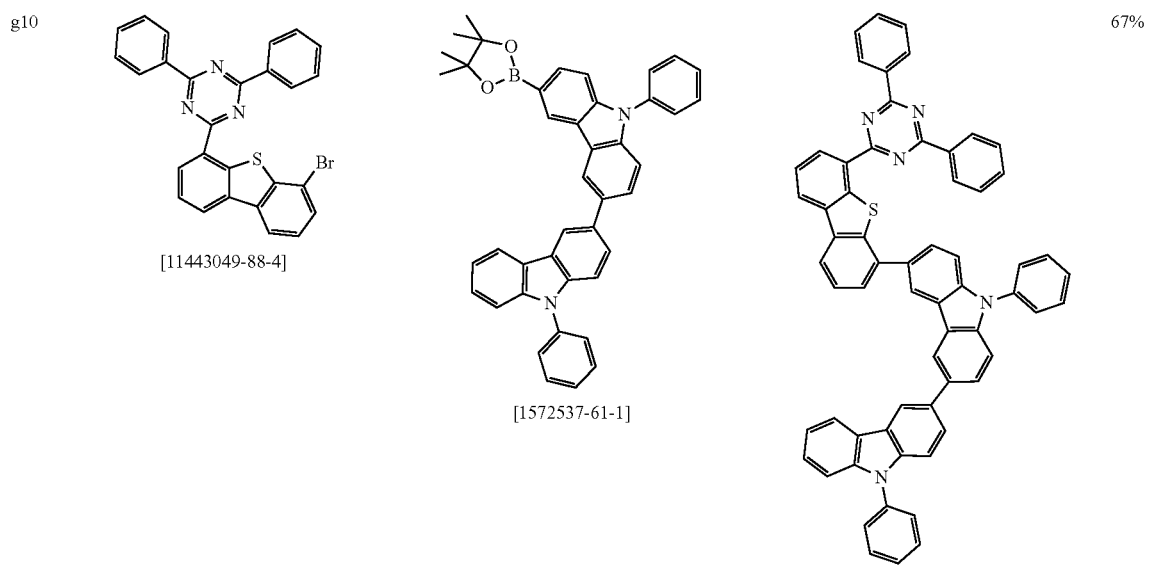 | | | 67% |

| Reactant 1 | Reactant 2 | Product | Yield |
|---|---|---|---|
| g11 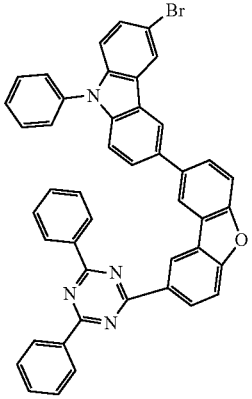 [SMILES: Brc1ccc2c(c1)c1cc(-c3ccc4oc5ccc(-c6nc(-c7ccccc7)nc(-c7ccccc7)n6)cc5c4c3)ccc1n2-c1ccccc1] | 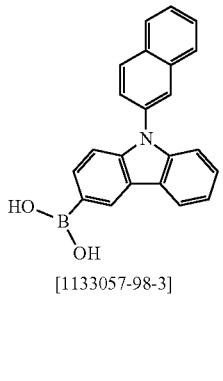 [SMILES: OB(O)c1ccc2c(c1)c1ccccc1n2-c1ccc2ccccc2c1][1133057-98-3] | 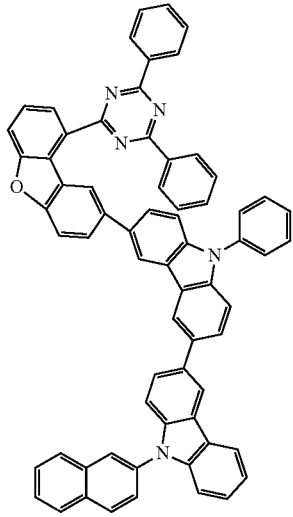 [SMILES: c1ccc(-c2nc(-c3ccccc3)nc(-c3cccc4oc5ccc(-c6ccc7c(c6)c6cc(-c8ccc9c(c8)c8ccccc8n9-c8ccc9ccccc9c8)ccc6n7-c6ccccc6)cc5c34)n2)cc1] | 67% |
| g12 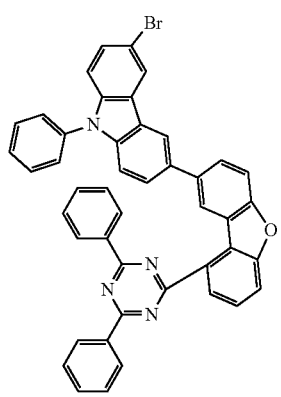 [SMILES: Brc1ccc2c(c1)c1cc(-c3ccc4oc5cccc(-c6nc(-c7ccccc7)nc(-c7ccccc7)n6)c5c4c3)ccc1n2-c1ccccc1] | 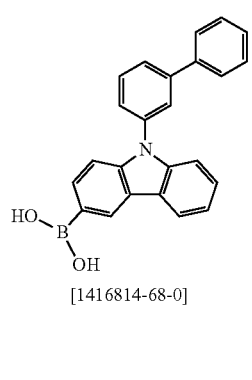 [SMILES: OB(O)c1ccc2c(c1)c1ccccc1n2-c1cccc(-c2ccccc2)c1][1416814-68-0] | 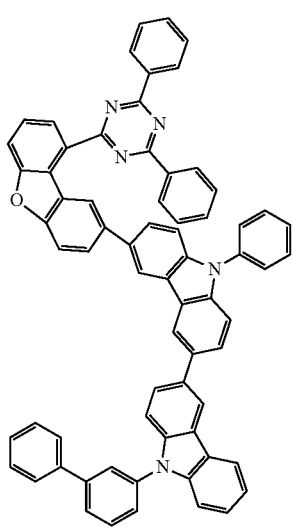 [SMILES: c1ccc(-c2cccc(-n3c4ccccc4c4cc(-c5ccc6c(c5)c5cc(-c7ccc8oc9cccc(-c%10nc(-c%11ccccc%11)nc(-c%11ccccc%11)n%10)c9c8c7)ccc5n6-c5ccccc5)ccc43)c2)cc1] | 62% |

135 h) 3-Bromo-6-[9-(4,6-diphenyl-[1,3,5]triazin-2-yl)
dibenzofuran-2-yl]-9-phenyl-9H-carbazole

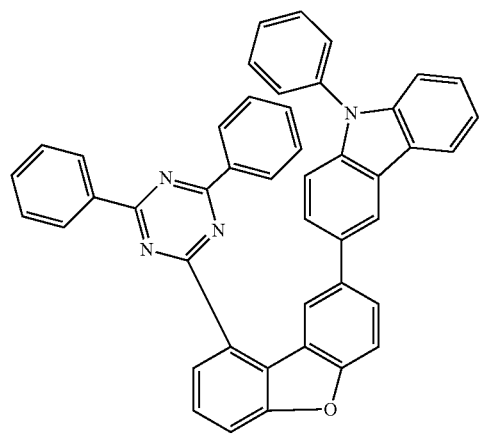

↓

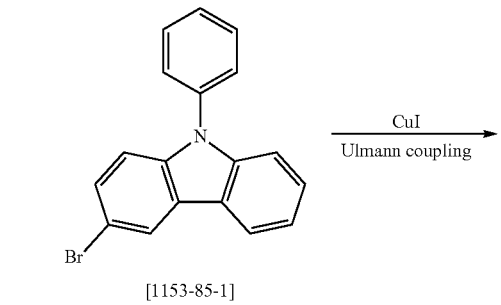

121 g (190.0 mmol) of 3-[9-(4,6-diphenyl[1,3,5]triazin-2-yl)dibenzofuran-2-yl]-9-phenyl-9H-carbazole are suspended in 2000 ml of acetic acid (100%) and 2000 ml of sulfuric acid (95-98%). 34 g (190 mmol) of NBS are added to this suspension in portions and the mixture is stirred in the dark for 2 h. Thereafter, water/ice is added and the solids are removed and washed with ethanol. The residue is recrystallized from toluene. The yield is 103 g (143 mmol), corresponding to 76% of theory.

136

EXAMPLE 3: SYNTHESIS OF COMPOUNDS OF THE FORMULA (1B)

a) 9-Phenyl-3'-(9-{4-phenyl-6-[(E)-((Z)-1-propenyl)
buta-1,3-dienyl]-[1,3,5]triazin-2-yl}dibenzofuran-2-
yl)-9H-[3,9']bicarbazole

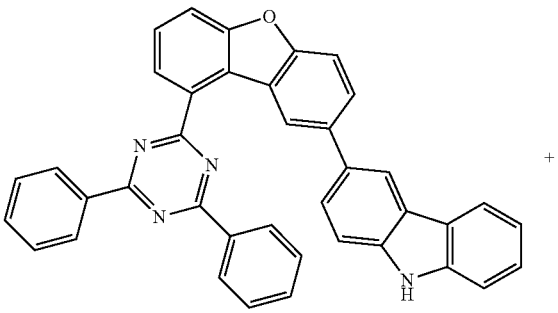

d13

+

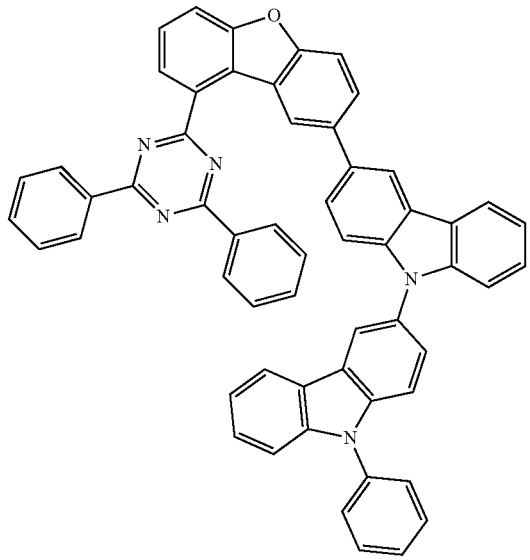

[1153-85-1]

$\xrightarrow{\text{CuI}}_{\text{Ulmann coupling}}$ 16.9 g (30 mmol) of 3-[9-(4,6-diphenyl[1,3,5]triazin-2-yl)dibenzofuran-2-yl]-9H-carbazole, 9.9 g (31 mmol, 1.1 eq) of 3-bromo-9-phenyl-9H-carbazole and 12.1 g (12 mmol, 0.36 eq) of copper(I) iodide are suspended with 150 g (706 mmol, 4 eq) of potassium phosphate in 1 l of 1,4-dioxane. Subsequently, the reaction mixture is degassed for 30 minutes, and 17.6 ml (147 mmol, 0.83 eq) trans-cyclohexylamine are added under protective gas. The mixture is heated under reflux for 12 h and, after the reaction has ended, dichloromethane is added. The precipitated solids are filtered off with suction, dissolved in toluene and filtered through silica gel. After the solvent has been removed under reduced pressure, the residue is recrystallized repeatedly from toluene/heptane and finally sublimed. 12.9 g (16 mmol, 54%) of a colourless solid having HPLC purity of >99.9% are obtained.

In a analogous manner, the following compounds are prepared:

| | Reactant 1 | Reactant 2 | Product | Yield [%] |
|---|---|---|---|---|
| 1e | | [94994-62-4] | | 76 |
| 2e | | [1097884-37-1] | | 60 |
| 3e | | [1174032-81-5] | | 58 |

| | Reactant 1 | Reactant 2 | Product | Yield [%] |
|---|---|---|---|---|
| 4e | 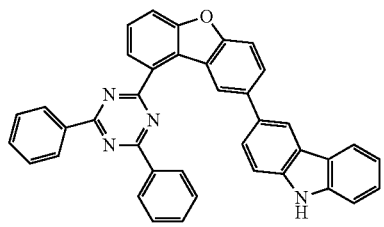 [SMILES: c1ccc(-c2nc(-c3ccccc3)nc(-c3cccc4oc5ccc(-c6ccc7[nH]c8ccccc8c7c6)cc5c34)n2)cc1] | 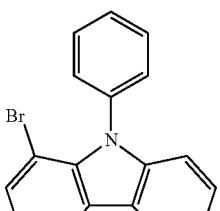  [1333002-37-1] | 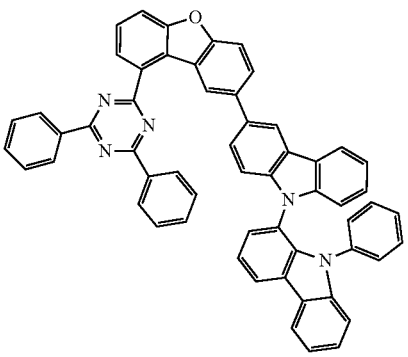 [SMILES: c1ccc(-c2nc(-c3ccccc3)nc(-c3cccc4oc5ccc(-c6ccc7c(c6)c6ccccc6n7-c6cccc7c8ccccc8n(-c8ccccc8)c67)cc5c34)n2)cc1] | 57 |
| 5e | 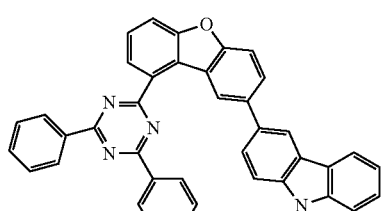 | 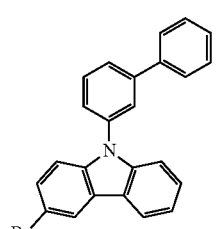  [1428551-28-3] | 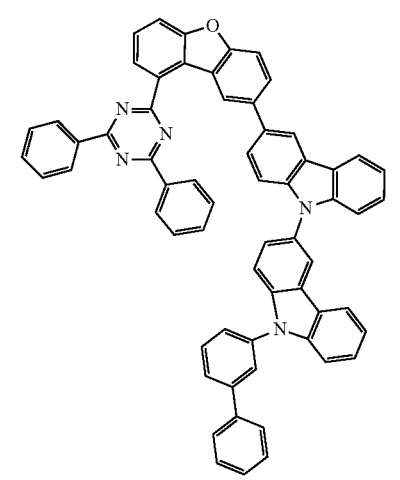 [SMILES: c1ccc(-c2cccc(-n3c4ccccc4c4cc(-n5c6ccccc6c6cc(-c7ccc8oc9cccc(-c%10nc(-c%11ccccc%11)nc(-c%11ccccc%11)n%10)c9c8c7)ccc65)ccc43)c2)cc1] | 49 |
| 6e | 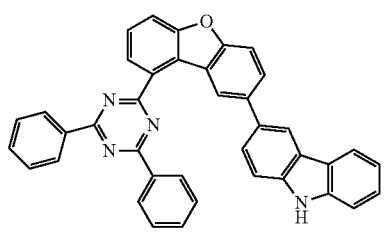 [SMILES: c1ccc(-c2nc(-c3ccccc3)nc(-c3cccc4oc5ccc(-c6ccc7[nH]c8ccccc8c7c6)cc5c34)n2)cc1] | 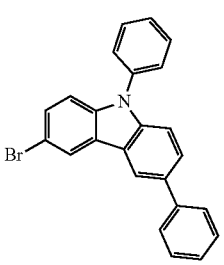  CAS 1160294-85-8 | 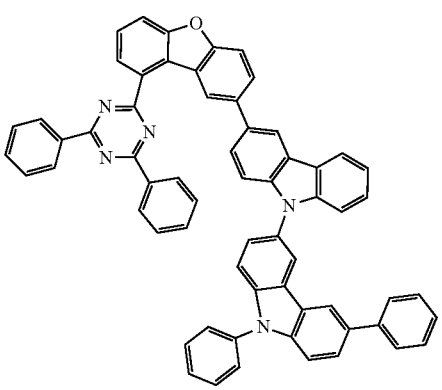 [SMILES: c1ccc(-c2ccc3c(c2)c2cc(-n4c5ccccc5c5cc(-c6ccc7oc8cccc(-c9nc(-c%10ccccc%10)nc(-c%10ccccc%10)n9)c8c7c6)ccc54)ccc2n3-c2ccccc2)cc1] | 45 |

EXAMPLE 4

Example 9 is known from the literature and is prepared analogously to WO 2009/021126, example 1.

EXAMPLE 5

Compounds 10 to 17 can be prepared analogously to Example 4.

The invention claimed is:

1. A composition comprising at least one compound of the formula (1) and at least one compound of the formula (2)

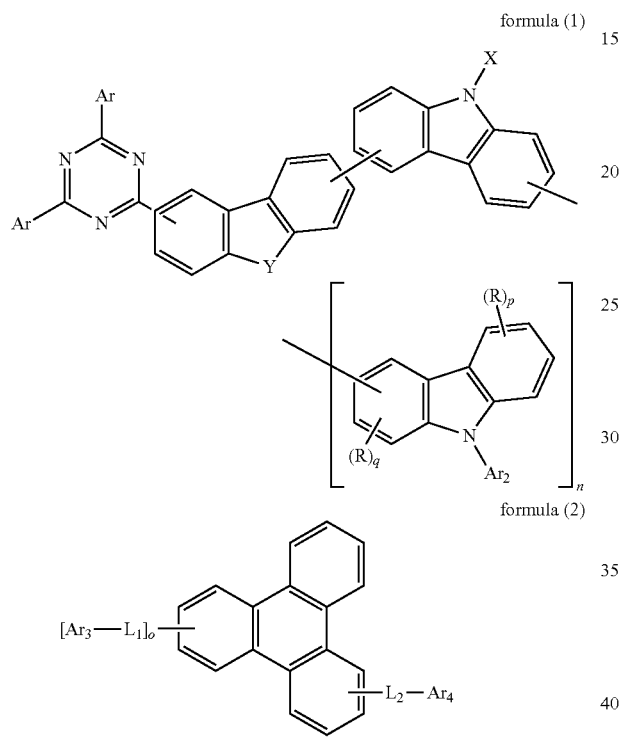

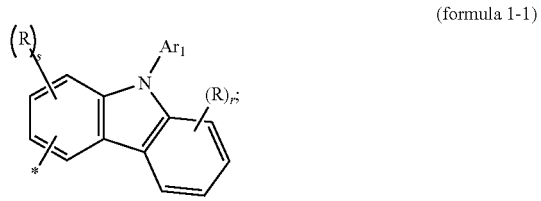

where the symbols and indices used are as follows:

X is the same or different at each instance and is $Ar_1$ or a substituent of the formula (1-1)

(formula 1-1)

Y is O or S;

Ar, $Ar_1$, $Ar_2$ are each independently at each instance an aryl or heteroaryl group which has 5 to 40 ring atoms and may be substituted by one or more $R^3$ radicals or an aromatic or heteroaromatic ring system which has 6 to 40 ring atoms and may be substituted by one or more $R^3$ radicals;

n is 0 or 1;

p, q are each independently 0, 1, 2, 3 or 4;

s, r are each independently 0, 1, 2, 3 or 4;

* is the attachment site to the nitrogen atom;

R is the same or different at each instance and is selected from the group consisting of D, F, Cl, Br, I, CN, $NO_2$, $N(Ar)_2$, $N(R^2)_2$, $C(=O)Ar$, $C(=O)R^2$, $P(=O)(Ar)_2$, $P(Ar)_2$, $B(Ar)_2$, $Si(Ar)_3$, $Si(R^2)_3$, a straight-chain alkyl, alkoxy or thioalkyl group having 1 to 20 carbon atoms or a branched or cyclic alkyl, alkoxy or thioalkyl group having 3 to 20 carbon atoms or an alkenyl group having 2 to 20 carbon atoms, each of which may be substituted by one or more $R^2$ radicals, where one or more non-adjacent $CH_2$ groups may be replaced by $R^2C=CR^2$, $Si(R^2)_2$, $C=O$, $C=S$, $C=NR^2$, $P(=O)(R^2)$, SO, $SO_2$, $NR^2$, O, S or $CONR^2$ and where one or more hydrogen atoms may be replaced by D, F, Cl, Br, I, CN or $NO_2$, an aromatic or heteroaromatic ring system which has 5 to 40 ring atoms and may be substituted in each case by one or more $R^2$ radicals, an aryloxy or heteroaryloxy group which has 5 to 40 ring atoms and may be substituted by one or more $R^2$ radicals, or an aralkyl or heteroaralkyl group which has 5 to 40 ring atoms and may be substituted by one or more $R^2$ radicals; at the same time, it is possible here for not more than one R substituent together with $Ar_1$ to form a monocyclic or polycyclic aliphatic, aromatic or heteroaromatic ring system which may be substituted by one or more $R^2$ radicals;

o is 0 or 1;

$L_1$, $L_2$ are the same or different at each instance and are a single bond or an aromatic or heteroaromatic ring system which has 5 to 30 ring atoms and may be substituted by one or more $R^3$ radicals;

$Ar_3$ and $Ar_4$ are each independently an aromatic or heteroaromatic ring system which has 6 to 40 ring atoms and may be substituted by one or more $R^1$ radicals;

$R^1$ is the same or different at each instance and is selected from the group consisting of H, D, F, Cl, Br, I, CN, $NO_2$, $N(Ar)_2$, $N(R^2)_2$, $C(=O)Ar$, $C(=O)R^2$, $P(=O)(Ar)_2$, $P(Ar)_2$, $B(Ar)_2$, $Si(Ar)_3$, $Si(R^2)_3$, a straight-chain alkyl, alkoxy or thioalkyl group having 1 to 20 carbon atoms or a branched or cyclic alkyl, alkoxy or thioalkyl group having 3 to 20 carbon atoms or an alkenyl group having 2 to 20 carbon atoms, each of which may be substituted by one or more $R^2$ radicals, where one or more nonadjacent $CH_2$ groups may be replaced by $R^2C=CR^2$, $Si(R^2)_2$, $C=O$, $C=S$, $C=NR^2$, $P(=O)(R^2)$, SO, $SO_2$, $NR^2$, O, S or $CONR^2$ and where one or more hydrogen atoms may be replaced by D, F, Cl, Br, I, CN or $NO_2$, an aromatic or heteroaromatic ring system which has 5 to 40 ring atoms and may be substituted in each case by one or more $R^2$ radicals, an aryloxy or heteroaryloxy group which has 5 to 40 ring atoms and may be substituted by one or more $R^2$ radicals, or an aralkyl or heteroaralkyl group which has 5 to 40 ring atoms and may be substituted by one or more $R^2$ radicals; at the same time, it is optionally possible for two substituents $R^1$ bonded to the same carbon atom or to adjacent carbon atoms to form a monocyclic or polycyclic, aliphatic, aromatic or heteroaromatic ring system which may be substituted by one or more $R^2$ radicals;

$R^2$ is the same or different at each instance and is selected from the group consisting of H, D, F, Cl, Br, I, CN, $NO_2$, $N(Ar)_2$, $NH_2$, $N(R^3)_2$, $C(=O)Ar$, $C(=O)H$, $C(=O)R^3$, $P(=O)(Ar)_2$, a straight-chain alkyl, alkoxy or thioalkyl group having 1 to 40 carbon atoms or a branched or cyclic alkyl, alkoxy or thioalkyl group having 3 to 40 carbon atoms or an alkenyl or alkynyl group having 2 to 40 carbon atoms, each of which may be substituted by one or more R³ radicals, where one or more nonadjacent CH₂ groups may be replaced by HC=CH, R³C=CR³, CC, Si(R³)₂, Ge(R³)₂, Sn(R³)₂, C=O, C=S, C=Se, C=NR³, P(=O)(R³), SO, SO₂, NH, NR³, O, S, CONH or CONR³ and where one or more hydrogen atoms may be replaced by D, F, Cl, Br, I, CN or NO₂, an aromatic or heteroaromatic ring system which has 5 to 60 ring atoms and may be substituted in each case by one or more R³ radicals, an aryloxy or heteroaryloxy group which has 5 to 60 ring atoms and may be substituted by one or more R³ radicals, or a combination of these systems; where it is optionally possible for two or more adjacent substituents R² to form a monocyclic or polycyclic, aliphatic, aromatic or heteroaromatic ring system which may be substituted by one or more R³ radicals;

R³ is the same or different at each instance and is selected from the group consisting of H, D, F, CN, an aliphatic hydrocarbyl radical having 1 to 20 carbon atoms, or an aromatic or heteroaromatic ring system having 5 to 30 ring atoms in which one or more hydrogen atoms may be replaced by D, F, Cl, Br, I or CN and which may be substituted by one or more alkyl groups each having 1 to 4 carbon atoms; at the same time, it is possible for two or more adjacent substituents R³ together to form a mono- or polycyclic, aliphatic ring system.

2. The composition according to claim 1, characterized in that the compound of the formula (1) conforms to the formula (1a) or (1b)

where the symbols and indices used have a definition as in claim 1.

3. The composition according to claim 1, characterized in that the compound of the formula (2) conforms to the formula (2a), (2b) or (2c)

formula (2a)

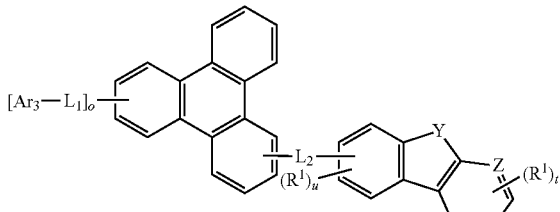

formula (2b)

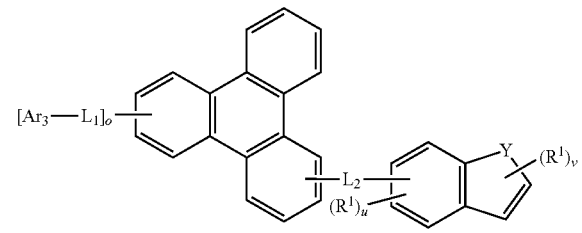

formula (1a)

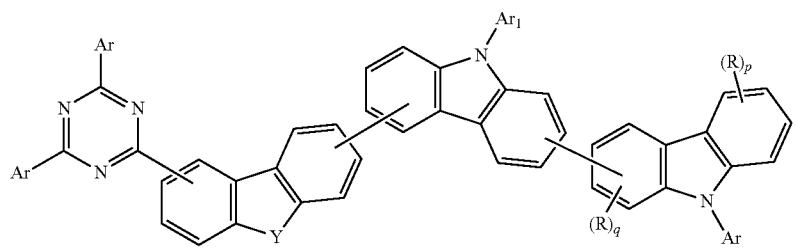

formula (1b)

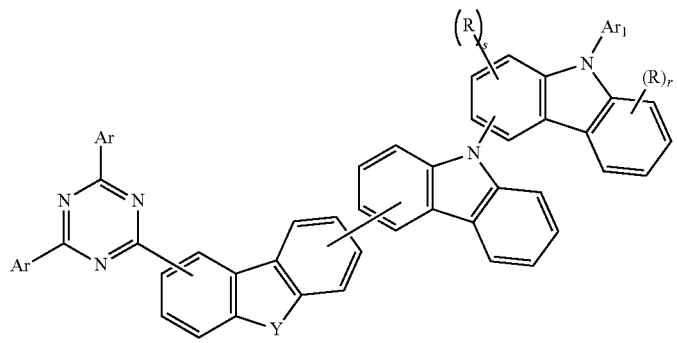

-continued formula (2c)

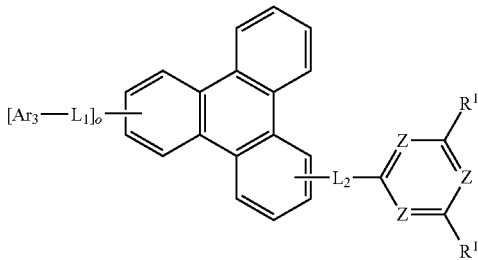

where symbols and indices used have a definition as in claim 1,

Z independently at each instance is N or $CR^1$ where $R^1$ has a definition specified in claim 1, Y is O or S, t and u are each independently 0, 1, 2 or 3, v is in each case independently 0, 1 or 2.

4. The composition according to claim 1, characterized in that the composition comprises at least one further compound selected from the group consisting of hole injection materials, hole transport materials, hole blocker materials, wide band gap materials, fluorescent emitters, phosphorescent emitters, host materials, electron blocker materials, electron transport materials and electron injection materials, n-dopants and p-dopants.

5. A formulation comprising a composition according to claim 1 and at least one solvent.

6. Use of a composition according to claim 1 in an organic electronic device.

7. Use according to claim 6, characterized in that the organic electronic device is selected from the group of organic integrated circuits (OICs), organic field-effect transistors (OFETs), organic thin-film transistors (OTFTs), organic electroluminescent devices, organic solar cells (OSCs), organic optical detectors and organic photoreceptors.

8. An organic electronic device comprising at least one composition according to claim 1.

9. The device according to claim 8, characterized in that the device is selected from the group of organic integrated circuits (OICs), organic field-effect transistors (OFETs), organic thin-film transistors (OTFTs), organic electroluminescent devices, organic solar cells (OSCs), organic optical detectors and organic photoreceptors.

10. The device according to claim 8, characterized in that the device is an electroluminescent device selected from the group consisting of organic light-emitting transistors (OLETs), organic field quench devices (OFQDs), organic light-emitting electrochemical cells (OLECs, LECs, LEECs), organic laser diodes (O-lasers) and organic light-emitting diodes (OLEDs).

11. The device according to claim 8, characterized in that the device comprises the composition in an emission layer (EML), in an electron transport layer (ETL), in an electron injection layer (EIL) and/or in a hole blocker layer (HBL).

12. The device according to claim 8, characterized in that the device comprises the composition in the emission layer together with a phosphorescent emitter.

13. A process for producing the device according to claim 8, characterized in that at least one organic layer comprising the composition is applied by gas phase deposition or from solution.

14. The process according to claim 13, characterized in that at least one compound of the formula (1) and at least one compound of the formula (2) are deposited from the gas phase successively or simultaneously from at least two material sources, optionally together with further materials, and form the organic layer.

15. The process according to claim 13, characterized in that the composition is utilized as material source for gas phase deposition and forms the organic layer.

16. The process according to claim 13, characterized in that the formulation is used in order to apply the organic layer.

* * * * *